US011021744B2

(12) United States Patent
Wittwer et al.

(10) Patent No.: US 11,021,744 B2
(45) Date of Patent: *Jun. 1, 2021

(54) METHODS FOR FAST NUCLEIC ACID AMPLIFICATION

(71) Applicant: University of Utah Research Foundation, Salt Lake City, UT (US)

(72) Inventors: Carl T. Wittwer, Salt Lake City, UT (US); Jared Steven Farrar, Richmond, VA (US)

(73) Assignee: University of Utah Research Foundation, Salt Lake City, UT (US)

( * ) Notice: Subject to any disclaimer, the term of this patent is extended or adjusted under 35 U.S.C. 154(b) by 299 days.

This patent is subject to a terminal disclaimer.

(21) Appl. No.: 16/179,383

(22) Filed: Nov. 2, 2018

(65) Prior Publication Data

US 2019/0055591 A1 Feb. 21, 2019

Related U.S. Application Data

(62) Division of application No. 15/890,843, filed on Feb. 7, 2018, now Pat. No. 10,144,960, which is a division of application No. 14/403,369, filed as application No. PCT/US2013/042473 on May 23, 2013, now Pat. No. 9,932,634.

(60) Provisional application No. 61/811,145, filed on Apr. 12, 2013, provisional application No. 61/651,161, filed on May 24, 2012.

(51) Int. Cl.
*C12P 19/34* (2006.01)
*C12Q 1/686* (2018.01)
*B01L 7/02* (2006.01)
*B01L 7/00* (2006.01)
*B01L 3/00* (2006.01)

(52) U.S. Cl.
CPC ............... *C12Q 1/686* (2013.01); *B01L 7/02* (2013.01); *B01L 7/52* (2013.01); *B01L 7/5255* (2013.01); *B01L 3/5027* (2013.01); *B01L 2200/06* (2013.01); *B01L 2300/0627* (2013.01); *B01L 2300/1894* (2013.01)

(58) Field of Classification Search
CPC ................................................... C12Q 1/686
See application file for complete search history.

(56) References Cited

U.S. PATENT DOCUMENTS

| | | |
|---|---|---|
| 5,436,149 A | 7/1995 | Barnes |
| 6,020,130 A | 2/2000 | Gold et al. |
| 6,210,882 B1 | 4/2001 | Landers et al. |
| 6,706,617 B2 | 3/2004 | Park |
| 8,003,370 B2 | 8/2011 | Maltezos et al. |
| 2002/0187475 A1* | 12/2002 | Coticone ............ C12Q 1/6848 435/6.12 |
| 2008/0248535 A1 | 10/2008 | Ankenbauer et al. |
| 2009/0269766 A1 | 10/2009 | Heindl et al. |
| 2009/0325169 A1 | 12/2009 | Walder et al. |
| 2010/0124765 A1 | 5/2010 | Lao et al. |
| 2011/0039305 A1 | 2/2011 | Termaat, Jr. et al. |
| 2012/0003645 A1 | 1/2012 | Yim et al. |
| 2012/0214207 A1 | 8/2012 | Gunter et al. |
| 2014/0141422 A1 | 5/2014 | Wang et al. |
| 2014/0199699 A1 | 7/2014 | Lee |
| 2015/0118715 A1 | 4/2015 | Wittwer et al. |

FOREIGN PATENT DOCUMENTS

| | | |
|---|---|---|
| CN | 101407850 | 4/2009 |
| EP | 0 511 712 A1 | 11/1992 |
| WO | WO 95/04161 A1 | 2/1995 |
| WO | WO 97/11085 A1 | 3/1997 |
| WO | WO 2015/069743 A1 | 5/2015 |

OTHER PUBLICATIONS

Agarwal et al. "Effect of Ramp Rates During Rapid Thermal Annealing of Iron Implanted Boron for Formation of Ultra-Shallow Junctions" *Journal of Electronic Materials* 28(12):1333-1339 (1999).
Agrawal et al. "A Pocket-Sized Convective PCR Thermocycler" *Angewandte Chemie* (International ed. in English) 46:4316-4319 (2007).
Belgrader et al. "Rapid pathogen detection using a microchip PCR array instrument" *Clinical Chemistry* 44(10):2191-2194 (1998).
Brown et al. "Rapid Cycle Amplification for Construction of Competitive Templates" *Genetic Engineering with PCR* pp. 57-70 (1998).
Chen et al. "Electrokinetically Synchronized Polymerase Chain Reaction Microchip Fabricated in Polycarbonate" *Analytical Chemistry* 77:658-666 (2005).
Cheng et al. "Chip PCR. II. Investigation of different PCR amplification systems in microfabricated silicon-glass chips" *Nucleic Acids Research* 24(2):380-385 (1996).
Chiou et al. "Thirty-Cycle Temperature Optimization of a Closed-Cycle Capillary PCR Machine" *BioTechniques* 33:557-564 (2002).
Crews et al. "Continuous-flow thermal gradient PCR" *Biomedical Microdevices* 10:187-195 (2008).
Czerny, Thomas "High primer concentration improves PCR amplification from random pools" *Nucleic Acids Research* 24(5):985-986 (1996).
Di Giusto et al. "Single Base Extension (SBE) with Proofreading Polymerases and Phosphorothioate Primers: Improved Fidelity in Single-Substrate Assays" *Nucleic Acids Research* 31(3):1-12 (2003).
Elenitoba-Johnson et al. "Plastic versus glass capillaries for rapid-cycle PCR" *BioTechniques* 44:487-492 (2008).

(Continued)

*Primary Examiner* — Kenneth R Horlick

(74) *Attorney, Agent, or Firm* — Myers Bigel, P.A.

(57) ABSTRACT

Methods, devices, and kits are provided for performing PCR in <20 seconds per cycle, with improved efficiency and yield.

6 Claims, 33 Drawing Sheets

Specification includes a Sequence Listing.

(56) References Cited

OTHER PUBLICATIONS

Erlich, Henry A. "The Design and Optimization of the PCR" *PCR Technology: Principles and Applications for DNA Amplification* Chapter 1:8-16 (1989).
Farrar et al. "Extreme PCR: Efficient and Specific DNA Amplification in 15-60 Seconds" *Clinical Chemistry* 61(1):145-153 (2015).
Frey et al. "Autonomous microfluidic multi-channel chip for real-time PCR with integrated liquid handling" *Biomedical Microdevices* 9:711-718 (2007).
Friedman et al. "Capillary Tube Resistive Thermal Cycling" *Analytical Chemistry* 70:2997-3002 (1998).
Fuchiwaki et al. "A Practical Liquid Plug Flow-through Polymerase Chain-Reaction System Based on a Heat-Resistant Resin Chip" *Analytical Sciences* 27:225-230 (2011).
Fuchiwaki et al. "Study of DNA Amplification Efficiency Based on Temperature Analyses of the Moving Fluid in a Liquid-Plug Flow PCR System" *Bulletin of the Chemical Society of Japan* 84(10):1075-1081 (2011).
Fuchiwaki et al. "Ultra-rapid flow-through polymerase chain reaction microfluidics using vapor pressure" *Biosensors and Bioelectronics* 27:88-94 (2011).
Gerard et al. "Reverse Transcriptase (EC 2.7.7.49): The Use of Cloned Moloney Murine Leukemia Virus Reverse Transcriptase to Synthesize DNA from RNA" *Methods in Molecular Biology; Enzymes of Molecular Biology* 16:73-93 (1993).
Giordano et al. "Polymerase Chain Reaction in Polymeric Microchips: DNA Amplification in Less Than 240 Seconds" *Analytical Biochemistry* 291:124-132 (2001).
Gundry et al. "Obtaining Maximum PCR Sensitivity and Specificity" *PCR Troubleshooting and Optimization: The Essential Guide* Chapter 4:79-96 (2011).
Hashimoto et al. "Rapid PCR in a continuous flow device" *Lab Chip* 4:638-645 (2004).
Heap et al. "PCR Amplification Using Electrolytic Resistance for Heating and Temperature Monitoring" *BioTechniques* 29:1006-1012 (2000).
Herrmann et al. "Amplicon DNA Melting Analysis for Mutation Scanning and Genotyping: Cross-Platform Comparison of Instruments and Dyes" *Clinical Chemistry* 52(3):494-503 (2006).
Herrmann et al. "Expanded Instrument Comparison of Amplicon DNA Melting Analysis for Mutation Scanning and Genotyping" *Clinical Chemistry* 53(8):1544-1548 (2007).
Innis et al. "DNA sequencing with *Thermus aquaticus* DNA polymerase and direct sequencing of polymerase chain reaction-amplified DNA" *Proceedings of the National Academy of Sciences* 85:9436-9440 (1988).
Innis et al. "Optimization of PCRs" *PCR Protocols: A Guide to Methods and Applications* Chapter 1:3-12 (1990).
International Preliminary Report on Patentability Corresponding to International Application No. PCT/US2013/042473 (dated Dec. 4, 2014).
International Search Report and the Written Opinion of the International Searching Authority Corresponding to International Application No. PCT/US2013/042473 (dated Dec. 20, 2013).
Kim et al. "Nanodroplet real-time PCR system with laser assisted heating" *Optics Express* 17(1):218-227 (2009).
Kopp et al. "Chemical Amplification: Continuous-Flow PCR on a Chip" *Science* 280(5366):1046-1048 (1998).
Lawyer et al. "High-level Expression, Purification, and Enzymatic Characterization of Full-length *Thermus aquaticus* DNA Polymerase and a Truncated Form Deficient in 5' to 3' Exonuclease Activity" *Genome Research* 2:275-287 (1993).
Maltezos et al. "Exploring the limits of ultrafast polymerase chain reaction using liquid for thermal heat exchange: A proof of principle" *Applied Physics Letters* 97:264101 (2010).
Montgomery et al. "Stopped-flow DNA polymerase assay by continuous monitoring of dNTP incorporation by fluorescence" *Analytical Biochemistry* 441:133-139 (2013).

Montgomery et al. "Influence of PCR Reagents on DNA Polymerase Extension Rates Measured on Real-Time PCR Instruments" *Clinical Chemistry* 60(2):334-340 (2014).
Neuzil et al. "Ultra fast miniaturized real-time PCR: 40 cycles in less than six minutes" *Nucleic Acids Research* 34(11):e77 (2006).
Obeid et al. "Microfabricated Device for DNA and RNA Amplification by Continuous-Flow Polymerase Chain Reaction and Reverse Transcription-Polymerase Chain Reaction with Cycle Number Selection" *Analytical Chemistry* 75:288-295 (2003).
Oda et al. "Infrared-Mediated Thermocycling for Ultrafast Polymerase Chain Reaction Amplification of DNA" *Analytical Chemistry* 70:4361-4368 (1998).
Partial Supplementary European Search Report corresponding to European Patent Application No. 13793389.1 (10 pages) (dated Mar. 7, 2016).
Promega "GoTaq® 1-Step RT-qPCR System: Instructions for Use of Product" *Technical Manual* pp. 1-12 (2014).
Raja et al. "Temperature-controlled Primer Limit for Multiplexing of Rapid, Quantitative Reverse Transcription-PCR Assays: Application to Intraoperative Cancer Diagnostics" *Clinical Chemistry* 48(8):1329-1337 (2002).
Ririe et al. "Product Differentiation by Analysis of DNA Melting Curves during the Polymerase Chain Reaction" *Analytical Biochemistry* 245:154-160 (1997).
Roper et al. "Advances in Polymerase Chain Reaction on Microfluidic Chips" *Analytical Chemistry* 77:3887-3894 (2005).
Roper et al. "Infrared Temperature Control System for a Completely Noncontact Polymerase Chain Reaction in Microfluidic Chips" *Analytical Chemistry* 79:1294-1300 (2007).
Schoder et al. "Novel Approach for Assessing Performance of PCR Cyclers Used for Diagnostic Testing" *Journal of Clinical Microbiology* 43(6):2724-2728 (2005).
Smith, Caitlin "Fast PCR: A Relay Between Instrument and Enzyme" *Biocompare Editorial Article* (3 pages) (Jan. 21, 2008).
Sun et al. "A circular ferrofluid driven microchip for rapid polymerase chain reaction" *Lab Chip* 7:1012-1017 (2007).
"TagMan® EZ RT-PCR Kit: Protocol" 50 pages (2002).
"Taq PCR Kit: Instruction Manual" 16 pages (2009).
Terazono et al. "Development of 1480 nm Photothermal High-Speed Real-Time Polymerase Chain Reaction System for Rapid Nucleotide Recognition" *Japanese Journal of Applied Physics* 47(6):5212-5216 (2008).
Terazono et al. "Development of a High-Speed Real-Time Polymerase Chain Reaction System Using a Circulating Water-Based Rapid Heat-Exchange" *Japanese Journal of Applied Physics* 49:1-5 (2010).
Von Ahsen et al. "Oligonucleotide Melting Temperatures under PCR Conditions: Nearest-Neighbor Corrections for $Mg^{2+}$, Deoxynucleotide Triphosphate, and Dimethyl Sulfoxide Concentrations with Comparison to Alternative Empirical Formulas" *Clinical Chemistry* 47(11):1956-1961 (2001).
Von Kanel et al. "Sample Number and Denaturation Time Are Crucial for the Accuracy of Capillary-Based LightCyclers" *Clinical Chemistry* 53(7):1392-1394 (2007).
Weis et al. "Detection of rare mRNAs via quantitative RT-PCR" *Trends in Genetics* 8(8):263-264 (1992).
Wheeler et al. "Convectively Driven Polymerase Chain Reaction Thermal Cycler" *Analytical Chemistry* 76:4011-4016 (2004).
Wheeler et al. "Under-three minute PCR: Probing the limits of fast amplification" *Analyst* 136:3707-3712 (2011).
Whitney, Scott E. "Analysis of Rapid Thermocycling for the Polymerase Chain Reaction" *Dissertation* (267 pages) (May 2004).
Wilhelm et al. "Influence of DNA Target Melting Behavior on Real-Time PCR Quantification" *Clinical Chemistry* 46(11):1738-1743 (2000).
Wittwer et al. "Automated polymerase chain reaction in capillary tubes with hot air" *Nucleic Acids Research* 17(11):4353-4357 (1989).
Wittwer et al. "Minimizing the Time Required for DNA Amplification by Efficient Heat Transfer to Small Samples" *Analytical Biochemistry* 186:328-331 (1990).
Wittwer et al. "Rapid Cycle DNA Amplification: Time and Temperature Optimization" *BioTechniques* 10(1):76-83 (1991).

(56) References Cited

OTHER PUBLICATIONS

Wittwer et al. "Rapid Cycle Allele-Specific Amplification: Studies with the Cystic Fibrosis ΔF$_{508}$ Locus" *Clinical Chemistry* 39(5):804-809 (1993).
Wittwer et al. "Continuous Fluorescence Monitoring of Rapid Cycle DNA Amplification" *BioTechniques* 22:130-138 (1997).
Wittwer et al. "The LightCycler™: A Microvolume Multisample Fluorimeter with Rapid Temperature Control" *BioTechniques* 22:176-181 (1997).
Wittwer et al. "Rapid Thermal Cycling and PCR Kinetics" *PCR Methods Manual* 14:211-229 (1999).
Wittwer et al. "High-Resolution Genotyping by Amplicon Melting Analysis Using LCGreen" *Clinical Chemistry* 49(6):853-860 (2003).
Wittwer et al. "Rapid polymerase chain reaction and melting analysis" *The PCR Revolution: Basic Technologies and Applications* (pp. 48-69) (2010).
Woolley et al. "Functional Integration of PCR Amplification and Capillary Electrophoresis in a Microfabricated DNA Analysis Device" *Analytical Chemistry* 68:4081-4086 (1996).
Zhang et al. "PCR microfluidic devices for DNA amplification" *Biotechnology Advances* 24:243-284 (2006).
Zhang et al. "Miniaturized PCR chips for nucleic acid amplification and analysis: latest advances and future trends" *Nucleic Acids Research* 35(13):4223-4237 (2007).
Zuna et al. "Temperature Non-homogeneity in Rapid Airflow-Based Cycler Significantly Affects Real-Time PCR" *BioTechniques* 33:508-512 (2002).
Rutschke et al. "Hot start reverse transcriptase: an approach for improved real-time RT-PCR performance" Journal of Analytical Science and Technology, 6:20, pp. 1-5 (2015).
Sellner et al. "Reverse transcriptase inhibits Taq polymerase activity" *Nucleic Acids Research*, 20(7):1487-1490 (1992).

\* cited by examiner

```
                              SEQUENCE LISTING

<160> NUMBER OF SEQ ID NOS: 27

<210> SEQ ID NO 1
<211> LENGTH: 24
<212> TYPE: DNA
<213> ORGANISM: Homo sapiens

<400> SEQUENCE: 1
cccattcaac gtctacatcg agtc                                              24

<210> SEQ ID NO 2
<211> LENGTH: 19
<212> TYPE: DNA
<213> ORGANISM: Homo sapiens

<400> SEQUENCE: 2
tccttctctt gccaggcat                                                    19

<210> SEQ ID NO 3
<211> LENGTH: 45
<212> TYPE: DNA
<213> ORGANISM: Homo sapiens
<220> FEATURE:
<221> NAME/KEY: mutation
<222> LOCATION: (23)..(23)
<223> OTHER INFORMATION: G or A residue

<400> SEQUENCE: 3
cccattcaac gtctacatcg agtccgatgc ctggcaagag aagga                       45

<210> SEQ ID NO 4
<211> LENGTH: 20
<212> TYPE: DNA
<213> ORGANISM: Homo sapiens

<400> SEQUENCE: 4
ctacagtggg agtcacctgc                                                   20

<210> SEQ ID NO 5
<211> LENGTH: 25
<212> TYPE: DNA
<213> ORGANISM: Homo sapiens

<400> SEQUENCE: 5
ggtactgagc tgtgaaagtc aggtt                                             25

<210> SEQ ID NO 6
<211> LENGTH: 58
<212> TYPE: DNA
<213> ORGANISM: Homo sapiens
<220> FEATURE:
<221> NAME/KEY: mutation
<222> LOCATION: (28)..(28)
<223> OTHER INFORMATION: A or G residue

<400> SEQUENCE: 6
ctacagtggg agtcacctgc ttttgccaaa gggaacctga ctttcacagc tcagtacc         58

<210> SEQ ID NO 7
<211> LENGTH: 20
<212> TYPE: DNA
<213> ORGANISM: Homo sapiens
```

<400> SEQUENCE: 7
gggagtcacc tgcttttgcc                                        20

<210> SEQ ID NO 8
<211> LENGTH: 25
<212> TYPE: DNA
<213> ORGANISM: Homo sapiens

<400> SEQUENCE: 8
tactgagctg tgaaagtcag gttcc                                  25

<210> SEQ ID NO 9
<211> LENGTH: 49
<212> TYPE: DNA
<213> ORGANISM: Homo sapiens

<400> SEQUENCE: 9
gggagtcacc tgcttttgcc aaagggaacc tgactttcac agctcagta         49

<210> SEQ ID NO 10
<211> LENGTH: 34
<212> TYPE: DNA
<213> ORGANISM: Homo sapiens

<400> SEQUENCE: 10
ctctgtgctt tctgtatcct cagagtggca ttct                        34

<210> SEQ ID NO 11
<211> LENGTH: 28
<212> TYPE: DNA
<213> ORGANISM: Homo sapiens

<400> SEQUENCE: 11
cgtctgctgg agtgtgccca atgctata                               28

<210> SEQ ID NO 12
<211> LENGTH: 60
<212> TYPE: DNA
<213> ORGANISM: Homo sapiens
<220> FEATURE:
<221> NAME/KEY: misc_feature
<222> LOCATION: (1)..(41)
<223> OTHER INFORMATION: 5' standard synthetic region

<400> SEQUENCE: 12
acacacacac acacacacac acacacacac acacacaaaa attcagtggc attaaatacg   60

<210> SEQ ID NO 13
<211> LENGTH: 67
<212> TYPE: DNA
<213> ORGANISM: Homo sapiens
<220> FEATURE:
<221> NAME/KEY: misc_feature
<222> LOCATION: (1)..(50)
<223> OTHER INFORMATION: 5' standard synthetic region

<400> SEQUENCE: 13
gagagagaga gagagagaga gagagagaga gagagagaga gagagaaaaa ccagagctaa   60
agggaag                                                           67

<210> SEQ ID NO 14
<211> LENGTH: 66
<212> TYPE: DNA
<213> ORGANISM: Homo sapiens

```
<220> FEATURE:
<221> NAME/KEY: misc_feature
<222> LOCATION: (1)..(41)
<223> OTHER INFORMATION: 5' standard synthetic region

<400> SEQUENCE: 14
acacacacac acacacacac acacacacac acacacaaaa agctggtgtc tgctatagaa    60
ctgatt                                                               66

<210> SEQ ID NO 15
<211> LENGTH: 72
<212> TYPE: DNA
<213> ORGANISM: Homo sapiens
<220> FEATURE:
<221> NAME/KEY: misc_feature
<222> LOCATION: (1)..(50)
<223> OTHER INFORMATION: 5' standard synthetic region

<400> SEQUENCE: 15
gagagagaga gagagagaga gagagagaga gagagagaga gagagaaaaa gttgccagag    60
ctaaagggaa gg                                                        72

<210> SEQ ID NO 16
<211> LENGTH: 41
<212> TYPE: DNA
<213> ORGANISM: Artificial Sequence
<220> FEATURE:
<223> OTHER INFORMATION: Synthetic common primer

<400> SEQUENCE: 16
acacacacac acacacacac acacacacac acacacaaaa a                        41

<210> SEQ ID NO 17
<211> LENGTH: 50
<212> TYPE: DNA
<213> ORGANISM: Artificial Sequence
<220> FEATURE:
<223> OTHER INFORMATION: Synthetic common primer

<400> SEQUENCE: 17
gagagagaga gagagagaga gagagagaga gagagagaga gagagaaaaa               50

<210> SEQ ID NO 18
<211> LENGTH: 24
<212> TYPE: DNA
<213> ORGANISM: Artificial Sequence
<220> FEATURE:
<223> OTHER INFORMATION: Synthetic common primer

<400> SEQUENCE: 18
actcgcacga actcaccgca ctcc                                           24

<210> SEQ ID NO 19
<211> LENGTH: 24
<212> TYPE: DNA
<213> ORGANISM: Artificial Sequence
<220> FEATURE:
<223> OTHER INFORMATION: Synthetic common primer

<400> SEQUENCE: 19
actcgcacga actcaccgca ctcc                                           24

<210> SEQ ID NO 20
<211> LENGTH: 100
<212> TYPE: DNA
```

<213> ORGANISM: Artificial Sequence
<220> FEATURE:
<223> OTHER INFORMATION: Synthetic template

<400> SEQUENCE: 20

| | | | | | |
|---|---|---|---|---|---|
| actcgcacga | actcaccgca | ctccggatgg | attgtgaaga | ggcccaagat | actggtcata | 60 |
| ttatcctttg | atctagctct | cactcgcact | ctcacgcaca | | | 100 |

<210> SEQ ID NO 21
<211> LENGTH: 200
<212> TYPE: DNA
<213> ORGANISM: Artificial Sequence
<220> FEATURE:
<223> OTHER INFORMATION: Synthetic template

<400> SEQUENCE: 21

| | | | | | |
|---|---|---|---|---|---|
| actcgcacga | actcaccgca | ctcctcaatg | ctgacaaatc | gaaagaatag | gaatagcgta | 60 |
| attactagag | gactccaata | tagtatatta | ccctggtgac | cgcctgtact | gtaggaacac | 120 |
| taccgcggtt | atattgacag | cttagcaatc | taccctgttg | ggatctgttt | aagtggctct | 180 |
| cactcgcact | ctcacgcaca | | | | | 200 |

<210> SEQ ID NO 22
<211> LENGTH: 300
<212> TYPE: DNA
<213> ORGANISM: Artificial Sequence
<220> FEATURE:
<223> OTHER INFORMATION: Synthetic template

<400> SEQUENCE: 22

| | | | | | |
|---|---|---|---|---|---|
| actcgcacga | actcaccgca | ctccccttcg | aatataaagt | acgacattac | tagcaatgac | 60 |
| agttccagga | tttaagaaag | tagtgttcca | catcaatgca | tatccagtga | aagcataacg | 120 |
| tcaaaaaaag | cctggcaccg | ttcgcgatct | ggacttactt | agatttgttg | tagtcaagcc | 180 |
| ggctatcagc | gatttatccc | ggaaacacat | actagtgagt | tatttgtatg | ttacctagaa | 240 |
| tagctgtcac | gaatcactaa | tacattcacc | caccagctct | cactcgcact | ctcacgcaca | 300 |

<210> SEQ ID NO 23
<211> LENGTH: 400
<212> TYPE: DNA
<213> ORGANISM: Artificial Sequence
<220> FEATURE:
<223> OTHER INFORMATION: Synthetic template

<400> SEQUENCE: 23

| | | | | | |
|---|---|---|---|---|---|
| actcgcacga | actcaccgca | ctcctgaata | caagacgaca | gtcctgatta | tattttcatt | 60 |
| taattacgcc | aatttaatta | tgatgaatat | taacggaatt | aaatatgtat | tgataagtac | 120 |
| taagtaatgg | tttacccacg | gcgatctata | tgcaagggaa | acattaacaa | atttaaacat | 180 |
| ctgatgtgga | caaaacttgt | aatgtggtat | agttaaaaat | ataggtttca | gggacacgta | 240 |
| agtatctatc | ttgaatgttt | aagtaggtcc | tgtctaccat | tctgaaattt | agaaaatcgc | 300 |
| gttcatcggg | ctgtcggcta | cacctcagaa | aaccatttcg | tgttgcacag | gaggaacttt | 360 |
| cgagggttcg | tatgagctct | cactcgcact | ctcacgcaca | | | 400 |

<210> SEQ ID NO 24
<211> LENGTH: 500
<212> TYPE: DNA
<213> ORGANISM: Artificial Sequence
<220> FEATURE:
<223> OTHER INFORMATION: Synthetic template -continued

```
<400> SEQUENCE: 24
actcgcacga actcaccgca ctccaccgct tgacgacgta gggtatttgg tatctgaatc       60
tactcattta cctacatact gaagattttg cgatcgtcta atatattgga ctaatgcccg      120
atttctgatc aattactcta ggcgatactt catcgctggc cttatttgga ttttgctcaa      180
gtgctaaact ctctgcgcgt caatactagt ctgacatcag tcaagacctg ctatctgaaa      240
actactagag agatatacct aacaacttta gtggataaat caggtctgga gattgtcata      300
taatgccact agggtcagaa ggctgtgtca aagttagtgg ttagtaggtc tccgctctgc      360
ggtactattc ttatattctc ttactatgca tcaaacaaaa tagaatgcat agacaaaccg      420
cctgccaagt ttacaagata acttgcgtat aggtttataa gggttcttct gtatcgctct      480
cactcgcact ctcacgcaca                                                  500

<210> SEQ ID NO 25
<211> LENGTH: 31
<212> TYPE: DNA
<213> ORGANISM: Homo sapiens

<400> SEQUENCE: 25
gcttggaaga ttgctaaaat gatagtcagt g                                      31

<210> SEQ ID NO 26
<211> LENGTH: 26
<212> TYPE: DNA
<213> ORGANISM: Homo sapiens

<400> SEQUENCE: 26
ttgatcatac tgagcctgct gcataa                                            26

<210> SEQ ID NO 27
<211> LENGTH: 60
<212> TYPE: DNA
<213> ORGANISM: Homo sapiens
<220> FEATURE:
<221> NAME/KEY: mutation
<222> LOCATION: (34)..(34)
<223> OTHER INFORMATION: A or G residue

<400> SEQUENCE: 27
gcttggaaga ttgctaaaat gatagtcagt gacattatgc agcaggctca gtatgatcaa       60
```

METHODS FOR FAST NUCLEIC ACID AMPLIFICATION

PRIORITY STATEMENT

This application is a divisional application of, and claims priority to, U.S. application Ser. No. 15/890,843, filed Feb. 7, 2018, now U.S. Pat. No. 10,144,960, issued Dec. 4, 2018 which is a divisional application of U.S. application Ser. No. 14/403,369, filed Nov. 24, 2014, now U.S. Pat. No. 9,932, 634, issued Apr. 3, 2018, which is a 35 U.S.C. § 371 national phase application of PCT Application Serial No. PCT/US2013/042473, filed May 23, 2013, which claims the benefit, under 35 U.S.C. § 119(e) of U.S. Provisional Patent Application Ser. No. 61/811,145, filed Apr. 12, 2013, and U.S. Provisional Patent Application Ser. No. 61/651,161, filed May 24, 2012, the entire contents of each of which are incorporated by referenced herein.

STATEMENT REGARDING ELECTRONIC FILING OF A SEQUENCE LISTING

A Sequence Listing in ASCII text format, submitted under 37 C.F.R. § 1.821, entitled 1267-9TSDV2_ST25.txt, 7,390 bytes in size, generated on Nov. 2, 2018 and filed via EFS-Web, is provided in lieu of a paper copy. This Sequence Listing is incorporated by reference into the specification for its disclosures.

BACKGROUND OF THE INVENTION

Polymerase chain reaction (PCR) is a technique widely used in molecular biology. It derives its name from one of its key components, a DNA polymerase used to amplify a piece of DNA by in vitro enzymatic replication. As PCR progresses, the DNA generated (the amplicon) is itself used as a template for replication. This sets in motion a chain reaction in which the DNA template is exponentially amplified. With PCR, it is possible to amplify a single or few copies of a piece of DNA across several orders of magnitude, generating millions or more copies of the DNA piece. PCR employs a thermostable polymerase, dNTPs, and a pair of primers.

PCR is conceptually divided into 3 reactions, each usually assumed to occur over time at each of three temperatures. Such an "equilibrium paradigm" of PCR is easy to understand in terms of three reactions (denaturation, annealing, and extension) occurring at 3 temperatures over 3 time periods each cycle. However, this equilibrium paradigm does not fit well with physical reality. Instantaneous temperature changes do not occur; it takes time to change the sample temperature. Furthermore, individual reaction rates vary with temperature, and once primer annealing occurs, polymerase extension immediately follows. More accurate, particularly for rapid PCR, is a kinetic paradigm where reaction rates and temperature are always changing. Holding the temperature constant during PCR is not necessary as long as the products denature and the primers anneal. Under the kinetic paradigm of PCR, product denaturation, primer annealing, and polymerase extension may temporally overlap and their rates continuously vary with temperature. Under the equilibrium paradigm, a cycle is defined by 3 temperatures each held for a time period, whereas the kinetic paradigm requires transition rates and target temperatures. Illustrative time/temperature profiles for the equilibrium and kinetic paradigms are shown in FIGS. 15a-15b. However, it is understood that these temperature profiles are illustrative only and that in some implementations of PCR, the annealing and extension steps are combined so that only 2 temperatures are needed.

Paradigms are not right or wrong, but they vary in their usefulness. The equilibrium paradigm is simple to understand and lends itself well to the engineering mindset and instrument manufacture. The kinetic paradigm is more relevant to biochemistry, rapid cycle PCR, and melting curve analysis.

When PCR was first popularized in the late 1980s, the process was slow. A typical protocol was 1 minute for denaturation at 94° C., 2 minutes for annealing at 55° C., and 3 minutes for extension at 72° C. When the time for transition between temperatures was included, 8 minute cycles were typical, resulting in completion of 30 cycles in 4 hours. Twenty-five percent of the cycling time was spent in temperature transitions. As cycling speeds increased, the proportion of time spent in temperature transitions also increased and the kinetic paradigm became more and more relevant. During rapid cycle PCR, the temperature is usually changing. For rapid cycle PCR of short products (<100 bps), 100% of the time may be spent in temperature transition and no holding times are necessary. For rapid cycle PCR of longer products, a temperature hold at an optimal extension temperature may be included.

In isolation, the term "rapid PCR" is both relative and vague. A 1 hour PCR is rapid compared to 4 hours, but slow compared to 15 minutes. Furthermore, PCR protocols can be made shorter if one starts with higher template concentrations or uses fewer cycles. A more specific measure is the time required for each cycle. Thus, "rapid cycle PCR" (or "rapid cycling") was defined in 1994 as 30 cycles completed in 10-30 minutes (1), resulting in cycles of 20-60 seconds each. This actual time of each cycle is longer than the sum of the times often programmed for denaturation, annealing and extension, as time is needed to ramp the temperatures between each of these stages. Initial work in the early 1990s established the feasibility of rapid cycling using capillary tubes and hot air for temperature control. Over the years, systems have become faster, and the kinetic requirements of denaturation, annealing, and extension have become clearer.

In one early rapid system, a heating element and fan from a hair dryer, a thermocouple, and PCR samples in capillary tubes were enclosed in a chamber (2). The fan created a rapid flow of heated air past the thermocouple and capillaries. By matching the thermal response of the thermocouple to the sample, the temperature of the thermocouple closely tracked the temperature of the samples, even during temperature changes. Although air has a low thermal conductivity, rapidly moving air against the large surface area exposed by the capillaries was adequate to cycle the sample between denaturation, annealing, and extension temperatures. Electronic controllers monitored the temperature, adjusted the power to the heating element, and provided the required timing and number of cycles. For cooling, the controller activated a solenoid that opened a portal to outside air, introducing cooling air to the otherwise closed chamber.

Temperatures could be rapidly changed using the capillary/air system. Using a low thermal mass chamber, circulating air, and samples in glass capillaries, PCR products >500 bp were visualized on ethidium bromide stained gels after only 10 minutes of PCR (30 cycles of 20 seconds each) (3). Product yield was affected by the extension time and the concentration of polymerase. With 30 second cycle times (about 10 seconds between 70 and 80° C. for extension), the band intensity increased as the polymerase concentration was increased from 0.1 to 0.8 Units per 10 µl reaction. It is noted that polymerase Unit definitions can be confusing. For native Taq polymerase, 0.4 U/10 μl is about 1.5 nM under typical rapid cycling conditions (50).

Rapid protocols use momentary or "0" second holds at the denaturation and annealing temperatures. That is, the temperature-time profiles show temperature spikes for denaturation and annealing, without holding the top and bottom temperatures. Denaturation and annealing can occur very quickly.

Rapid and accurate control of temperature allowed analytical study of the required temperatures and times for PCR. For an illustrative 536 bp fragment of human genomic DNA (β-globin), denaturation temperatures between 91° C. and 97° C. were equally effective, as were denaturation times from <1 second to 16 seconds. However, it was found that denaturation times longer than 16 seconds actually decreased product yield. Specific products in good yield were obtained with annealing temperatures of 50-60° C., as long as the time for primer annealing was limited. That is, best specificity was obtained by rapid cooling from denaturation to annealing and an annealing time of <1 second. Yield was best at extension temperatures of 75-79° C., and increased with extension time up to about 40 seconds.

Conclusions from this early work were: 1) denaturation of PCR products is very rapid with no need to hold the denaturation temperature, 2) annealing of primers can occur very quickly and annealing temperature holds may not be necessary, and 3) the required extension time depends on PCR product length and polymerase concentration. Also, rapid cycle PCR is not only faster, but better in terms of specificity and yield (4, 5) as long as the temperature was controlled precisely. PCR speed is not limited by the available biochemistry, but by instrumentation that does not control the sample temperature closely or rapidly.

However, most current laboratory PCR instruments perform poorly with momentary denaturation and annealing times, and many don't even allow programming of "0" second holding periods. Time delays from thermal transfer through the walls of conical tubes, low surface area-to-volume ratios, and heating of large samples force most instruments to rely on extended times at denaturation and annealing to assure that the sample reaches the desired temperatures. With these time delays, the exact temperature vs time course becomes indefinite. The result is limited reproducibility within and high variability between commercial products (6). Many instruments show marked temperature variance during temperature transitions (7, 8). Undershoot and/or overshoot of temperature is a chronic problem that is seldom solved by attempted software prediction that depends on sample volume. Such difficulties are compounded by thermal properties of the instrument that may change with age.

Over time, conventional heat block instruments have become faster, with incremental improvements in "thin wall" tubes, more conductive heat distribution between samples, low thermal mass blocks and other "fast" modifications. Nevertheless, it is unusual for these systems to cycle rapidly enough to complete a cycle in less than 60 seconds. A few heat block systems can achieve <60 second cycles, usually restricted to 2-temperature cycling between a limited range of temperatures. By flattening the sample container, rapid cycling can be achieved by resistive heating and air cooling (9), or by moving the sample in a flexible tube between heating zones kept at a constant temperature (U.S. Pat. No. 6,706,617).

Commercial versions of the air/capillary system for PCR have been available since 1991 (1) and for real-time PCR since 1996 (10, 11). Rapid cycling capabilities of other instruments are often compared against the air/capillary standard that first demonstrated 20-60 second cycles. Oddly enough, there has been a trend to run the capillary/air systems slower over the years, perhaps reflecting discomfort with "0" second denaturation and annealing times by many users. Also, heat-activated enzymes require long activation periods, often doubling run times even when "fast" activation enzymes are used. Another compromise away from rapid cycling is the use of plastic capillaries. These capillaries are not thermally matched to the instrument, so 20 second holds at denaturation and annealing are often required to reach the target temperatures (12).

Some progress in further decreasing the cycle times for PCR has occurred in microsystems, where small volumes are naturally processed (13, 14). However, even with high surface area-to-volume sample chambers, cycles may be long if the heating element has a high thermal mass and is external to the chamber (15). With thin film resistive heaters and temperature sensors close to the samples, 10-30 minute amplification can be achieved (16, 17).

While cooling of low thermal mass systems is usually by passive thermal diffusion and/or by forced air, several interesting heating methods have been developed. Infrared radiation can be used for heating (18) with calibrated infrared pyrometry for temperature monitoring (19). Alternatively, thin metal films on glass capillaries can serve as both a resistive heating element and a temperature sensor for rapid cycling (20). Finally, direct Joule heating and temperature monitoring of the PCR solution by electrolytic resistance is possible and has been implemented in capillaries (21). All of the above methods transfer heat to and from fixed samples.

Instead of heat transfer to and from stationary samples, the samples can be physically moved to different temperature baths, or through channels with fixed temperature zones. Microfluidic methods have become popular, with the PCR fluid passing within channels through different segments kept at denaturation, annealing, and extension temperatures. Continuous flow PCR has been demonstrated within serpentine channels that pass back and forth through 3 temperature zones (22) and within loops of increasing or decreasing radius that pass through 3 temperature sectors (23). A variant with a serpentine layout uses stationary thermal gradients instead of isothermal zones, to more closely fit the kinetic paradigm of PCR (24). To limit the length of the microchannel necessary for PCR, some systems shuttle samples back and forth between temperature zones by bi-directional pressure-driven flow (25), pneumatics (26), or electrokinetic forces (27). Instead of linear shuttling of samples, a single circular channel can be used with sample movement driven as a magnetic ferrofluid (28) or by convection (29). One potential advantage of microsystem PCR, including continuous flow methods, is cycling speed.

Although some microsystems still require >60 second cycles, many operate in the 20-60 second cycle range of rapid cycle PCR (13, 30). Minimum cycle times ranging from 16-37 seconds have been reported for infrared heating (18, 19). Metal coated capillaries have achieved 40 second PCR cycles (20), while direct electrolytic heating has amplified with 21 second cycles (20). Minimum cycle times reported for closed loop convective PCR range from 24-42 seconds (29, 31). Several groups have focused on reducing PCR cycle times to <20 seconds, faster than the original definition of rapid cycle PCR that was first demonstrated in 1990. Thin film resistive heating of stationary samples has reduced cycle times down to 17 seconds for 25 μl samples

(32) and 8.5 seconds for 100 nl samples (17). Continuous flow systems have achieved 12-14 second cycles with thermal gradient PCR (24) and sample shuttling (26), while a ferrofluid loop claims successful PCR with 9 second cycles (28). Continuous flow systems through glass and plastic substrates have achieved cycle times of 6.9 seconds (22) and 5.2 seconds (23) for various size PCR products. Alternating hot and cool water conduction through an aluminum substrate amplified 1 µl droplets under oil with 5.25 second cycles (33). Similarly, water conduction through a porous copper block amplified 5 µl samples with 4.6 second cycles (34). A continuous flow device of 1 µl reaction plugs augmented by vapor pressure achieved 3 second cycles (35). Additionally, there are reports that claim to amplify an 85 bp fragment of the Stx bacteriophage of *E. coli* in capillaries with 2.7 second cycles by immersion of the capillaries in gallium sandwiched between Peltier elements (36). Alternatively, PCR amplification in capillaries cycled by pressurized hot and cool gases obtained 2.6 second cycles (48).

Table 1 summarizes work to minimize PCR cycle times to less than the 20 second cycles that originally defined "Rapid PCR". Over the past 20 years, new prototype instruments have been developed that incrementally improve cycling speed. However, practical PCR performance (efficiency and yield) is often poor. As a general rule, as cycles become increasingly shorter, claims for successful PCR correlate with lower complexity targets (bacteria, phage, multicopy plasmids, or even PCR products) that are used at higher starting concentrations (see, e.g., U.S. Pat. No. 6,210,882, wherein 5 ng of amplicon was used as the starting sample). Indeed, none of the studies listed in Table 1 with <20 second cycles used complex eukaryotic DNA such as human DNA. The starting copy number of template molecules is often very high (e.g., 180,000,000 copies of lambda phage/µl), so that little amplification is needed before success is claimed. Furthermore, the lack of no template controls in many studies raises questions regarding the validity of positive results, especially in an environment with high template concentrations. One instrument-oriented report focuses extensively on the design and modeling of the thermal cycling device, with a final brief PCR demonstration using a high concentration of a low complexity target. Heating and cooling rates (up to 175° C./s) have been reported based on modeling and measurements without PCR samples present (17).

TABLE 1

| Fastest Cycle Time (s) | [Template] (Copies/µl) | Template Form | Total [Primers] (nM) | Polymerase | [Polymerase] (nM) | Product Length (bp) |
|---|---|---|---|---|---|---|
| 20 | 1,600 | Human DNA | 1000 | 0.08 U/µl Taq | 3 | 536 |
| 12 | 40,000 | Lambda phage | 400 | 0.2 U/µl Taq | 7.5 | 500 |
| 12 | 1,000,000 | 230 bp PCR product | 1000 | 0.5 U/µl Taq | 19 | 230 |
| 9.25 | 4,700-470,000 | 18S rDNA (human genomic) | 1800 | Taq Gold | ? | 187 |
| 9 | 18,000,000 | Lambda phage | 2000 | 0.025 U/µl Taq | 0.94 | 500 |
| 8.5 | ? | cDNA | 1800 | ? | ? | 82 |
| 7.0 | 10,000,000 | 1 KB PCR product | 2000 | 0.25 U/µl Taq | 9.4 | 176 |
| 6.3 | 10,000 | Plasmids (*B. anthracis*) | 1200 | 0.05 U/µl Ex Taq HS | ? | 134 |
| 5.2/9.7 | 180,000,000 | Lambda phage | 400 | 0.07 U/µl Taq | 2.6 | 500/997 |
| 5.25 | 1,400,000 | *B. subtilis* (bacterial DNA) | 500 | 0.025 U/µl KOD plus | ? | 72 |
| 4.6 | 34,000 | *E. herbicola* (bacterial DNA) | 800 | 0.04 U/µl KAPA2G | 4 | 58/160 |
| 4.2 | 50[1] | *B. subtilis* (bacterial DNA) | ? | KOD plus | ? | 72 |
| 3.0 | 10,000 | Plasmids (*B. anthracis*) | 1200 | 0.05 U/µl Ex Taq HS | ? | 134 |
| 2.7 | ? | stx phage (*E. coli*) | ?[3] | KOD | ? | 85 |
| 2.6 | ?[4] | stx phage (*E. coli*) | ?[5] | 0.5 U/µl Taq | 19 | 85 |

| Fastest Cycle Time (s) | Quantification | Trend | Method | No Template Control? | Reference |
|---|---|---|---|---|---|
| 20 | Faint Gel Band | Increases with [Polymerase] | Capillary Air Cycling | No | 3 |
| 12 | Capillary Electrophoresis | ? | IR Heating, Pressurized Air Cooling | No | 56 |
| 12 | Good gel band | Dependent on cycle # and copy # | Continuous Flow | Yes | 55 |
| 9.25 | ? | ? | IR Heating of droplets in oil | No | 54 |
| 9 | OK gel band | Intensity increases with cycle time | Continuous Flow with a Ferrous Particle Plug | No | 28 |
| 8.5 | 80% efficiency | Decreasing efficiency at faster cycles | Micromachined cantilever | ? | 17 |
| 7.0 | 7% of control | 50% at 15 s cycles | Continuous Flow | Yes | 22 |
| 6.3 | 55% of control | ? | Plug Continuous Flow | Yes | 53 |

TABLE 1-continued

| | | | | | |
|---|---|---|---|---|---|
| 5.2/9.7 | Faint gel bands | Dependent on cycle times | Continuous Flow | No | 23 |
| 5.25 | 90% efficiency (SYBR) | Single run | Water pumped against aluminum plate | Yes | 33 |
| 4.6 | Faint gel bands | Yield increases with # cycles | Water pumped through porous copper | No | 31 |
| 4.2 | Cq = 33 (SYBR) | Higher copy # reduces Cq | IR laser | ?[2] | 51 |
| 3.0 | 15% of control | 80% at 7.5 s cycles | Constant flow with vapor pressure | Yes (5% signal) | 35 |
| 2.7 | Barely visible band | Decreasing yield from 3.06 s to 2.69 s cycles | Gallium transfer from Peltiers to capillaries | No | 36 |
| 2.6 | Very dim band | Constant from 2.8 to 2.6 s cycles | Pressurized gas and capillaries | No | 48 |

[1]Presumed single copy in a 20 nl droplet with Cq of 33 under SYBR Green monitoring, but no gel or melting analysis to confirm PCR product identity.
[2]A "Blank" sample was run, but it is not clear if this was a no template control.
[3]Article says [primer] is 0.5 mmol, patent application (US 2009/0275014 A1) says [primer] is 0.01-0.5 μM.
[4]Two pg *E. coli* DNA/μl, but copy number of phage in the DNA preparation is unknown.
[5]Dissertation says 0.5 μmol/10 μl (50 mM), patent (U.S. Pat. No. 6,472,186) says 50 pmol/10 μl (5 μM).

One way to decrease cycle time is to introduce variations to the PCR protocol to ease the temperature cycling requirements. Longer primers with higher Tms allow higher annealing temperatures. By limiting the product length and its Tm, denaturation temperatures can be lowered to just above the product Tm. In combination, higher annealing and lower denaturation temperatures decrease the temperature range required for successful amplification. Reducing 3-step cycling (denaturation, annealing, and extension) to 2-steps (denaturation and a combined annealing/extension step) also simplifies the temperature cycling requirements. Both decreased temperature range and 2-step cycling are typical for the studies in Table 1 with cycle times <20 seconds. Two-step cycling can, however, compromise polymerase extension rates if the combined annealing/extension step is performed at temperatures lower than the 70 to 80° C. temperature optimum where the polymerase is most active. Polymerase extension rates are log-linear with temperature until about 70-80° C., with a reported maximum of 60-120 bp/s (50).

Even with protocol variations, amplification efficiency and yield are often poor when cycle times are <20 seconds when compared to control reactions (22, 23). These efforts towards faster PCR appear dominated by engineering with little focus on the biochemistry. As cycle times decrease from 20 seconds towards 2 seconds, PCR yield decreases and finally disappears, reflecting a lack of robustness even with simple targets at high copy number.

The instrumentation in various references disclosed in Table 1 may be suitable for extremely fast PCR, if reaction conditions are compatible. As disclosed herein, a focus on increased concentrations of primers, polymerase, and Mg++ allows for "extreme PCR" (PCR with <20 second cycles (30 cycles in <10 min)), while retaining reaction robustness and yield.

SUMMARY OF THE INVENTION

In one aspect of the present invention a method for amplifying a target nucleic acid sequence in a biological sample during amplification is provided, the method comprising the steps of adding a thermostable polymerase and primers configured for amplification of the target nucleic acid sequence to the biological sample, wherein the polymerase is provided at a concentration of at least 0.5 μM and primers are each provided at a concentration of at least 2 and amplifying the target nucleic acid sequence by polymerase chain reaction by thermally cycling the biological sample between at least a denaturation temperature and an elongation temperature through a plurality of amplification cycles using an extreme temperature cycling profile wherein each cycle is completed in less than 20 seconds per cycle.

In another aspect of the invention, a method for amplifying a target nucleic acid sequence in a biological sample during amplification is provided, the method comprising the steps of adding a thermostable polymerase and primers configured for amplification of the target nucleic acid sequence to the biological sample, wherein the polymerase to primer ratio is (about 0.03 to about 0.4 polymerase):(total primer concentration), and the polymerase concentration is at least 0.5 μM; and amplifying the target nucleic acid sequence by polymerase chain reaction by thermally cycling the biological sample between at least a denaturation temperature and an elongation temperature through a plurality of amplification cycles using an extreme temperature cycling profile wherein each cycle is completed in less than 20 seconds.

In yet another aspect of this invention, a device for performing PCR is provided, comprising a sample container for holding a PCR sample, means for heating the sample, means for cooling the sample, and control means for repeatedly subjecting the sample container to the means for heating the sample and the means for cooling the sample to thermal cycle the sample at a ramp rate of at least 200° C./s. In still one more embodiment, kits for performing PCR on a target nucleic acid are provided, the kits comprising: dNTPs, a polymerase provided at a concentration of at least 0.5 and a pair of primers configured for amplifying the target nucleic acid, wherein the primers are each provided at a concentration of at least 2 μM.

Additional features of the present invention will become apparent to those skilled in the art upon consideration of the following detailed description of preferred embodiments exemplifying the best mode of carrying out the invention as presently perceived.

BRIEF DESCRIPTION OF THE FIGURES

FIG. 5b is the extreme PCR temperature trace used in FIG. 5a.

FIG. 5c shows negative derivative melting curves of the 4 μM Klentaq polymerase (KT POL) products from FIG. 5a.

FIG. 5d is an agarose gel showing results of extreme PCR using varying polymerase concentrations at 10 μM primer concentrations from FIG. 5a.

FIG. 6b is a gel of the PCR products produced by the extreme temperature cycles of FIG. 6a.

FIG. 12b is a gel of the PCR products shown in the negative derivative melting curves of FIG. 12a.

FIG. 13b is a gel of the PCR products shown in the negative derivative melting curves of FIG. 13a.

FIG. 14b is a gel of the PCR products shown in the negative derivative melting curves of FIG. 14a.

DETAILED DESCRIPTION

Figure 1A:
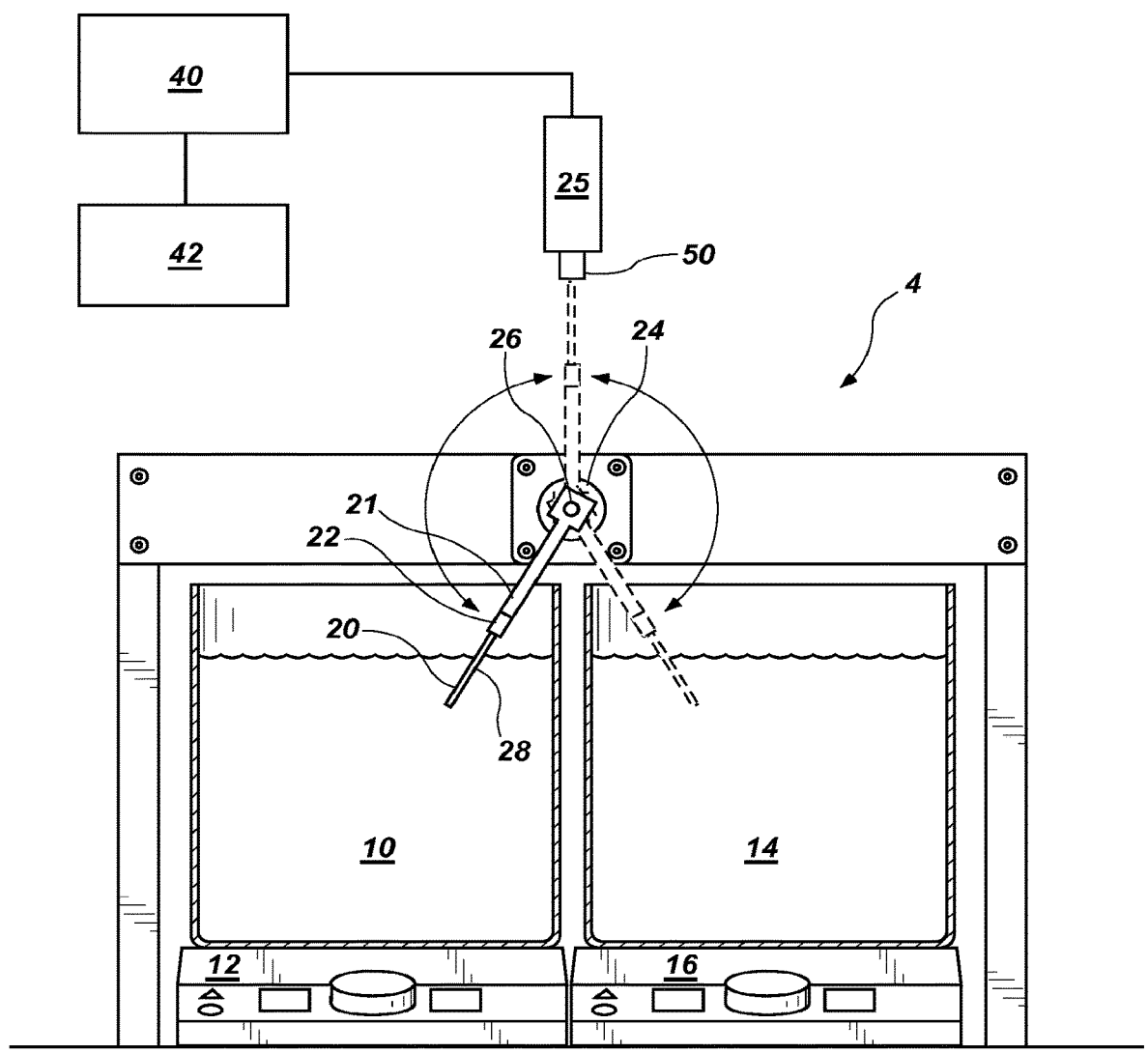
FIG. 1a shows a schematic for performing extreme PCR.

As used herein, the terms "a," "an," and "the" are defined to mean one or more and include the plural unless the context is inappropriate. Ranges may be expressed herein as from "about" one particular value, and/or to "about" another particular value. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 5%. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

The word "or" as used herein means any one member of a particular list and also includes any combination of members of that list.

By "sample" is meant an animal; a tissue or organ from an animal; a cell (either within a subject, taken directly from a subject, or a cell maintained in culture or from a cultured cell line); a cell lysate (or lysate fraction) or cell extract; a solution containing one or more molecules derived from a cell, cellular material, or viral material (e.g. a polypeptide or nucleic acid); or a solution containing a naturally or non-naturally occurring nucleic acid, which is assayed as described herein. A sample may also be any body fluid or excretion (for example, but not limited to, blood, urine, stool, saliva, tears, bile) that contains cells, cell components, or nucleic acids.

The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs (e.g., BrdU, dUTP, 7-deaza-dGTP), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA or any combination thereof.

By "probe," "primer," or "oligonucleotide" is meant a single-stranded DNA or RNA molecule of defined sequence that can base-pair to a second DNA or RNA molecule that contains a complementary sequence (the "target"). The stability of the resulting hybrid depends upon the length, GC content, nearest neighbor stacking energy, and the extent of the base-pairing that occurs. The extent of base-pairing is affected by parameters such as the degree of complementarity between the probe and target molecules and the degree of stringency of the hybridization conditions. The degree of hybridization stringency is affected by parameters such as temperature, salt concentration, and the concentration of organic molecules such as formamide, and is determined by methods known to one skilled in the art. Probes, primers, and oligonucleotides may be detectably-labeled, either radioactively, fluorescently, or non-radioactively, by methods well-known to those skilled in the art. dsDNA binding dyes (dyes that fluoresce more strongly when bound to double-stranded DNA than when bound to single-stranded DNA or free in solution) may be used to detect dsDNA. It is understood that a "primer" is specifically configured to be extended by a polymerase, whereas a "probe" or "oligonucleotide" may or may not be so configured.

By "specifically hybridizes" is meant that a probe, primer, or oligonucleotide recognizes and physically interacts (that is, base-pairs) with a substantially complementary nucleic acid (for example, a sample nucleic acid) under high stringency conditions, and does not substantially base pair with other nucleic acids.

By "high stringency conditions" is meant conditions that allow hybridization comparable with that resulting from the use of a DNA probe of at least 40 nucleotides in length, in a buffer containing 0.5 M NaHPO4, pH 7.2, 7% SDS, 1 mM EDTA, and 1% BSA (Fraction V), at a temperature of 65° C., or a buffer containing 48% formamide, 4.8×SSC, 0.2 M Tris-Cl, pH 7.6, 1×Denhardt's solution, 10% dextran sulfate, and 0.1% SDS, at a temperature of 42° C. Other conditions for high stringency hybridization, such as for PCR, northern, Southern, or in situ hybridization, DNA sequencing, etc., are well known by those skilled in the art of molecular biology (47).

In an illustrative embodiment, methods and kits are provided for PCR with <20 second cycle times, with some embodiments using <10 second, <5 second, <2 second, <1 second, and <0.5 second cycle times. With these cycle times, a 30 cycle PCR is completed in <10 min, <5 min, <2.5 min, <1 min, <30 seconds, and <15 seconds, respectively. As PCR speeds become increasingly faster, the primer and polymerase concentrations are increased, thereby retaining PCR efficiency and yield.

Compromising any of the 3 component reactions of PCR (primer annealing, polymerase extension, and template denaturation) can limit the efficiency and yield of PCR. For example, if primers anneal to only 95% of the template, the PCR efficiency cannot be greater than 95%, even if 100% of the templates are denatured and 100% of the primed templates are extended to full length products. Similarly, if extension is only 95% efficient, the maximum possible PCR efficiency is only 95%. In order for the PCR product concentration to double each cycle, all the components must reach 100% completion. Denaturation, annealing and extension will be considered sequentially in the following paragraphs.

Inadequate denaturation is a common reason for PCR failure, in slow (>60 second cycles), rapid (20-60 second cycles), and extreme (<20 second cycles) PCR temperature cycling. The goal is complete denaturation each cycle, providing quantitative template availability for primer annealing. Initial denaturation of template before PCR, particularly genomic DNA, usually requires more severe conditions than denaturation of the amplification product during PCR. The original optimization of rapid cycle PCR (4) was performed after boiling the template, a good way to assure initial denaturation of genomic DNA. Incomplete initial denaturation can occur with high Tm targets, particularly those with flanking regions of high stability (37). This can compromise quantitative PCR, illustratively for genomic insertions or deletions, particularly if minor temperature differences during denaturation affect PCR efficiency (37-39). If prior boiling or restriction digestion (37) is not desired, and higher denaturation temperatures compromise the polymerase, adjuvants that lower product Tm can be used to help with denaturation.

Although 94° C. is often used as a default target temperature for denaturation, it is seldom optimal. PCR products melt over a 40° C. range, depending primarily on GC content and length (43). Low denaturation target temperatures have both a speed and specificity advantage when the PCR product melts low enough that a lower denaturation temperature can be used. The lower the denaturation temperature, the faster the sample can reach the denaturation temperature, and the faster PCR can be performed. Added specificity arises from eliminating all potential products with higher denaturation temperatures, as these potential products will remain double-stranded and will not be available for primer annealing. To amplify high Tm products, the target temperature may need to be increased above 94° C. However, most current heat stable polymerases start to denature above 97° C. and the PCR solution may boil between 95 and 100° C., depending on the altitude, so there is not much room to increase the temperature. Lowering the monovalent salt and $Mg^{++}$ concentration lowers product Tm. Similarly, incorporating dUTP and/or 7-deaza-dGTP also lowers product Tm, but may decrease polymerase extension rates. Most proprietary PCR "enhancers" are simple organics that lower product Tm, enabling denaturation (and amplification) of high Tm products. Most popular among these are DMSO, betaine, glycerol, ethylene glycol, and formamide. In addition to lowering Tm, some of these additives also raise the boiling point of the PCR mixture (particularly useful at high altitudes). As the concentration of enhancer increases, product Tms decrease, but polymerase inhibition may increase.

Denaturation, however, need not be rate limiting even under extreme cycling conditions, because DNA unwinding is first order and very fast (10-100 msec), even when the temperature is only slightly above the product Tm. Denaturation occurs so rapidly at 2-3° C. above the Tm of the amplification product that it is difficult to measure, but complete denaturation of the amplicon probably occurs in less than 0.1 second. If the product melts in multiple domains, the target denaturation temperature should be 2-3° C. above the highest melting domain. As long as the sample reaches this temperature, denaturation is very fast, even for long products. Using capillaries and water baths (40), complete denaturation of PCR products over 20 kB occured in less than one second (52). Product Tms and melting domains are illustratively determined experimentally with DNA dyes and high resolution melting (41). Although Tm estimates can be obtained by software predictions (42), their accuracy is limited. Furthermore, observed Tms strongly depend on local reaction conditions, such as salt concentrations and the presence of any dyes and adjuvants. Thus, observed Tms are usually better matched to the reaction conditions.

Figure 2A:
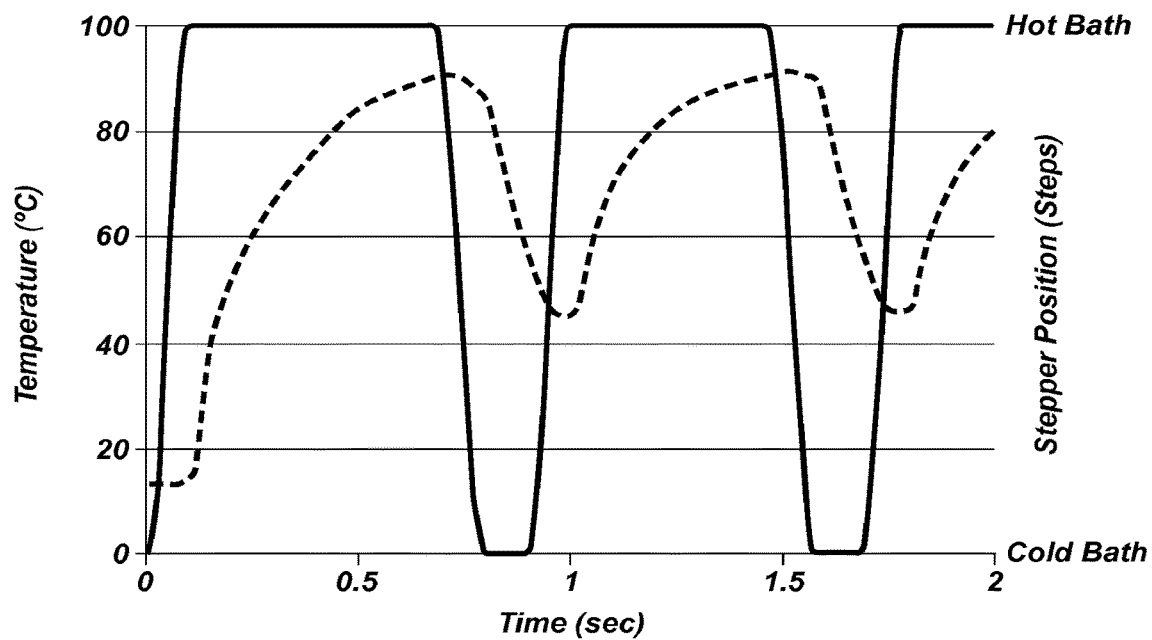
FIG. 2a is a graph that superimposes the location of the sample holder (-----) of FIG. 1b with the temperature of the sample (———).
Figure 6A:
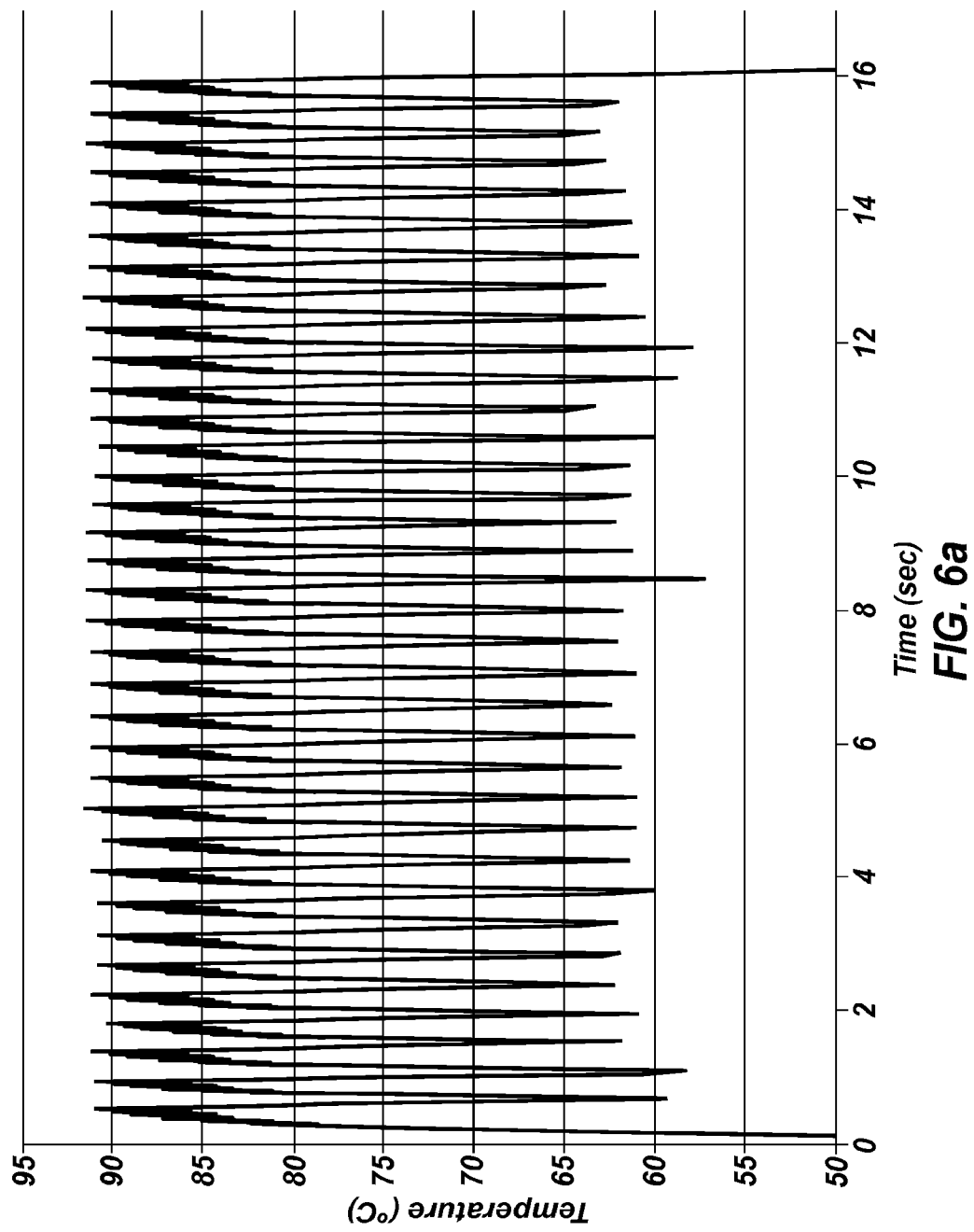
FIG. 6a is a temperature trace of extreme PCR performed in a 19 gauge stainless steel tube.

Without any effect on efficiency, the approach rate to denaturation can be as fast as possible, for example 200-400° C./s, as shown in FIGS. 2a and 6a. At these rates, only about 0.1-0.2 seconds are required to reach denaturation temperatures. However, a slower rate as the target temperature is approached decreases the risk of surpassing the target temperature and avoids possible polymerase inactivation or boiling of the solution. One illustrative method to achieve a slower approach temperature is to submerge the sample in a hot bath that exceeds the target temperature by 5-10° C. The temperature difference between the target and bath temperatures determines the exponential approach curve that automatically slows as the difference decreases. By continuously monitoring the temperature, the next phase (cooling toward annealing) is triggered when the denaturation target is achieved. In summary, complete product denaturation in PCR requires <0.2 s at temperatures 2-3° C. above the highest melting domain temperature of the product and the denaturation temperature can be approached as rapidly as possible, illustratively at 40-400° C./second. Since denaturation is first order, its rate depends only on the product concentration, and the efficiency (or percentage of the product that is denatured) is independent of the product concentration.

Incomplete and/or misdirected primer annealing can result in poor PCR. Low efficiency results if not all template sites are primed. Furthermore, if priming occurs at undesired sites, alternative products may be produced. The goal is essentially complete primer annealing to only the desired sites each cycle, providing quantitative primed template for polymerase extension.

Rapid PCR protocols with 20-60 second cycles suggest an annealing time of <1 second at 5° C. below the Tm of 500 nM primers (52). Primer concentrations for instruments attempting <20 second cycles range from 200-1,000 nM each (Table 1). These concentrations are similar to those used in conventional PCR (>60 second cycles), where long annealing times are used. Lowering the primer concentration is often used to improve specificity, and increasing the primer concentration is seldom considered due to concerns regarding nonspecific amplification. However, with rapid cycling, improved specificity has been attributed to shorter annealing times (5). If this trend is continued, one would expect that very short annealing times of extreme PCR should tolerate high primer concentrations. To promote annealing, an annealing temperature 5° C. below the primer Tm is recommended for 20-60 second cycles. Tms are best measured experimentally by melting analysis using saturating DNA dyes and oligonucleotides under the same buffer conditions used for amplification. The primer is combined with its complementary target with a 5'-extension as a dangling end, to best approximate the stability of a primer annealed to its template, and melting analysis is performed.

In contrast to denaturation, annealing efficiency depends on the primer concentration. Primer annealing can become limiting at very fast cycle speeds. Primer annealing is a second order reaction dependent on both primer and target concentrations. However, during most of PCR, the primer concentration is much higher than the target concentration and annealing is effectively pseudo-first order and dependent only on the primer concentration. In this case, the fraction of product that is primed (the annealing efficiency) depends only on the primer concentration, not the product concentration, so that higher primer concentrations should allow for shorter annealing times. Furthermore, without being bound to theory, it is believed that the relationship is linear. As the annealing time becomes shorter and shorter, increased primer concentrations become necessary to maintain the efficiency and yield of PCR. For example, rapid cycling allows about 1-3 seconds for annealing at temperatures 5° C. below primer Tm (3). If this annealing time (at or below Tm-5° C.) is reduced 10-fold in extreme PCR, a similar priming efficiency would be expected if the primer concentration were increased 10-fold. As the available annealing time becomes increasingly shorter, the primer concentration should be made increasingly higher by approximately the same multiple. Typical rapid PCR protocols use 500 nM each primer. If the annealing time in extreme PCR is reduced 3 to 40-fold, the primer concentrations required to obtain the same priming efficiency are 1,500-20,000 nM each primer. This is equivalent to 3,000-40,000 nM total primers, higher than any primer concentration in Table 1. This suggests that one reason for poor efficiency in prior attempts at <20 second cycling is poor annealing efficiency secondary to inadequate primer concentrations. In extreme PCR, the primer concentrations are increased to 1.5-20 µM each to obtain excellent annealing efficiency despite annealing times of 0.05-0.3 seconds. Ever greater primer concentrations can be contemplated for ever shorter annealing times, using increased primer concentrations to offset decreased annealing times to obtain the same annealing efficiency. It is noted that most commercial instruments require a hold time of at least 1 second, while a few instruments allow a hold time of "0" seconds, but no commercial instrument allows a hold time of a fractional second. For some illustrative examples of extreme PCR, hold times in increments of 0.1 or 0.01 seconds may be desirable.

Another way to increase the annealing rate and shorten annealing times without compromising efficiency is to increase the $Mg^{++}$ concentration. Annealing rates are known in the art to increase with increasing ionic strength, and divalent cations are particularly effective for increasing rates of hybridization, including primer annealing.

Illustratively, the approach rate to the annealing target temperature may be as fast as possible. For example, at 200-800° C./s (FIGS. 2a and 6a), annealing temperatures can be reached in 0.05-0.2 seconds. Rapid cooling also minimizes full length product rehybridization. To the extent that duplex amplification product forms during cooling, PCR efficiency is reduced because primers cannot anneal to the duplex product. Although this is rare early in PCR, as the product concentration increases, more and more duplex forms during cooling. Continuous monitoring with SYBR® Green I suggests that such product reannealing can be a major cause of the PCR plateau (44).

Polymerase extension also requires time and can limit PCR efficiency when extension times are short. Longer products are known to require longer extension times during PCR and a final extension of several minutes is often appended at the end of PCR, presumably to complete extension of all products. The usual approach for long products is to lengthen the time for extension. Using lower extension temperatures further increases required times, as in some cases of 2-step cycling where primer annealing and polymerase extension are performed at the same temperature.

Essentially complete extension of the primed template each cycle is required for optimal PCR efficiency. Most polymerase extension rates increase with temperature, up to a certain maximum. For Taq polymerase, the maximum is about 100 nucleotides/s at 75-80° C. and it decreases about 4-fold for each 10° C. that the temperature is reduced (50). For a 536 bp beta-globin product, 76° C. was found optimal in rapid cycle PCR (4). Faster polymerases have recently been introduced with commercial claims that they can reduce overall PCR times, suggesting that they may be able to eliminate or shorten extension holding times for longer products.

As an alternative or complement to faster polymerase extension rates, it has been found that increasing the concentration of polymerase reduces the required extension time. Given a standard Taq polymerase concentration in PCR (0.04 U/µl) or 1.5 nM (49) with 500 nM of each primer, if each primer is attached to a template, there is only enough polymerase to extend 0.15% of the templates at a time, requiring recycling of the polymerase over and over again to new primed templates in order to extend them all. By increasing the concentration of polymerase, more of the available primed templates are extended simultaneously, decreasing the time required to extend all the templates, presumably not by faster extension rates, but by extending a greater proportion of the primed templates at any given time.

To a first approximation, for small PCR products (<100 bp), the required polymerization time appears to be directly proportional to the polymerization rate of the enzyme (itself a function of temperature) and the polymerase concentration. The required time is also inversely proportional to the length of template to be extended (product length minus the primer length). By increasing the polymerase activity 20-300 fold over the standard activity of 0.04 U/µl in the PCR, extreme PCR with <20 second cycles can result in high yields of specific products. That is, activities of 0.8-12 U/µl (1-16 µM of KlenTaq) enable two-step extreme PCR with combined annealing/extension times of 0.1-1.0 second. The highest polymerase activity used previously was 0.5 U/µl (Table 1). For two-step PCR that is used in illustrative examples of extreme PCR, a combined annealing/extension step at 70-75° C. is advantageous for faster polymerization rates. Furthermore, because it simplifies temperature cycling, two-step PCR is typically used in illustrative examples of extreme cycling (<20 second cycles) and both rapid annealing and rapid extension must occur during the combined annealing/extension step. Therefore, both increased primer concentrations and increased polymerase concentrations are used in illustrative examples, resulting in robust PCR under extreme two-temperature cycling. Illustratively, primer concentrations of 1.5-20 µM each and polymerase concentrations of 0.4-12 U/µl of any standard polymerase (0.5-16 µM of KlenTaq) are necessary with combined annealing/extension times of 0.05-5.0 seconds at 50-75° C., as illustrated in the Examples to follow. Because there is only one PCR cycling segment for both annealing and extension, extreme PCR conditions require enhancement of both processes, illustratively by increasing the concentrations of both the primers and the polymerase.

Extreme three-temperature cycling is also envisioned, where the annealing and extension steps are kept separate at different temperatures. In this case, the time allotted to annealing and extension steps can be individually controlled and tailored to specific needs. For example, if only the annealing time is short (0.05-0.2 seconds) and the extension time is kept comparatively long (illustratively for 1, 2, 5, 10 or 15 seconds), only the primer concentrations need to be increased for efficient PCR. Alternatively, if the extension time is short (<1 sec within 70-80° C.), but the annealing time is long, it is believed that only the polymerase concentration needs to be increased to obtain efficient PCR. It is understood that efficient PCR has an illustrative efficiency of at least 70%, more illustratively of at least 80%, and even at least 90%.

For products longer than 100 bp, efficient extension using extreme PCR may need a combination of high polymerase concentration and increased extension time. If the polymerase is in excess, the minimum time illustratively should be the extension length (defined as the product length minus the primer length) in bases divided by the polymerase extension rate in bases/second. However, as previously noted, the polymerase is usually only saturating in the beginning of PCR, before the concentration of template increases to greater than the concentration of polymerase. One way to decrease cycle time is to use two-temperature PCR near the temperature maximum of the polymerase, typically 70-80° C. The required extension time can be determined experimentally using real-time PCR and monitoring the quantification cycle or Cq. For example, at a polymerase extension rate of 100 bases/second at 75° C., a 200 bp product would be expected to require about 2 seconds if the concentration of polymerase is in excess. Similarly, a 400 bp product would be expected to require about 4 seconds using this same polymerase as long as its concentration is greater than the template being extended. If the polymerase is not in excess, adding more polymerase allows more templates to be extended at the same time, decreasing the required extension time in proportion to the concentration of polymerase.

The utility of any DNA analysis method depends on how fast it can be performed, how much information is obtained, and how difficult it is to do. Compared to conventional cloning techniques, PCR is fast and simple. Rapid cycle and extreme PCR focus on continued reduction of the time required. Real-time PCR increases the information content by acquiring data each cycle. Melting analysis can be performed during or after PCR to monitor DNA hybridization continuously as the temperature is increased.

Figure 15B:
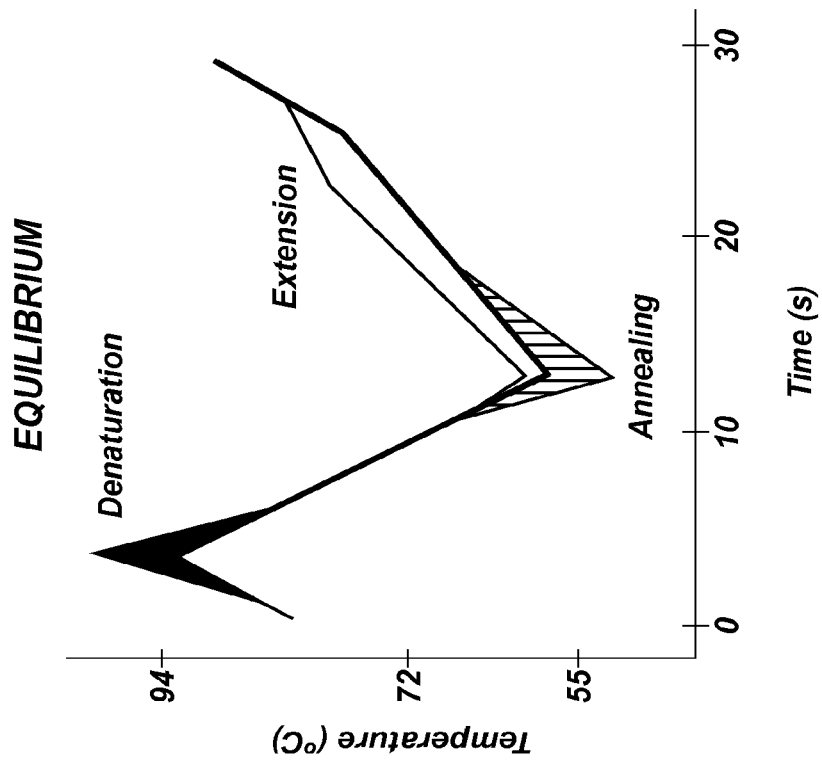
FIGS. 15a-15b show illustrative profiles for an equilibrium paradigm (FIG. 15a) and a kinetic paradigm (FIG. 15b) of PCR. Solid black represents denaturation, striped represents annealing, and solid white represents extension of the nucleic acids during thermal cycling.
Figure 15A:
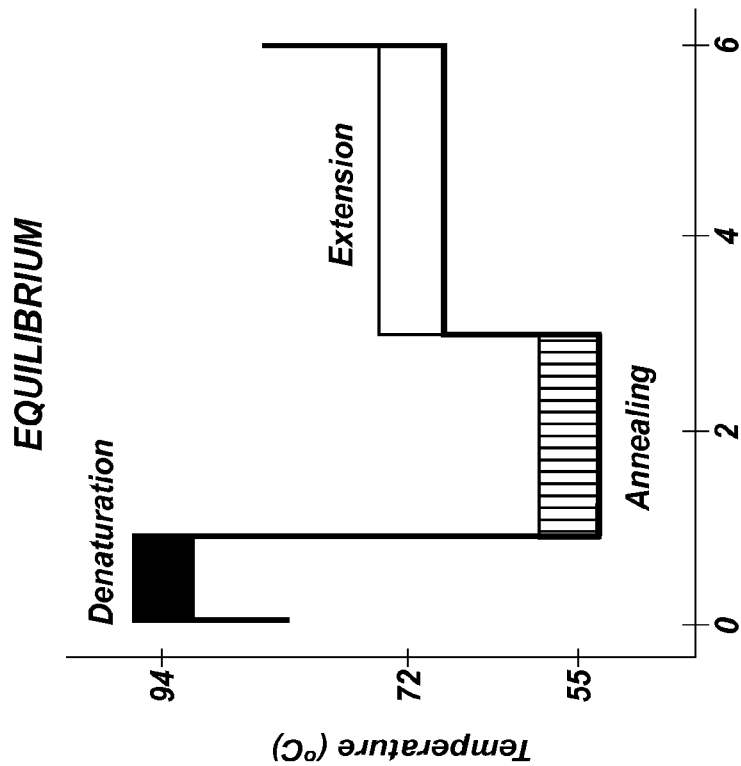

Returning to the equilibrium and kinetic paradigms of PCR (FIG. 15a-15b), extreme PCR of products <100 bps exemplifies a good application of the kinetic model. Temperatures are always changing and rates of denaturation, annealing, and extension depend on temperature, so an adequate assessment of PCR can only be obtained by integrating the rates of the component reactions across temperature. For products greater than 100 bp, longer extension times may be necessary, and components of both the kinetic and equilibrium models are appropriate.

When the reaction conditions are configured according to at least one embodiment herein, it has been found that PCR can be performed at very fast rates, illustratively with some embodiments in less than one minute for complete amplification, with cycle times of less than two seconds. Illustratively, various combinations of increased polymerase and primer concentrations are used for this extreme PCR. Without being bound to any particular theory, it is believed that an excess concentration of primers will allow for generally complete primer annealing, thereby increasing PCR efficiency. Also without being bound to any particular theory, it is believed that an increase in polymerase concentration improves PCR efficiency by allowing more complete extension. Increased polymerase concentration favors binding to the annealed primer, and also favors rebinding if a polymerase falls off prior to complete extension. The examples below show that extreme PCR has been successful, even when starting with complex eukaryotic genomic DNA.

Although KlenTaq was used in the Examples to follow, it is believed that any thermostable polymerase of similar activity will perform in a similar manner in extreme PCR, with allowances for polymerase extension rates. For example, Herculase, Kapa2G FAST, KOD Phusion, natural or cloned *Thermus aquaticus* polymerase, Platinum Taq, GoTaq and Fast Start are commercial preparation of polymerases that should enable extreme PCR when used at the increased concentrations presented here, illustratively adjusted for differences in enzyme activity rates.

Because no current commercial PCR instrument allows for two second cycle times, a system 4 was set up to test proof of concept for extreme PCR. However, it is understood that the system 4 is illustrative and other systems that can thermocycle rapidly are within the scope of this disclosure. As shown in FIG. 1a, a hot water bath 10 of 95.5° C. (the temperature of boiling water in Salt Lake City, Utah, the location where the present examples were performed), and a cool water bath 14 of 30-60° C. are used to change the temperature of 1-5 µl samples contained in a sample container 20. The illustrative water baths 10, 14 are 4.5 quart stainless steel dressing jars (Lab Safety Supply, #41634), although 500 ml glass beakers were used in some examples, and are heated on electric hotplates 12, 16 with magnetic stirring (Fisher Scientific Isotemp Digital Hotplates (#11-300-49SHP). However, it is understood that other embodiments may be used to heat and cool the samples. In the embodiment shown in FIG. 1a, the sample container 20 is a composite glass/plastic reaction tube (BioFire Diagnostics #1720, 0.8 mm ID and 1.0 mm OD). However, in other examples, hypodermic needles (Becton Dickenson #305187, 0.042" ID, 0.075" OD) and composite stainless steel/plastic reaction tubes constructed from stainless steel tubing (Small Parts, 0.042" ID/0.075" OD, 0.035" ID/0.042" OD, or 0.0265" ID/0.035" OD) and fit into the plastic tops of the BioFire tubes were used as the sample container 20. While other sample containers are within the scope of this invention, it is desirable that the sample containers have a large surface area to volume ratio and have a fast heat transfer rate. For certain embodiments, the open end of the metal tubing was sealed by heating to a red-white color using a gas flame and compressing in a vise. For real-time PCR, tubes that are optically clear or have an optically clear portion are desirable. Samples were spun down to the bottom of each tube by brief centrifugation.

The sample container 20 is held by a tube holder 22 attached to a stepper motor shaft 26 by arm 21. The tube holder 22 was machined from black Delrin plastic to hold 2-5 sample containers 20 (only one sample container 20 is visible in FIG. 1a, but a row of such sample containers 20 may be present) so that the reaction solutions were held at a radius of 6.5-7.5 cm. While not visible in FIG. 1a, a thermocouple (Omega type T precision fine wire thermocouple #5SRTC-TT-T-40-36, 36" lead, 0.003' diameter with Teflon insulation) may be used to measure temperature. With reference to FIG. 1d, which shows a similar tube holder and arm of FIG. 1b with like numbers representing similar components, a tube holder 222 designed to hold two sample containers is present, with one location in tube holder 222 occupied by a thermocouple 228. It is understood that any number of sample containers 20 or 220 may be used in any of the embodiments described herein, with or without a thermocouple, as shown in FIG. 1d. Thermocouple amplification and linearization is performed with an Analog Devices AD595 chip (not shown). The thermocouple voltage was first calculated from the AD595 output as Type T voltage=(AD595 output/247.3)-11 µV. Then the thermocouple voltage was converted to temperature using National Institute of Standards and Technology coefficients for the voltage/temperature correlation of Type T thermocouples. The analog signal was digitized (PCIe-6363 acquisition board) and processed by LabView software (version 2010, National Instruments) installed on CPU 40 and viewed on user interface 42. Stepper motion illustratively is triggered dynamically at 87-92° C. and 60-75° C. or may be held in each water bath for a computer-controlled period of time. Thirty to fifty cycles are typically performed.

The stepper motor 24 (Applied Motion Products, #HT23-401, 3V, 3A) is positioned between the water baths 10 and 14 so that all sample containers 20 in the tube holder 22 could flip between each water bath 10 and 14, so that the portion of each sample container 20 containing samples are completely submerged. The stepper motor 24 is powered illustratively by a 4SX-411 nuDrive (National Instruments, not shown) and controlled with a PCI-7344 motion controller and NI-Motion Software (version 8.2, National Instruments) installed on CPU 40. Stepper motor 24 rotates between water baths 10 and 14 in about 0.1 second. FIG. 2a shows a sample temperature trace (———) juxtaposed over a trace of the position of the sample container 20 (-----) for a run where stepper motion was triggered at 90° C. and 50° C. As can be seen in FIG. 2, there is some overshoot to a temperature lower than 50° C., presumably due do the time required to move the sample container 20 out of water bath 14. Thus, as discussed above, it may be desirable to trigger stepper motor 24 at a somewhat higher temperature. In the examples below, the temperatures given are for the sample temperature reached, not the trigger temperature. The maximum heating rate calculated from FIG. 2a is 385° C./s and maximum cooling rate 333° C./s. Illustratively, extreme PCR may be performed with ramp rates of at least 200° C./s. In other embodiments, the ramp rate may be 300° C./s or greater.

In some examples, system 4 is also configured for real-time monitoring. As shown in FIG. 1a, for real time monitoring, a fiber optics tip 50 of optics block 25 is mounted above sample container 20, such that when sample container 20 is being moved from hot water bath 10 to the cold water bath by stepper motor 24, sample container 20 passes by the fiber optics tip 50, with or without a hold in this monitoring position. In this illustrative embodiment, fiber optics tip is provided in air above the water baths. Thermocycling device 4 may be controlled by CPU 40 and viewed on user interface 42

Figure 1B:
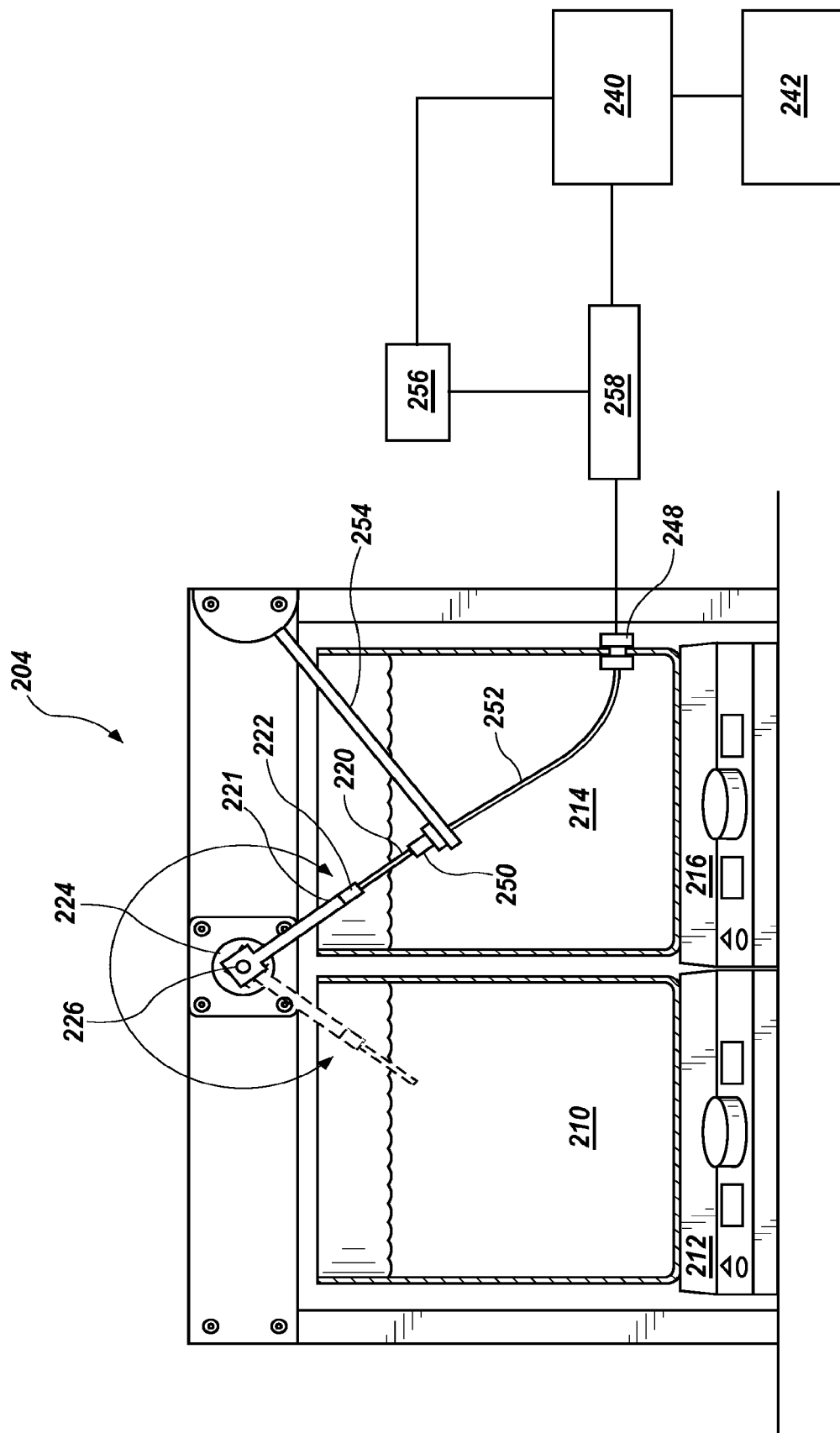
FIG. 1b is an illustrative device for performing extreme PCR with real-time capabilities for monitoring one sample tube in a water bath.

FIG. 1*b* shows an embodiment similar to FIG. 1*a*. Hot plates 212 and 216 are provided for controlling temperature of hot water bath 210 and cold water bath 214. A stepper motor 224 is provided for moving sample container 220 and thermocouple 228 (shown in FIG. 1*d*), by moving arm 221 and tube holder 222, which is illustratively made of aluminum. However, in this embodiment, the tip 250 of the fiber optics cable 252 is held in water bath 214 by positioning block 254. Fiber optics cable 252 enters water bath 214 through port 248 and provides signal to optics block 225. Thermocycling device 204 may be controlled by CPU 240 and viewed on user interface 242

Light from an Ocean Optics LLS-455 LED Light Source 256 was guided by fiber optics cable 252 (Ocean Optics P600-2-UV-VIS, 600 µm fiber core diameter) into a Hamamatsu Optics Block 258 with a 440+/−20 nm excitation interference filter, a beamsplitting 458 nm dichroic and a 490+/−5 nm emission filter (all from Semrock, not shown). Epifluorescent illumination of the capillary was achieved with another fiber optic cable (not shown) placed approximately 1-2 mm distant from and in-line with the one sample capillary when positioned in the cooler water bath. Emission detection was with a Hamamatsu PMT 62.

Figure 1C:
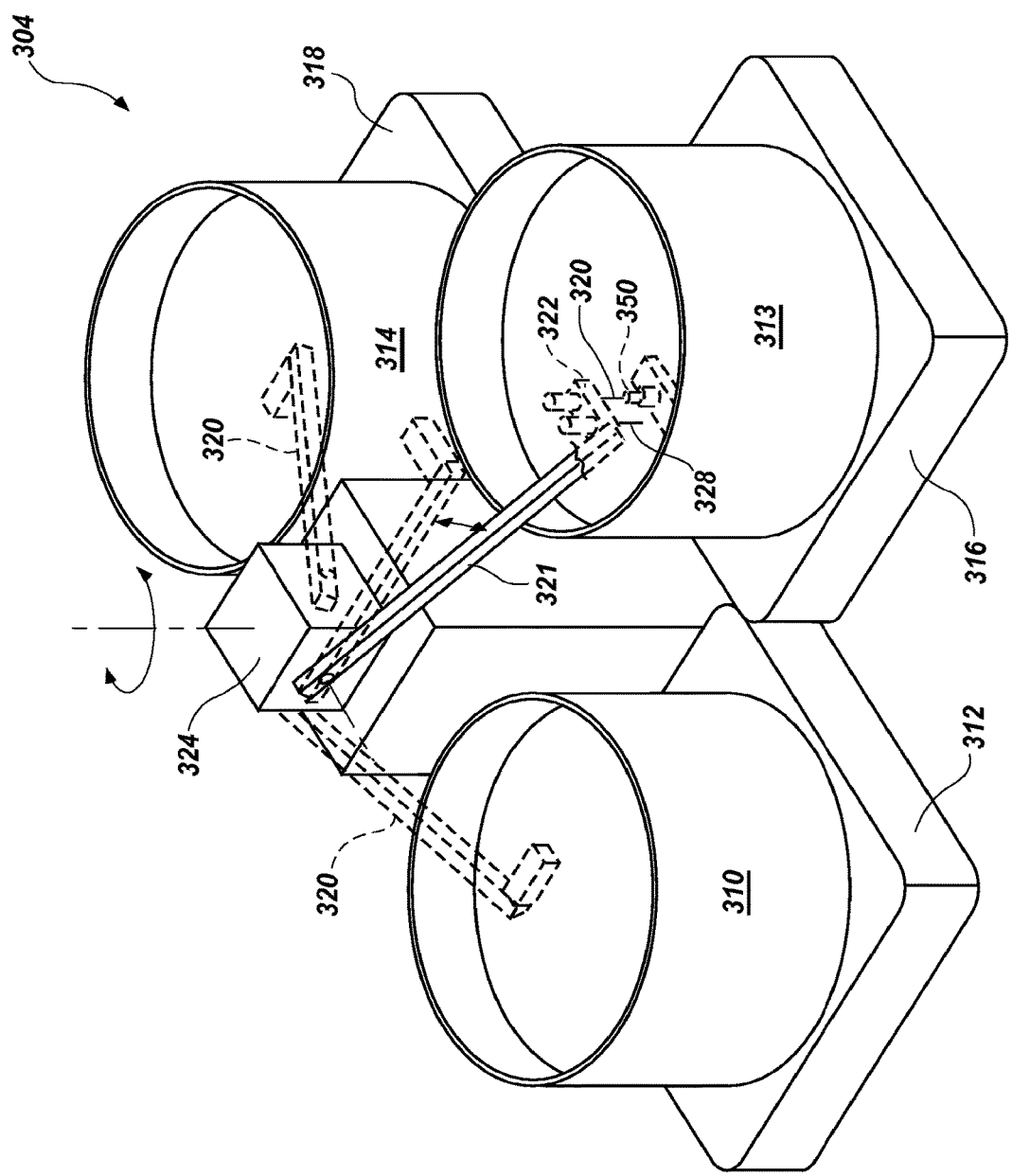
FIG. 1c is an illustrative device for performing extreme PCR with three-temperature cycling.
Figure 1D:
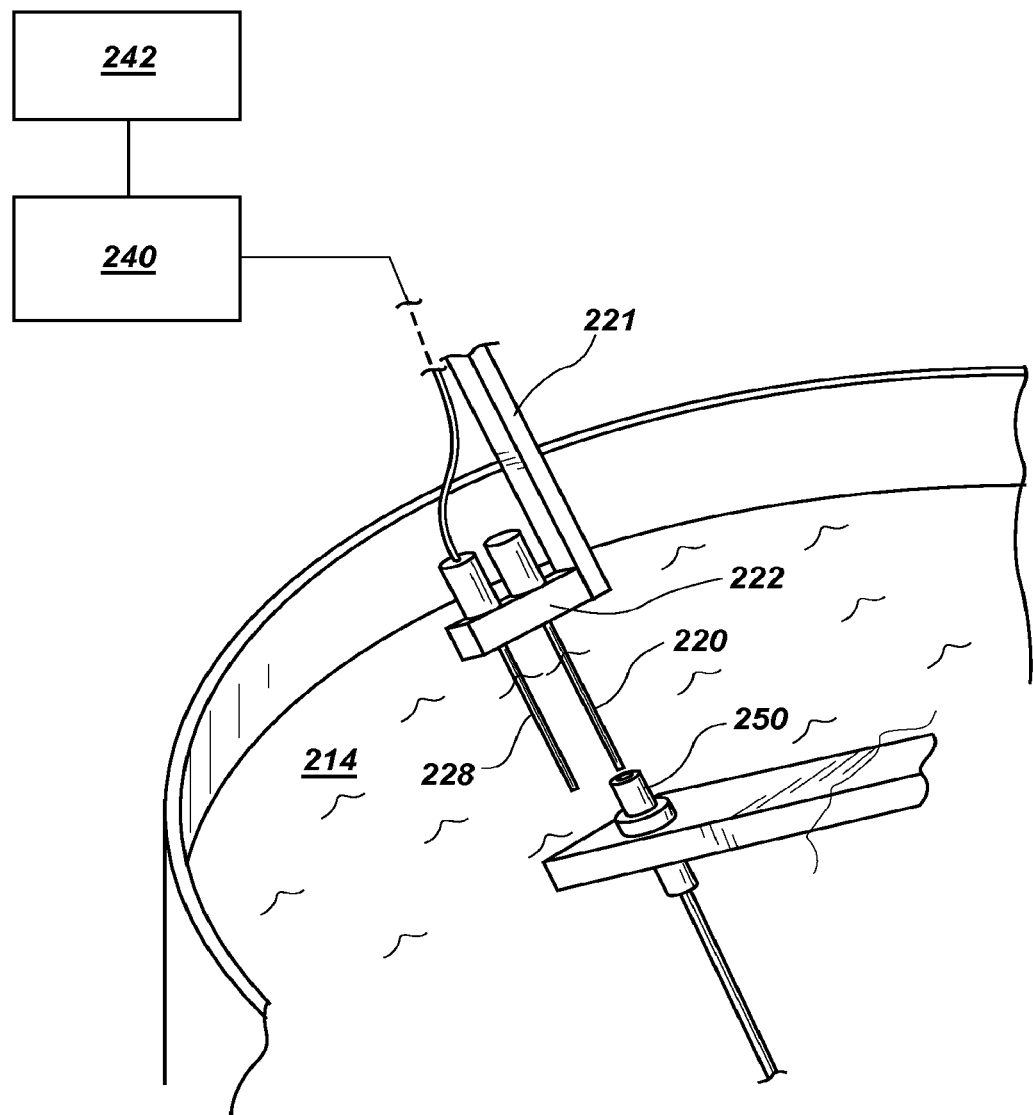
FIG. 1d is a close up view of the optics of the device in FIG. 1b that also shows the temperature reference capillary.

FIG. 1*c* shows an illustrative system 304 for three-temperature PCR. A hot water bath 310 of 95.5° C., a cool water bath 314 of 30-60° C., and a medium water bath 313 of 70-80° C. are used to change the temperature of 1-5 µl samples contained in a sample container 320, and are heated on three electric hotplates 312, 316, and 318 with magnetic stirring. The sample container 320 is held by a tube holder 322 attached to a stepper motor 324 by arm 321. Thermocouple 328 is also held by tube holder 322. Arm 321 may be raised as stepper motor 324 rotates. A fiber optics tip 350 is illustratively provided in medium water bath 313, although it is understood that it may be placed in air, as with FIG. 1*a*. Due to the set-up of this illustrative embodiment, it was not possible to place the three water baths, 310, 313, and 314 equidistant from one another. Accordingly, the largest space was placed between hot water bath 310 and cool water bath 314, as cooling of the sample between these baths is desirable, whereas the sample moves between the other water baths to be heated. However, it is understood that this configuration is illustrative only and that other configurations are within the spirit of this disclosure. Because two stepper motors are used simultaneously (one to raise the capillary out of the water and one to transfer between water baths) the angular motion of each can be minimized to decrease the time of movement between baths. In the 2 water bath system, the required angular motion of the stepper to transfer the sample between baths is greater than 270 degrees. However, in the 3 water bath system, the stepper motor that raises the samples needs to traverse less than 45 degrees while the stepper moving the samples between water baths needs to move only 90 degrees or less. The water baths can also be configured as sectors of a circle (pie-shaped wedges) to further limit the angular movement required. Minimizing the angular movement decreases the transfer time between water baths. Transfer times less than 100 msec or even less than 50 msec are envisioned. Other components of this system 304 are similar to the systems 4, 204 shown in FIGS. 1*a-b* and are not shown in FIG. 1*c*.

Example 1

Unless otherwise indicated, PCR was performed in 5 µl reaction volumes containing 50 mM Tris (pH 8.3, at 25° C.), 3 mM MgCl$_2$, 200 µM each dNTP (dATP, dCTP, dGTP, dTTP), 500 µg/ml non-acetylated bovine serum albumin (Sigma), 2% (v/v) glycerol (Sigma), 50 ng of purified human genomic DNA, and 1×LCGreen® Plus (BioFire Diagnostics). The concentration of the primers and the polymerase varied according to the specific experimental protocols. Klentaq™ DNA polymerase was obtained from either AB Peptides, St. Louis, Mo., or from Wayne Barnes at Washington University (St. Louis). The molecular weight of KlenTaq is 62.1 kD with an extinction coefficient at 280 nm of 69,130 M$^{-1}$cm$^{-1}$, as calculated from the sequence (U.S. Pat. No. 5,436,149). Mass spectrometry confirmed a predominate molecular weight of 62 kD, and denaturing polyacrylamide gels showed that the major band was greater than 80% pure by integration. Using the absorbance and purity to calculate the concentration indicated an 80 µM stock in 10% glycerol. Final polymerase concentrations were typically 0.25-16 µM. One µM KlenTaq is the equivalent of 0.75 U/µl, with a unit defined as 10 nmol of product synthesized in 30 min at 72° C. with activated salmon sperm DNA. Primers were synthesized by the University of Utah core facility, desalted, and concentrations determined by A$_{260}$. The final concentrations of each primer typically varied from 2.5-20 µM.

A 45 bp fragment of KCNE1 was amplified from human genomic DNA using primers CCCATTCAACGTCTA-CATCGAGTC (SEQ ID NO:1) and TCCTTCTCTTGCCAGGCAT (SEQ ID NO:2). The primers bracketed the variant rs #1805128 (c.253G>A) and amplified the sequence:

```
                                  (SEQ ID NO: 3)
CCCATTCAACGTCTACATCGAGTCC (G/A) ATGCCTGGCAAGAGAAGGA.
```

Figure 2B:
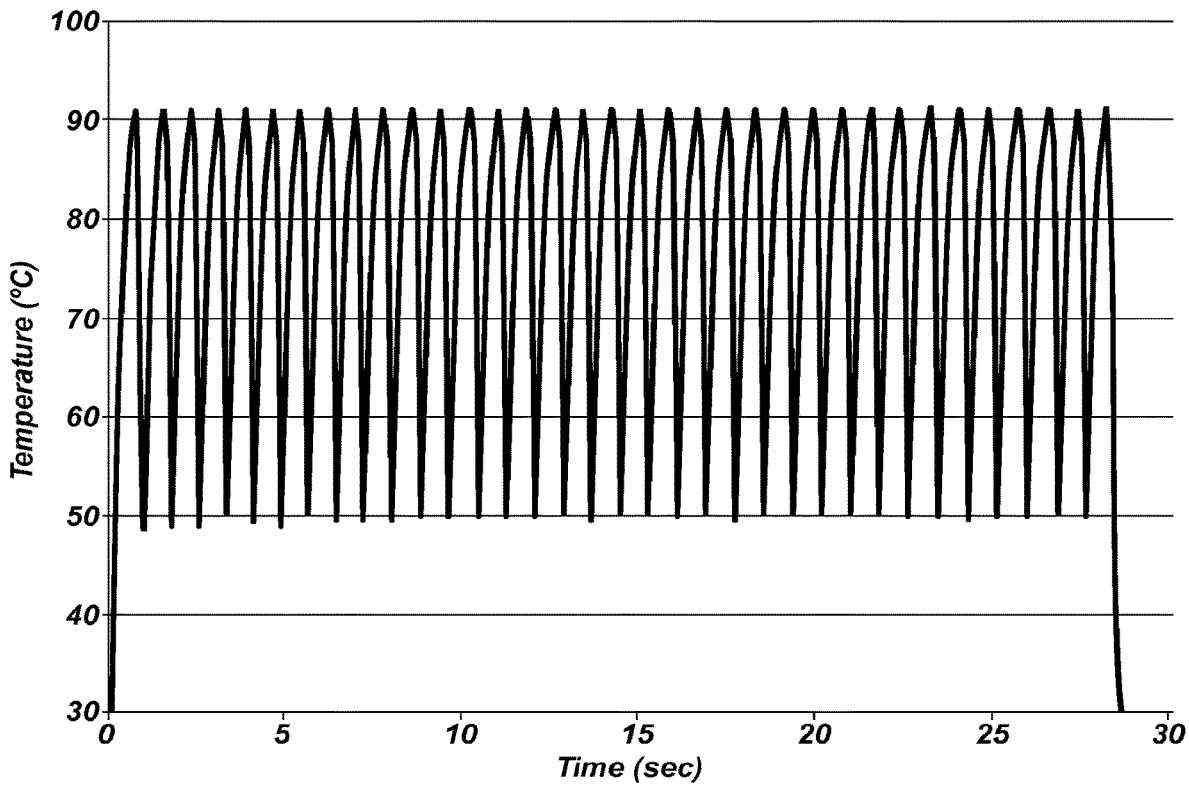
FIG. 2b is a temperature graph of extreme PCR using the device shown in FIG. 1b.
Figure 2C:
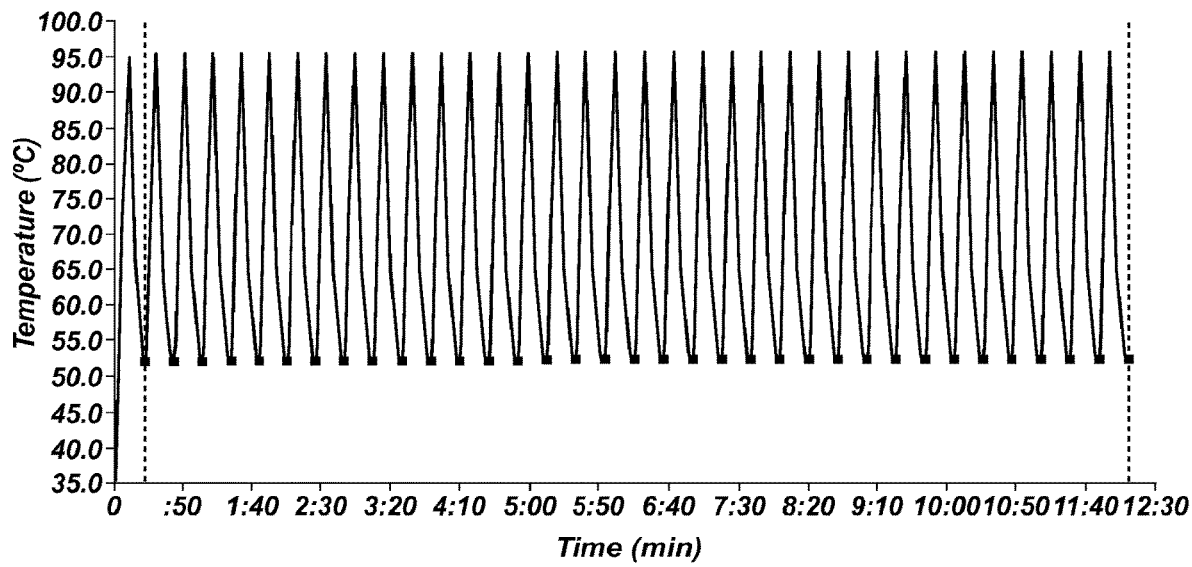
FIG. 2c is a temperature graph of rapid cycle PCR using a carousel LightCycler shown for comparison against FIG. 2b.
Figure 3A:
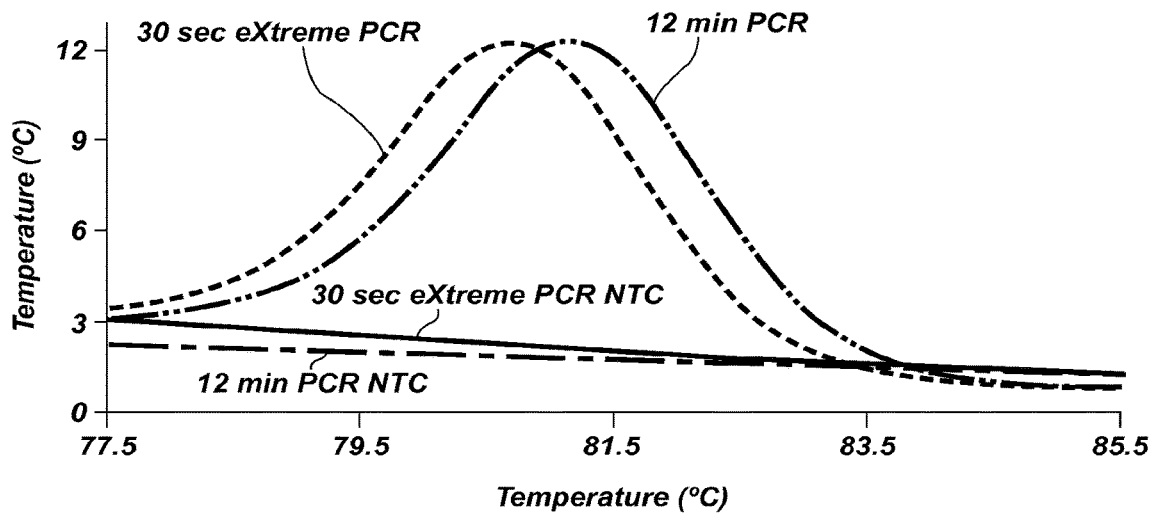
FIG. 3a shows derivative melting curves of extreme PCR products (-----) and rapid cycle PCR products (—··—), with negative controls for extreme (———) and rapid (—··—) —··—)cycling, amplified using the temperature profile of FIG. 2b.
Figure 3B:
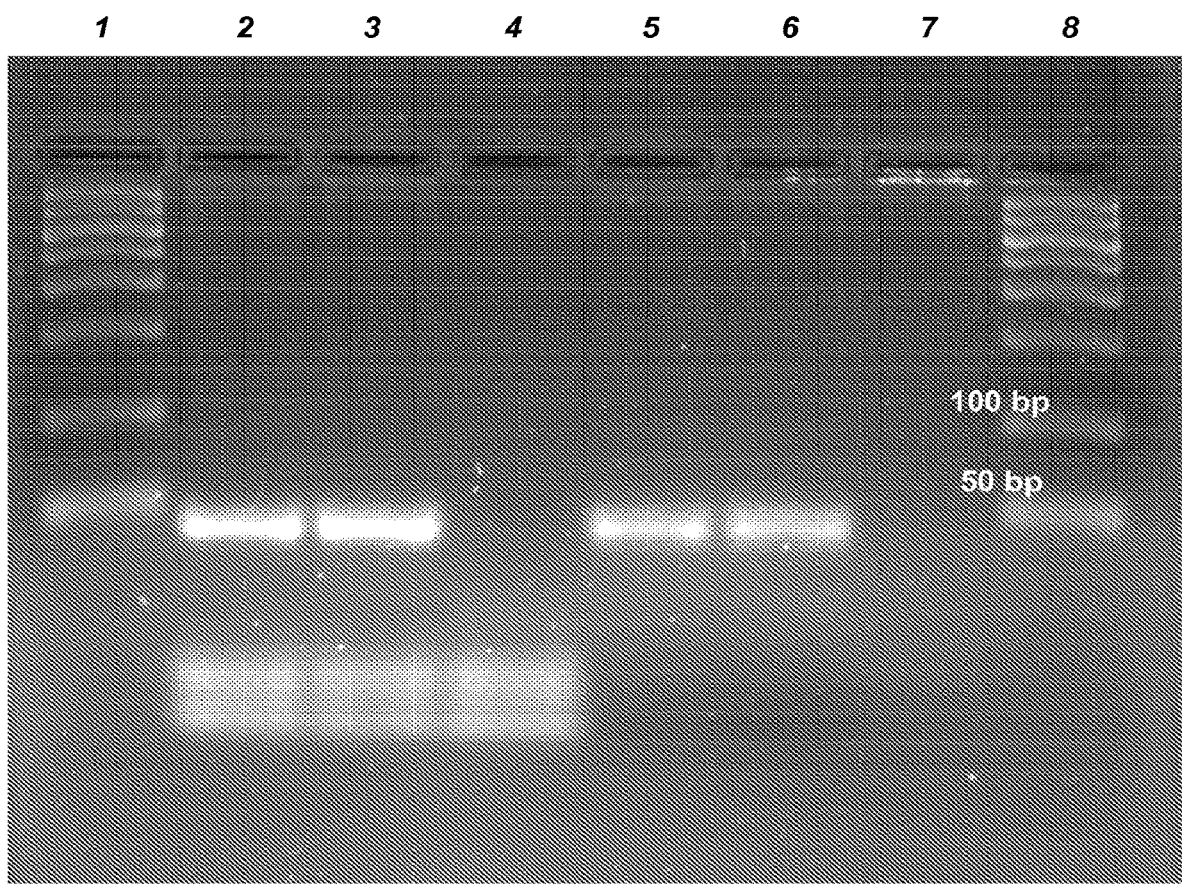
FIG. 3b is a 2% SeaKem LE agarose gel of the same samples of FIG. 3a, lanes 1 and 8 are size markers, lanes 2 and 3 are products resulting from 30 sec extreme PCR, lane 4 is a no template control for 30 sec extreme PCR, lanes 5 and 6 are products resulting from 12 min PCR, and lane 7 is the no template control for 12 min PCR.

FIG. 3*a* shows a melting curve of the PCR product generated by extreme PCR using the device shown in FIG. 1*a*, where 0.64 µM KlenTaq and 10 µM of each primer were used, and cycled between 91° C. and 50° C., as shown in FIG. 2*b*, for 35 cycles and a total amplification time of 28 seconds. Each cycle required 0.8 seconds. Also shown in FIG. 3*a* is a melting curve of the same amplicon generated by rapid cycling in the LightCycler, where 0.064 µM KlenTaq and 0.5 µM of each primer were used, and cycling was between 90° C. and 50° C. for 35 cycles and a total amplification time of 12 minutes (FIG. 2*c*). Each cycle required 10.3 seconds. Note that because of the different time scales in FIGS. 2*b* and 2*c*, the entire extreme PCR protocol of FIG. 2*b* is completed in less than 2 cycles of its rapid cycle counterpart. Both reactions produced amplicons having similar Tms and strong bands on gel electrophoresis (FIG. 3*b*), whereas neither negative control showed amplification by either melting analysis or gel electrophoresis. In this illustrative example, extreme PCR conditions showed greater yield than rapid cycle PCR conditions when analyzed on gels (FIG. 3*b*). The 0.5° C. difference in Tm on the melting curves is believed to be due to the different amounts of glycerol in each reaction, arising from the glycerol content in the polymerase storage buffer (final concentration of glycerol in the PCR was 1.3% under extreme conditions and 0.1% under rapid conditions). FIG. 3b also confirms that the size of the amplicons were similar and as predicted. In addition, despite the high concentrations of polymerase and primers, the reaction appears specific with no indication of nonspecific products. However, high resolution melting analysis was unable to distinguish the 3 genotypes. The stoichiometric percentage of polymerase to total primer concentration was 3% for extreme PCR and 6.4% for rapid cycle PCR.

Figure 3C:
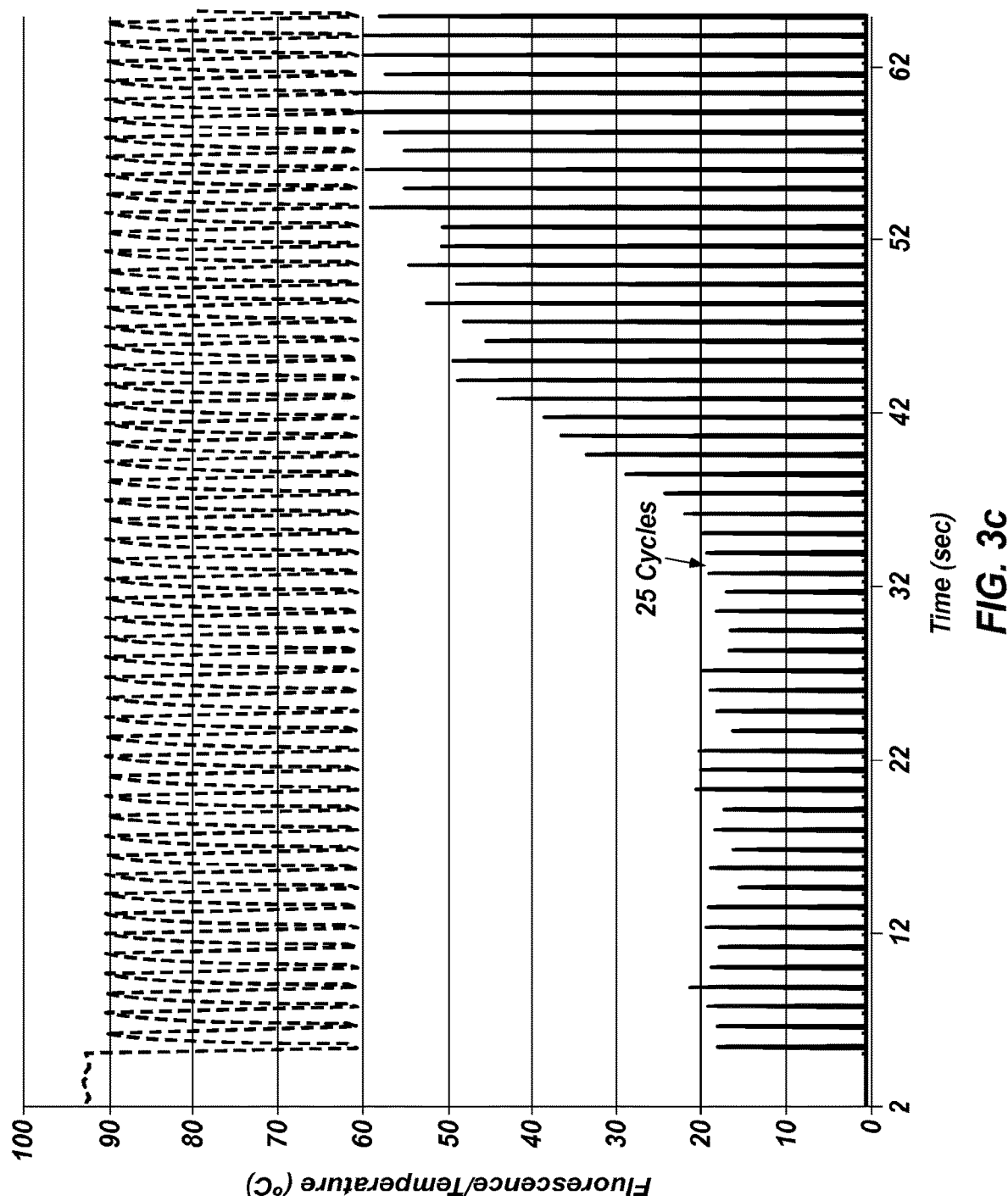
FIG. 3c shows an extreme PCR temperature trace (-----) that amplified the same products shown in FIGS. 3a and 3b, along with real-time monitoring (———) of the same reaction.

Real-time monitoring of the 45 bp KCNE1 reaction was performed using 1 µM polymerase, 10 µM of each primer, and 1.3% glycerol. The sample was monitored each cycle in air between the 2 water baths using the device of FIG. 1a. The enclosed chamber air temperature was held at 70° C. and the sample was interrogated for 0.2 seconds each cycle. As measured by the temperature reference capillary, samples were cycled between 60 and 90° C., as shown in FIG. 3c. The cycle time increased from 0.8 seconds to 1.12 seconds because of the added time for positioning and measuring. Thus, fifty cycles were completed in 56 seconds. Amplification was apparent from an increase in fluorescence at about 30 cycles or after about 34 seconds (FIG. 3c). The temperature remained near 60° C. while the sample was in air for measurement, limiting the extension rate of the polymerase.

As seen in FIG. 3c, this reaction has a quantification cycle (Cq) of about 25 cycles, but it does not seem to plateau until at least 50 cycles. Also, because the reaction was stopped after 64 cycles, it is possible that the quantity of amplicon may continue to increase and not plateau until significantly later. Without being bound to theory, it is believed that the increase in primer concentration allows for improved yield and delayed plateau, illustratively 20 cycles after Cq, and more illustratively 25 cycles or more after Cq.

Example 2

Figure 4A:
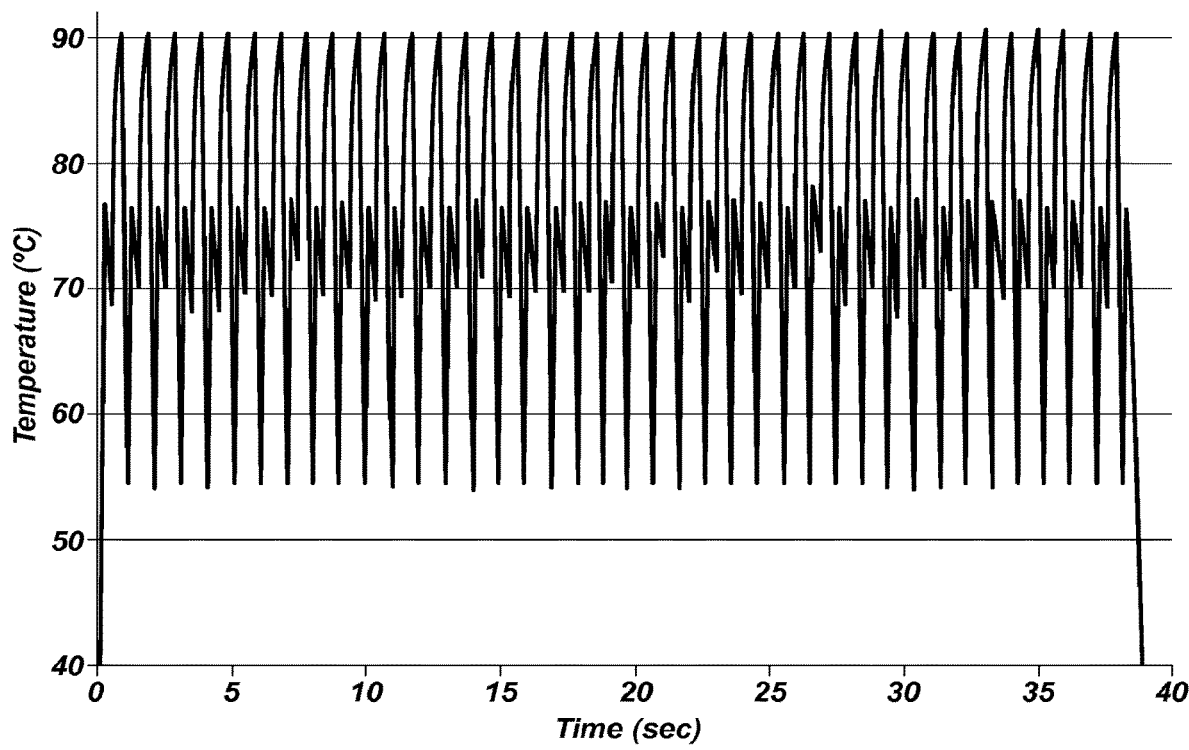
FIG. 4a shows an extreme PCR temperature trace that increases the extension rate by temperature control.
Figure 4B:
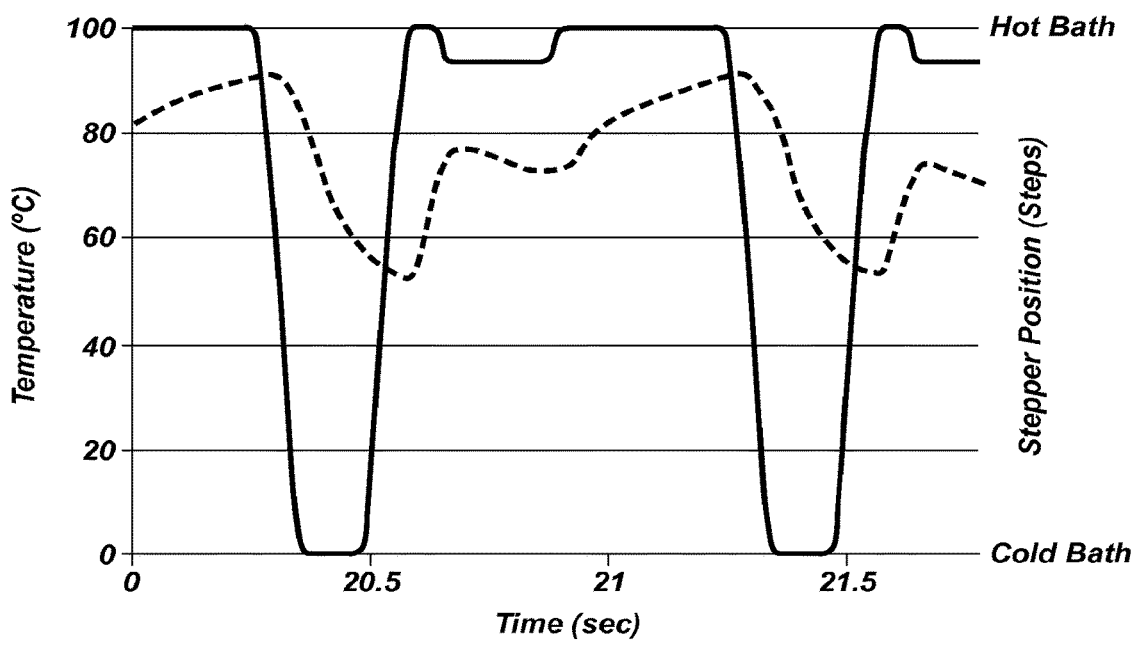
FIG. 4b shows a magnified portion of FIG. 4a, superimposing the location of the sample holder (———) of FIG. 1b with the temperature of the sample (-----).
Figure 4C:
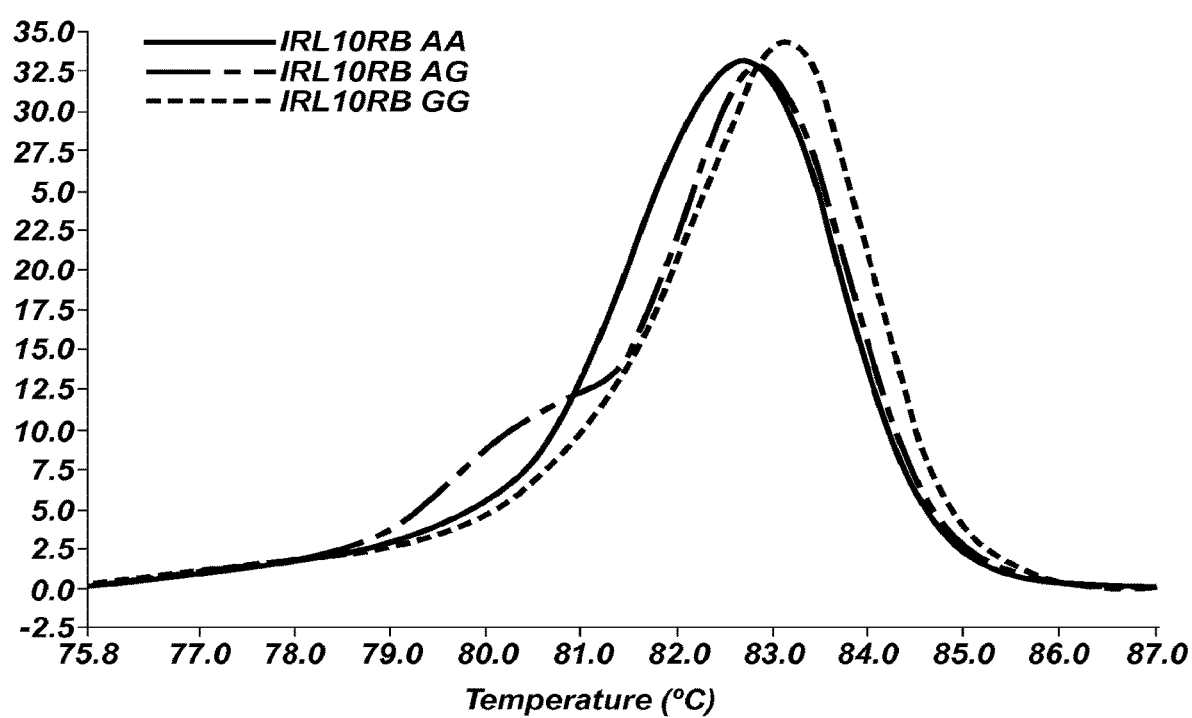
FIG. 4c is a negative derivative melting curve (–dF/dT) of a 58 bp amplicon of IRL10RB, wherein AA (———) AG (—··—), and GG (-----) genotypes are shown.

In this example, a 58 bp fragment bracketing an A>G variant (rs #2834167) in the interleukin 10 beta receptor was amplified with primers CTACAGTGGGAGTCACCTGC (SEQ ID NO:4) and GGTACTGAGCTGT-GAAAGTCAGGTT (SEQ ID NO:5) to generate the following amplicon: CTACAGTGGGAGT-CACCTGCTTTTGCC(A/G) AAGGGAACCTGACTTTCACAGC TCAGTACC (SEQ ID NO:6). Extreme PCR was performed as described in Example 1 using the instrument shown in FIG. 1a. One µM polymerase, 10 µM each primer and 1.3% glycerol were used (polymerase to total primer percentage=5%). In order to increase the temperature for polymerase extension to 70-80° C., where the polymerase has higher extension rates, a different positioning protocol was used. After reaching the annealing temperature, instead of immediately positioning in air for monitoring, the sample was transferred to the hot water bath until the extension temperature was reached. Then the sample was positioned in air just above the hot water bath, producing the temperature cycles shown in FIGS. 4a and 4b, and enabling faster polymerase extension at optimal temperatures between 70 and 77° C. The 3 different genotypes were each amplified by extreme PCR using 0.97 second cycles, completing 39 cycles in 38 seconds. After extreme PCR, high resolution melting curves were obtained for each genotype on an HR-1 instrument modified to accept LC24 capillaries. FIG. 4c reveals that all three genotypes were amplified and distinguished, as expected.

Example 3

The reaction mixtures in Example 1 were the same for both the extreme PCR and rapid cycle PCR, except for the amounts of polymerase and primers, and a minor difference in glycerol concentration that apparently caused the shift in Tm seen in FIG. 3a. In this and all future examples, the glycerol concentration was held at 2% by equalizing its concentration as necessary. For extreme PCR, 1 µM polymerase and 10 µM of each primer were used, while for rapid cycle PCR, 0.064 µM polymerase and 0.5 µM of each primer were used. As discussed above, it is believed that faster annealing times provide for improved primer specificity. With this improved specificity, increased concentrations of primers may be used, which is believed to favor primer binding and allow reduced annealing times. Similarly, increased polymerase concentrations favor binding to the annealed primer, and also favor rebinding to the incomplete amplicon if a polymerase falls off prior to complete extension. In addition, because of the higher polymerase concentration, a greater proportion of the primed templates can be extended at once even late in PCR, reducing the number of templates that a single polymerase must extend and reducing the overall extension time.

Figure 5A:
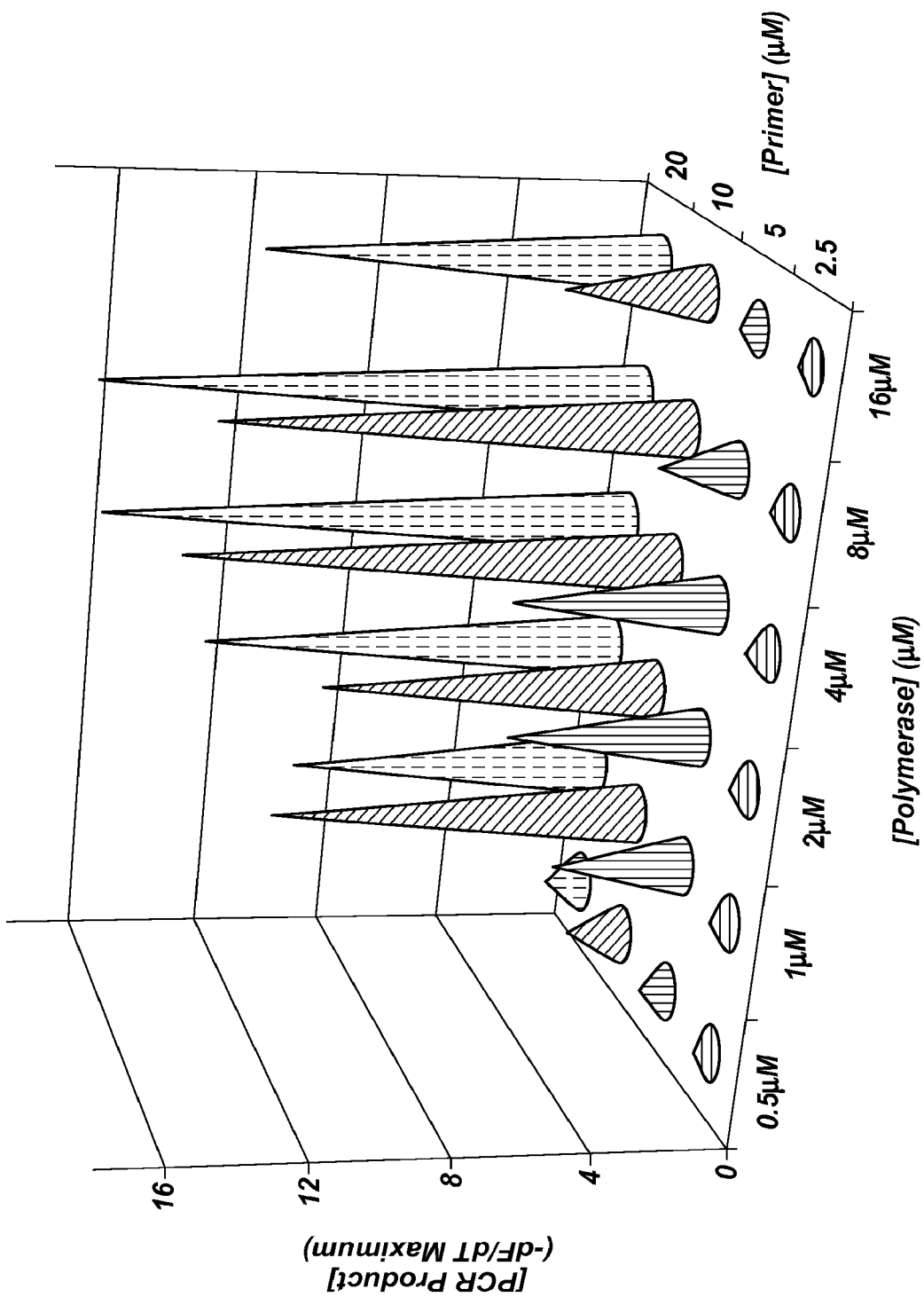
FIG. 5a is a three dimensional graph plotting polymerase concentration vs. primer concentration vs. concentration of PCR product, using extreme PCR.
Figure 5B:
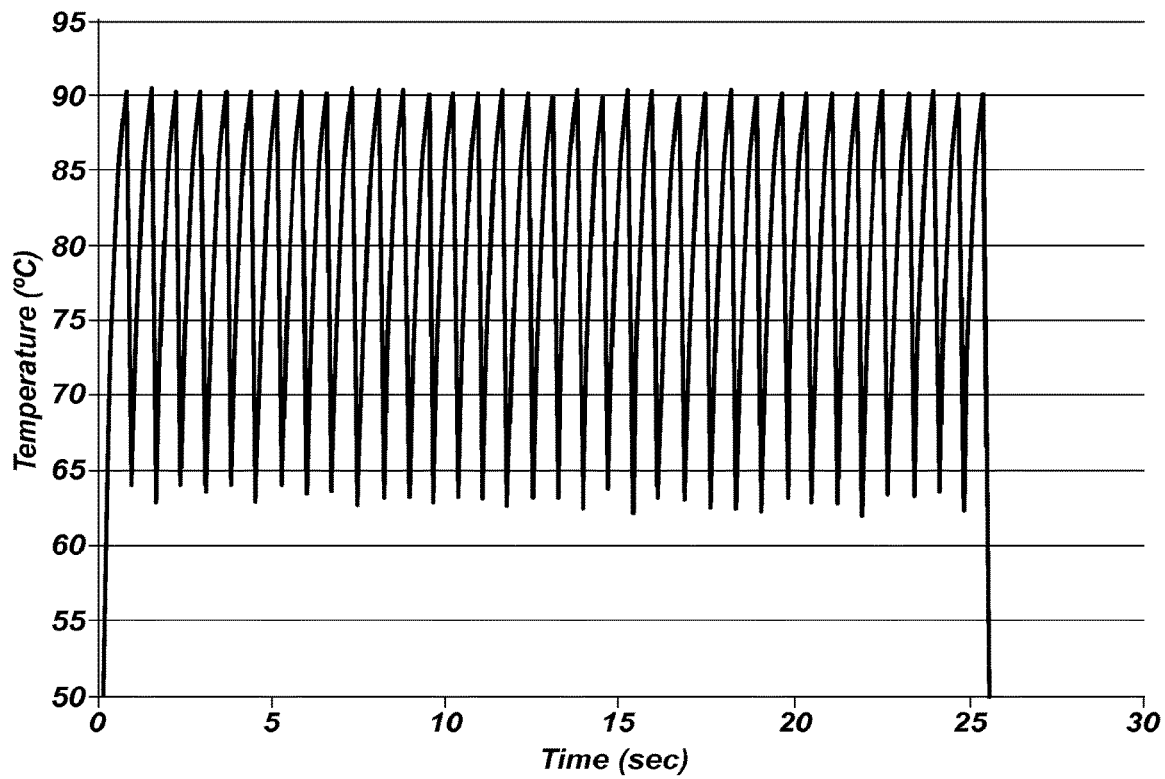

FIG. 5a summarizes the results of extreme PCR cycling with various polymerase and primer concentrations. In this example, a 49 bp fragment of the interleukin 10 beta receptor was amplified with primers GGGAGT-CACCTGCTTTTGCC (SEQ ID NO:7) and TACT-GAGCTGTGAAAGTCAGGTTCC (SEQ ID NO:8) and 3 mM MgCl$_2$, to generate: GGGAGTCACCTGCTTTTGC-CAAAGGGAACCTGACTTTCACAGCTCAGTA (SEQ ID NO:9). For each extreme PCR reaction, the device shown in FIGS. 1b was used without real time monitoring. The temperature was cycled between 90° C. and 63° C. for 35 cycles, for a total reaction time of just under 26 seconds (0.73 second cycles) as shown in FIG. 5b. Reaction conditions were as discussed in Example 1, except that the amounts of polymerase and primers were varied, as shown in FIG. 5a. The vertical axis in FIG. 5a is quantified as the peak of the negative derivative plot of the melting curve, obtained without normalization on the HR-1 instrument. At 0.5 µM polymerase, virtually no amplification was seen at any level of primer concentration. However, at 1.0 µM polymerase, discernible levels of amplification were seen at primer concentrations of 5 µM and above. As the polymerase levels increase, so do the amount of amplicon, up to levels of about 4 µM. At 8 µM polymerase, the amount of amplicon plateaued or dropped off, depending on the primer concentration, with a significant drop off at 16 µM at lower primer concentrations. It appears that under these extreme temperature cycling conditions for a 49 bp product, the polymerase has a favored concentration range between about 1 and 8 µM, and more specifically between 2 and 8 µM, depending on the primer concentration.

Figure 5C:
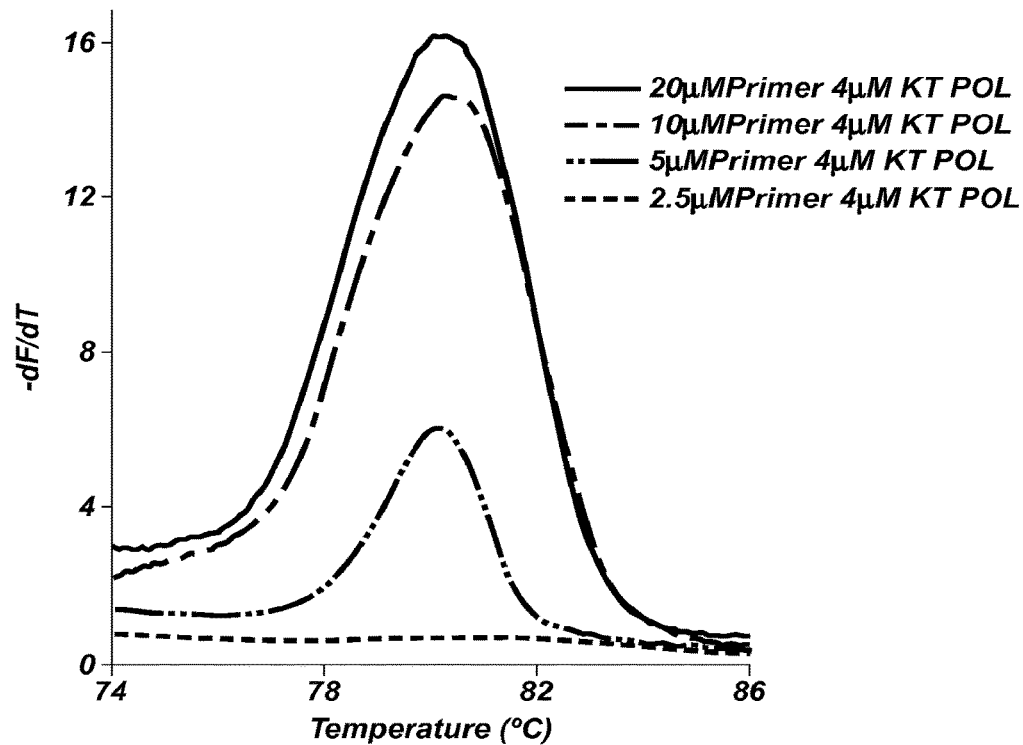
Figure 5D:
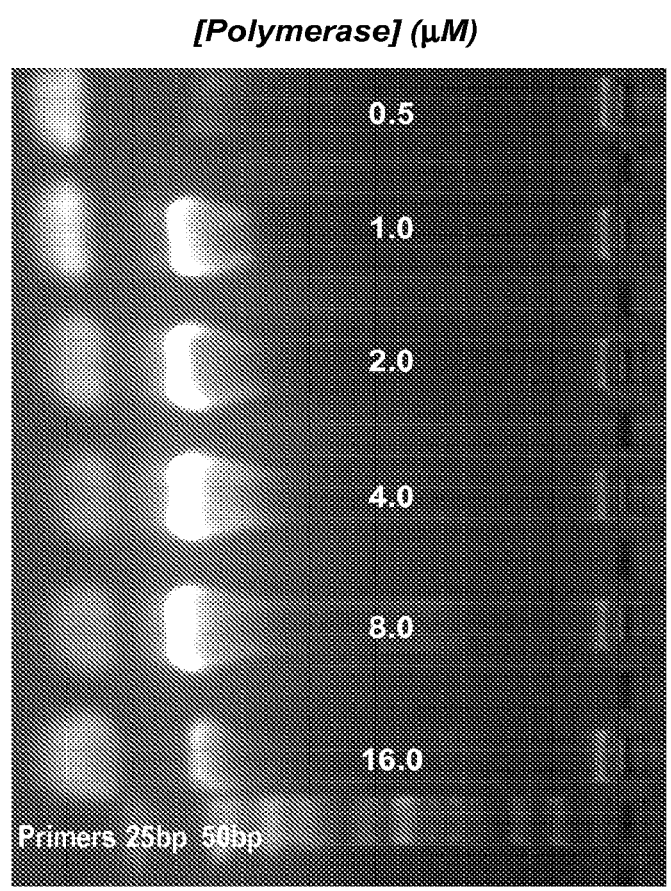

Similarly, little amplification was seen with primer concentrations of 2.5 µM. However, amplification was successful at 5 µM primer, with KlenTaq concentrations of 2-8 µM, and amplification continued to improve with increasing concentrations. Excellent amplification was achieved with primer concentrations of about 10-20 µM primer. FIG. 5c shows melting curves for various primer concentrations at 4 µM KlenTaq, while FIG. 5d verifies the size of the product as the polymerase concentration varies while the primer concentration is held at 10 µM. Despite the high concentrations of polymerase and primers, no nonspecific amplification is seen.

Without being bound to theory, it appears that the ratio between the amount of enzyme and amount of primer is important for extreme PCR cycling, provided that both are above a threshold amount. It is noted that the above amounts are provided based on each primer. Given that the polymerase binds to each of the duplexed primers, the total primer concentration may be the most important. For KlenTaq, suitable ratios are 0.03-0.4 (3-40% enzyme to total primer concentration), with an illustrative minimum KlenTaq concentration of about 0.5 µM, and more illustratively about 1.0 µM, for extreme PCR. The primers may be provided in equimolar amounts, or one may be provided in excess, as for asymmetric PCR. The optimal polymerase:primer percentage may also depend on the temperature cycling conditions and the product size. For example, standard (slow) temperature cycling often uses a much lower polymerase to primer percentage, typically 1.5 nM (0.04 U/µl) polymerase (49) and 1,000 nM total primer concentration, for a percentage of 0.15%, over 10 times lower than the percentages found effective for extreme PCR.

Example 4

Figure 6B:
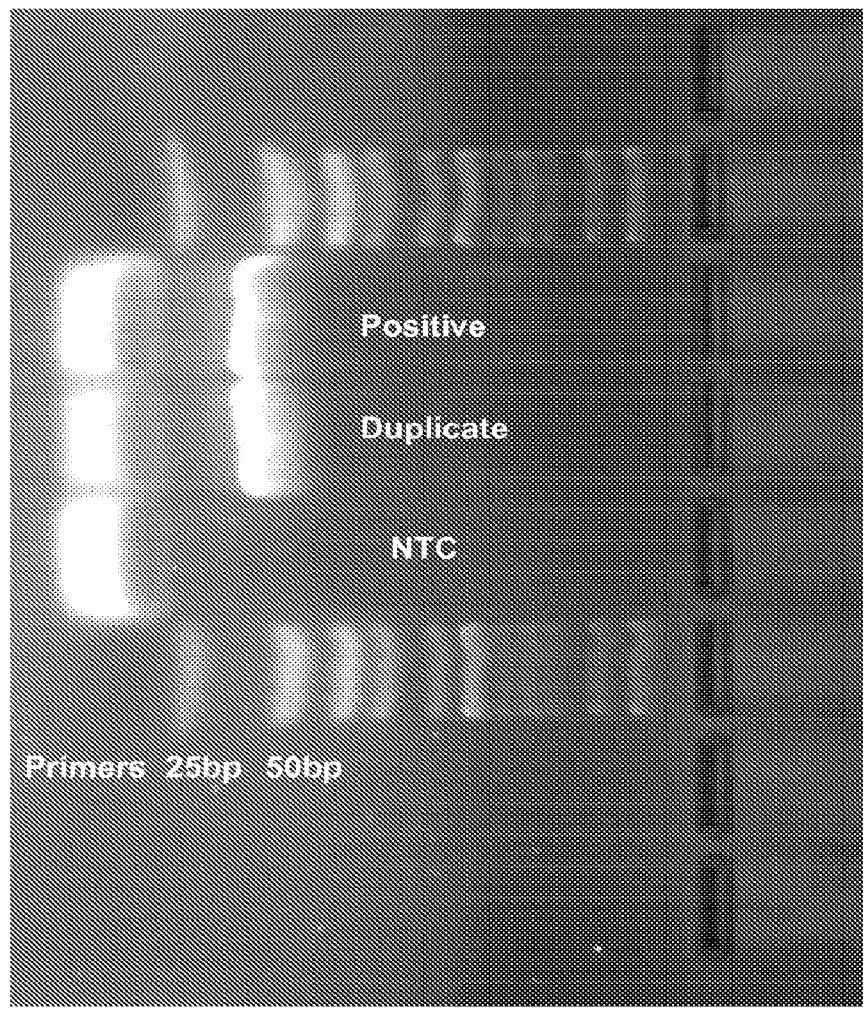

The same PCR target as in Example 3 was amplified with 8 µM polymerase and 20 µM each primer in a 19 gauge steel hypodermic needle, to increase thermal transfer and cycling speeds. The polymerase to total primer percentage was 20%. Amplification was performed on the instrument of FIG. 1b and was completed in 16 seconds using 35 cycles of 0.46 seconds each (FIG. 6a), cycling between 91° C. and 59-63° C. The maximum heating rate during cycling was 407° C./s and the maximum cooling rate was 815° C./s, demonstrating that PCR can occur with ramp rates of greater than 400° C./s with no holds. Analysis of the products on a 4% NuSieve 3:1 agarose gel revealed strong specific bands of the correct size (FIG. 6b). The no template control showed no product at 49 bp, but did show a prominent primer band similar to the positive samples.

Example 5

Figure 7A:
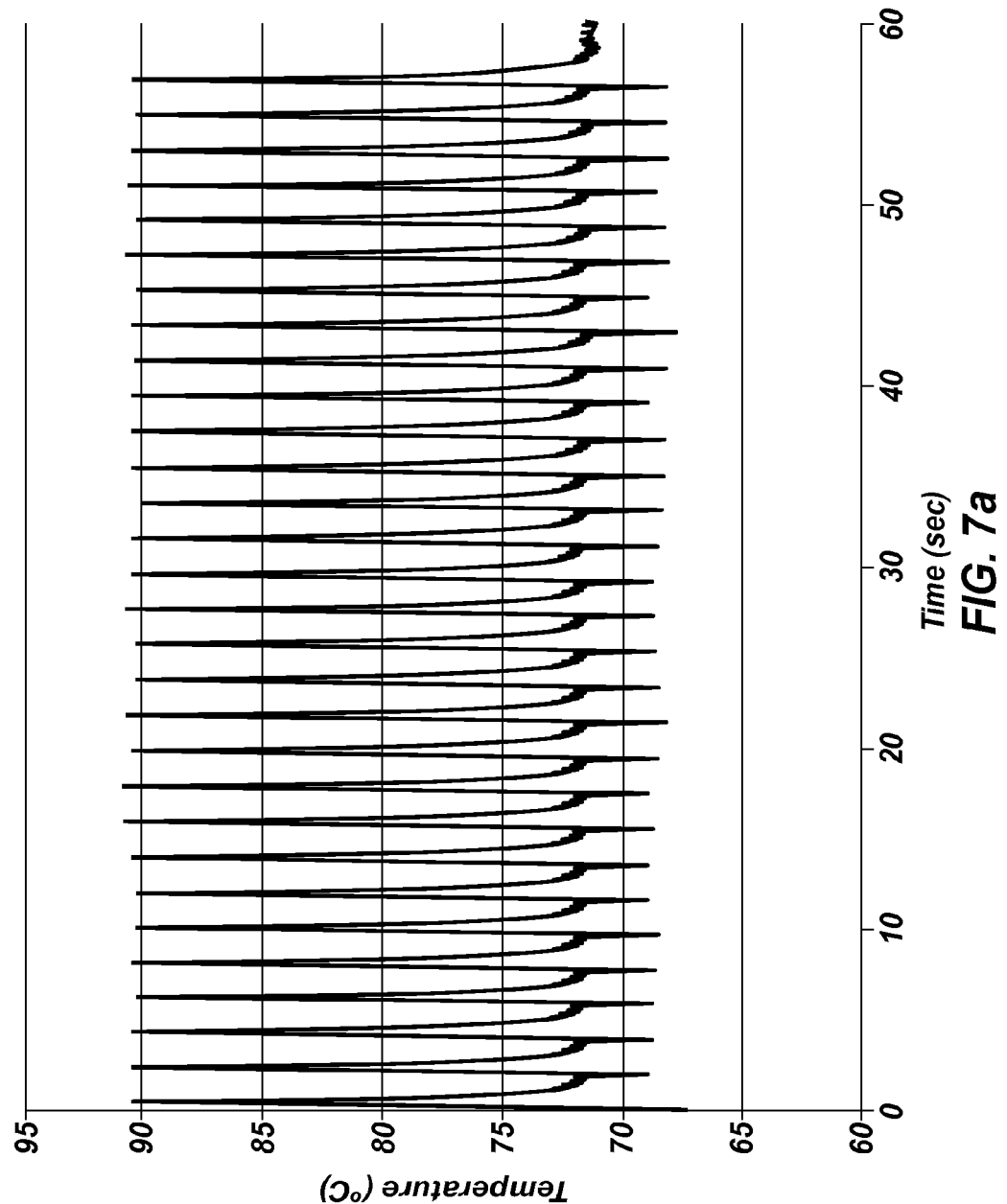
FIG. 7a is an extreme PCR temperature trace with a long (1 second) combined annealing/extension step.
Figure 7B:
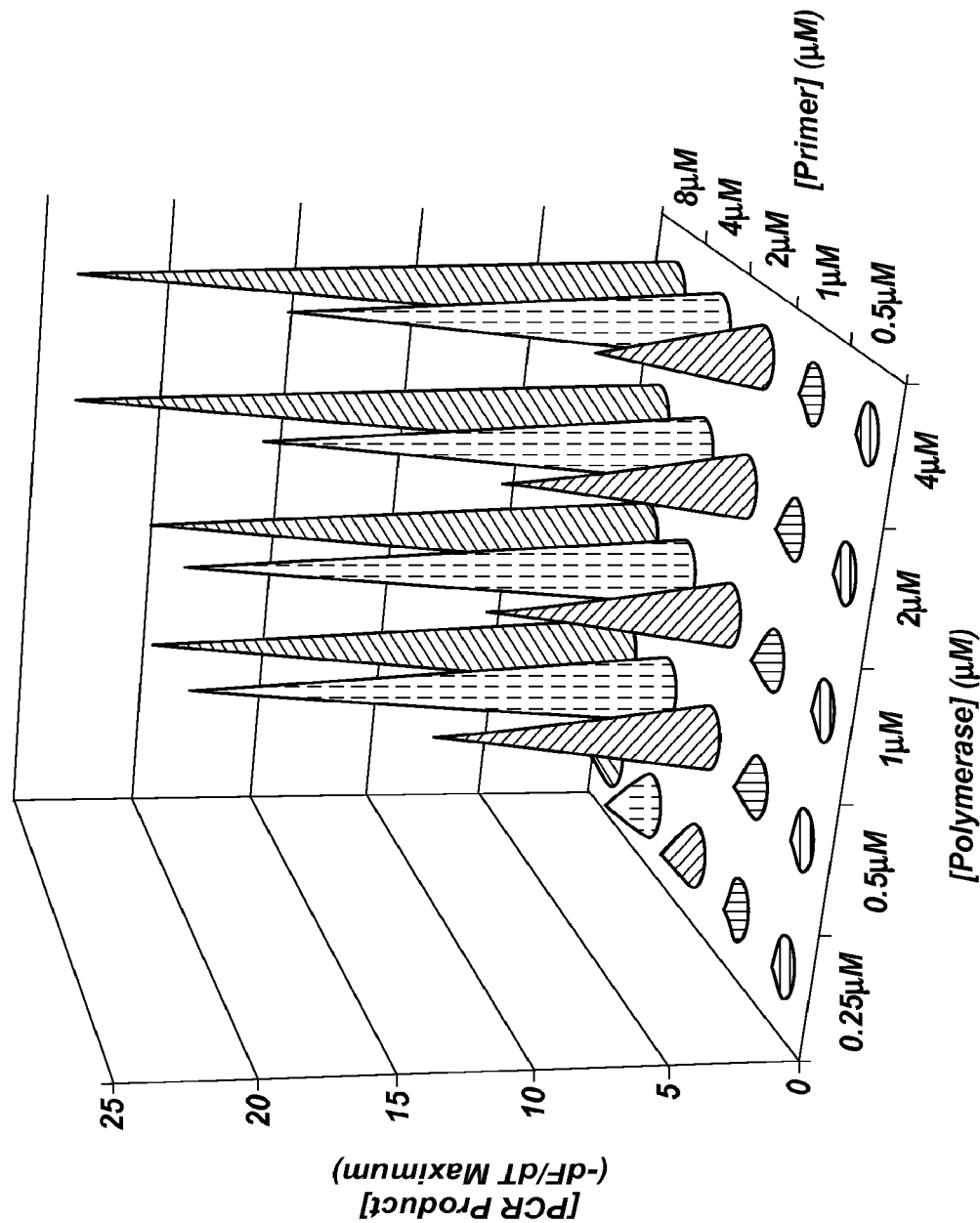
FIG. 7b is a three dimensional graph plotting polymerase concentration vs. primer concentration vs. concentration of PCR product, using extreme PCR for a 102 bp product.

A 102 bp fragment of the NQO1 gene was amplified using primers CTCTGTGCTTTCTGTATCCTCAGAGTGGCAT-TCT (SEQ ID NO:10) and CGTCTGCTGGAGTGTGCC-CAATGCTATA (SEQ ID NO:11) and the instrument of FIG. 1b without the real-time components. The polymerase concentration was varied between 0.25 and 4 µM, while each primer concentration was varied between 0.5 and 8 µM. The primers were designed to anneal at higher temperatures (low 70s) so that extension at a combined annealing/extension phase would be at a more optimal temperature for the polymerase. Greater polymerization rates at these temperatures were expected to enable amplification of longer products. The cooler water bath was controlled at 72° C. and the end of the annealing/extension phase triggered by time (1 second), rather than temperature. Cycling between 72 and 90° C. for 30 cycles required 58 seconds using 1.93 second cycles (FIG. 7a). As seen in FIG. 7a, the sample temperature drops about 3° C. below the annealing/extension temperature while it travels through the air to the hot water bath. FIG. 7b shows the amount of product amplified by quantifying the melting curves as in FIG. 5a. Melting curve analysis showed only a single product of Tm 84° C. Very little product was observed at 0.25 µM polymerase or at 1 µM each primer. Some amplification occurs at 2 µM each primer, with the best amplification at 2-4 µM polymerase and 8 µM each primer. At primer concentrations of 2-4 µM, yield decreases as the polymerase concentration increases, although this was not seen at 8 µM primer concentration. Although the thermal cycling and target length are different from Example 3, the best amplification occurs at polymerase to total primer concentrations of 3.1 to 50%.

Example 6

Extreme PCR was used to amplify 135 bp and 337 bp fragments of the BBS2 gene using the instrument shown in FIG. 1b with real time monitoring. In order to study the effect of product length on extreme PCR and control for possible confounding effects of different primers, the fragments were first amplified from genomic DNA using primers with common 5'-end extensions. For the 135 bp fragment the primers were ACACACACACACACACACACACACACACACAC ACAAAAATTCAGTGGCAT TAAATACG (SEQ ID NO:12) and GAGAGAGAGAGAGAGAGAGAGAGAGAGAGAG AGAGAGAGAGAGAAAAA CCAGAGCTAAAGG-GAAG (SEQ ID NO:13). For the 337 bp fragment the primers were ACACACACACACACACACACACACACACACAC ACAAAAAGCTGGTGTCTG CTATAGAACTGATT (SEQ ID NO:14) and GAGAGAGAGAGAGAGAGAGAGAGAGAGAGAG AGAGAGAGAGAGAAAAA GTTGCCAGAGCTAAAGGGAAGG (SEQ ID NO:15). After standard PCR amplification from genomic DNA, primers and dNTPs were degraded by ExoSAP-IT (Affymetrix, CA), followed by PCR product purification using the QuickStep™ 2 PCR Purification Kit (Catalog #33617, Edge BioSystems, Gaithersburg, Md.). PCR products were diluted approximately 1 million-fold and adjusted to equal concentrations by equalizing the Cq obtained by standard real-time PCR to obtain a Cq of 25 cycles (approximately 10,000 copies/10 µl reaction).

Figure 8A:
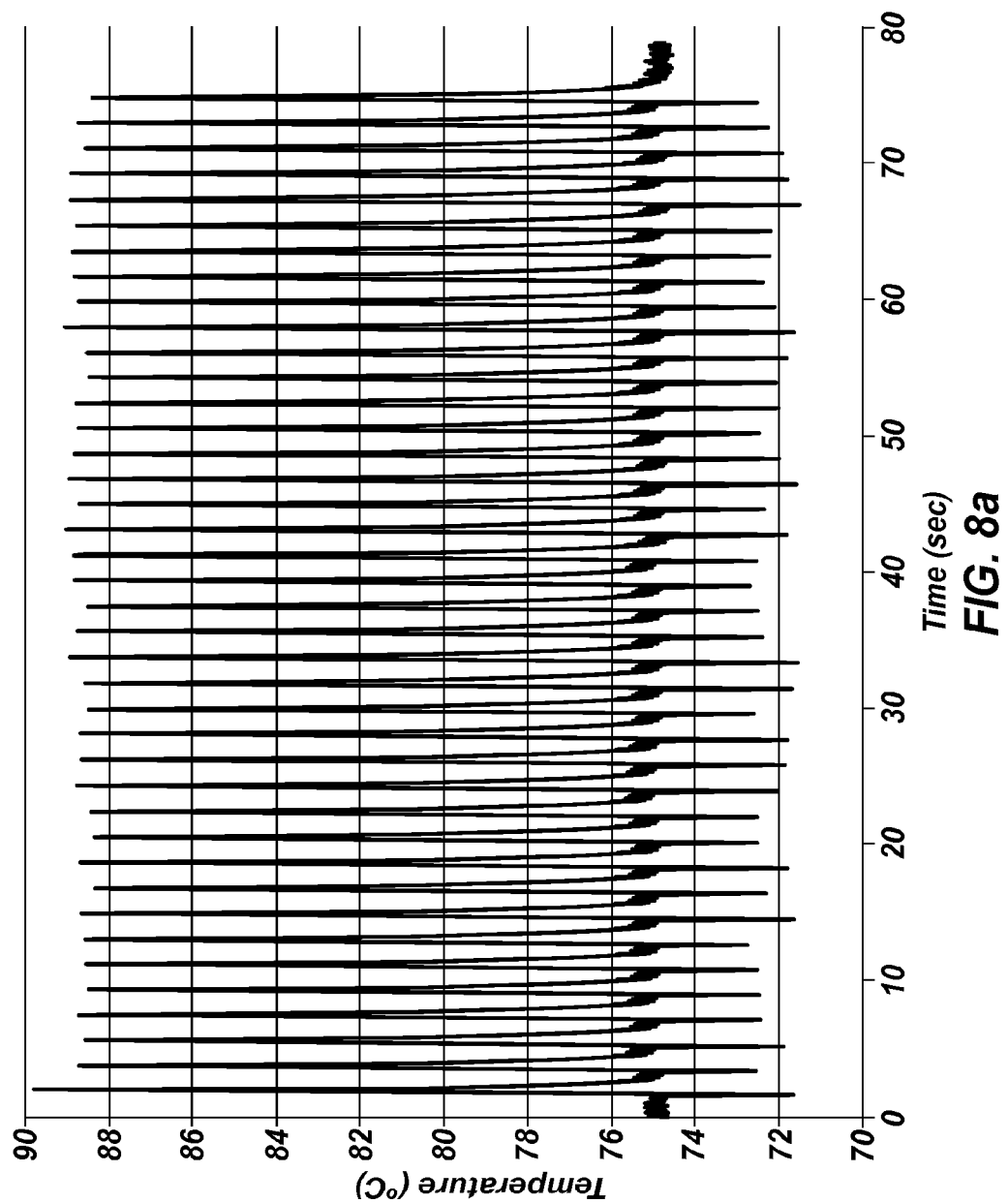
FIG. 8a shows an extreme PCR temperature profile used to amplify a 226 bp product, using a one second combined annealing/extension step.
Figure 8B:
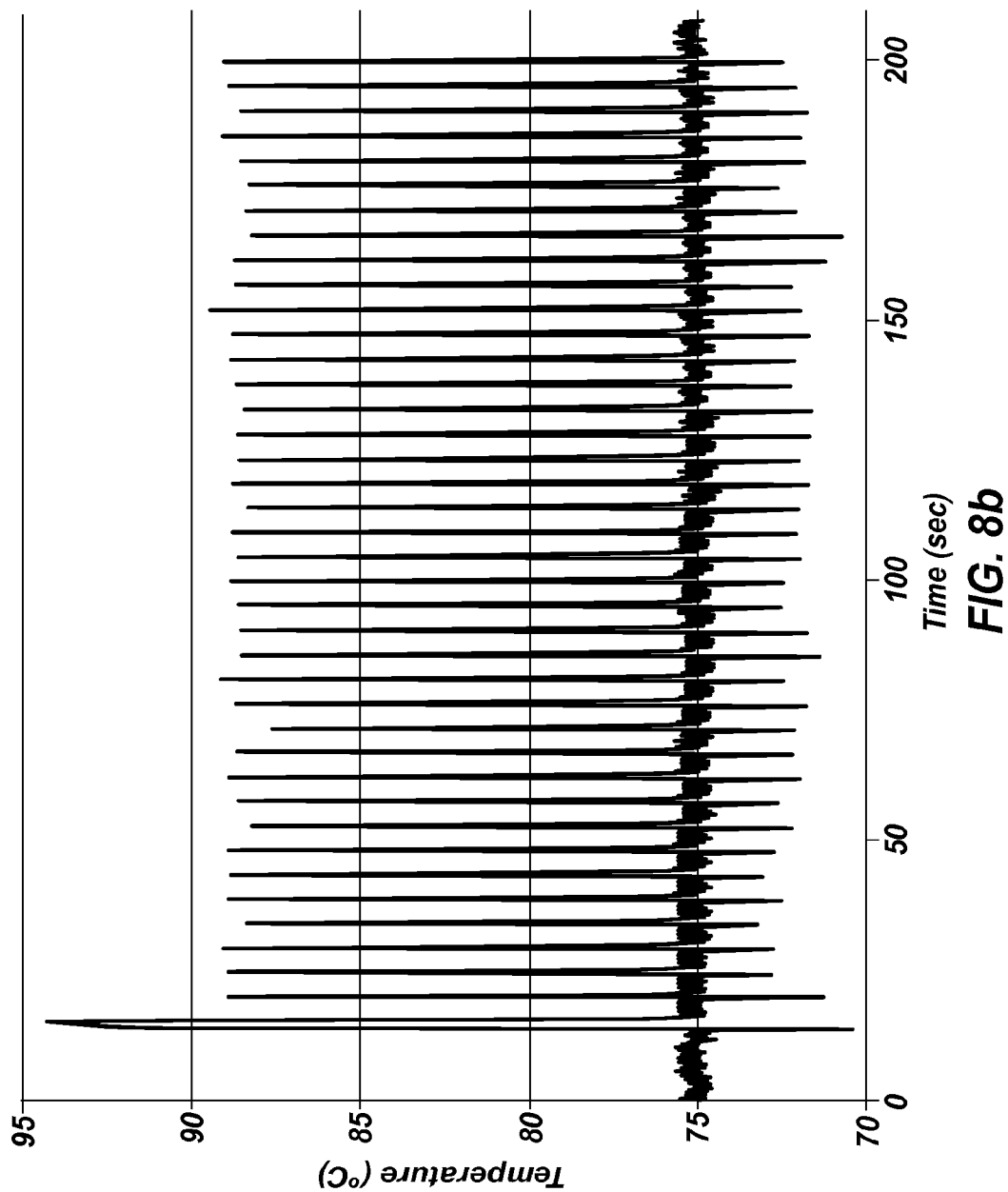
FIG. 8b shows an extreme PCR temperature profile used to amplify a 428 bp product, using a four second combined annealing/extension step.
Figure 8C:
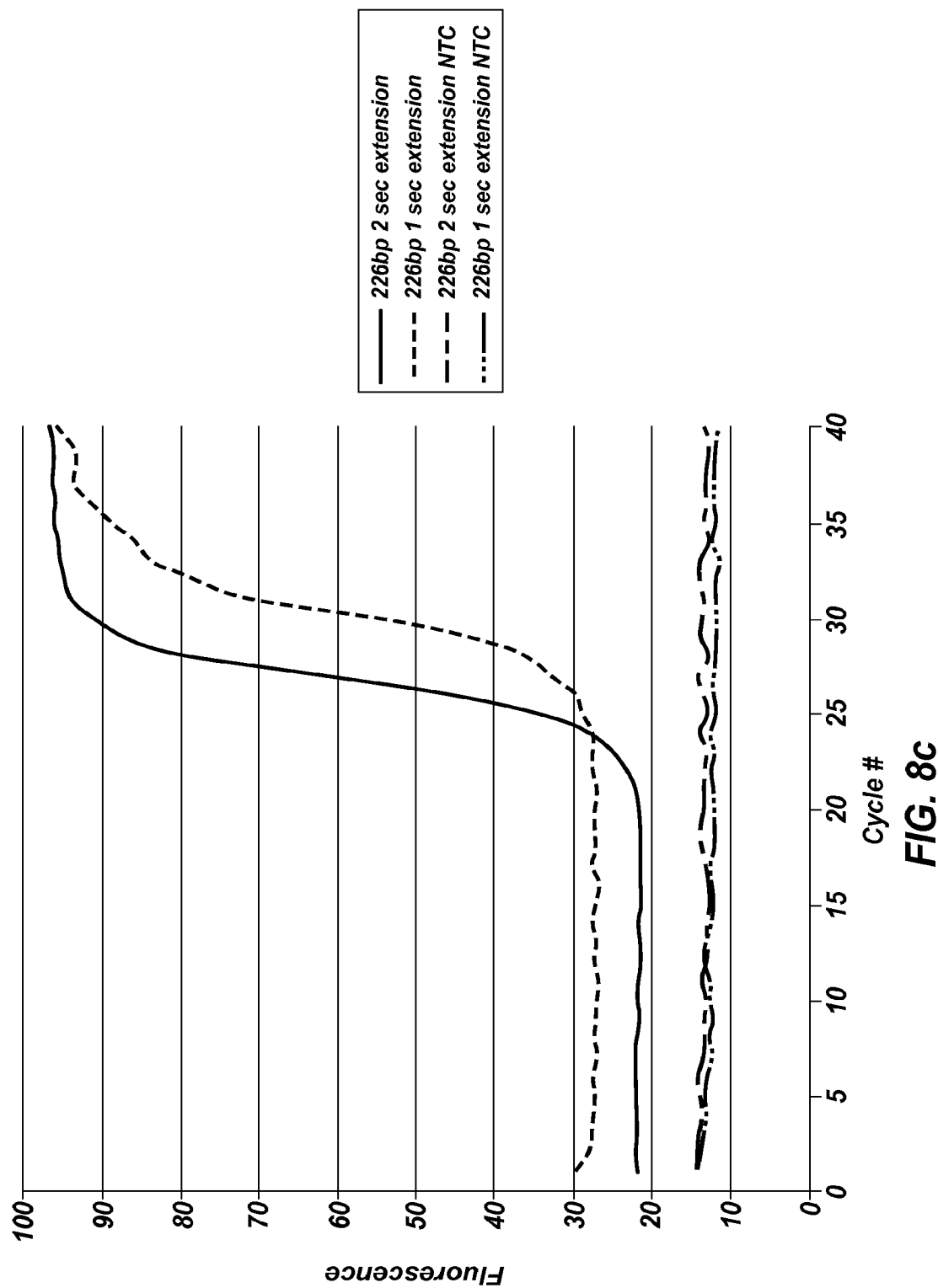
FIG. 8c shows the real time results obtained from FIG. 8a and a similar temperature trace using a 2 second annealing/extension step, including no template controls for each.
Figure 8D:
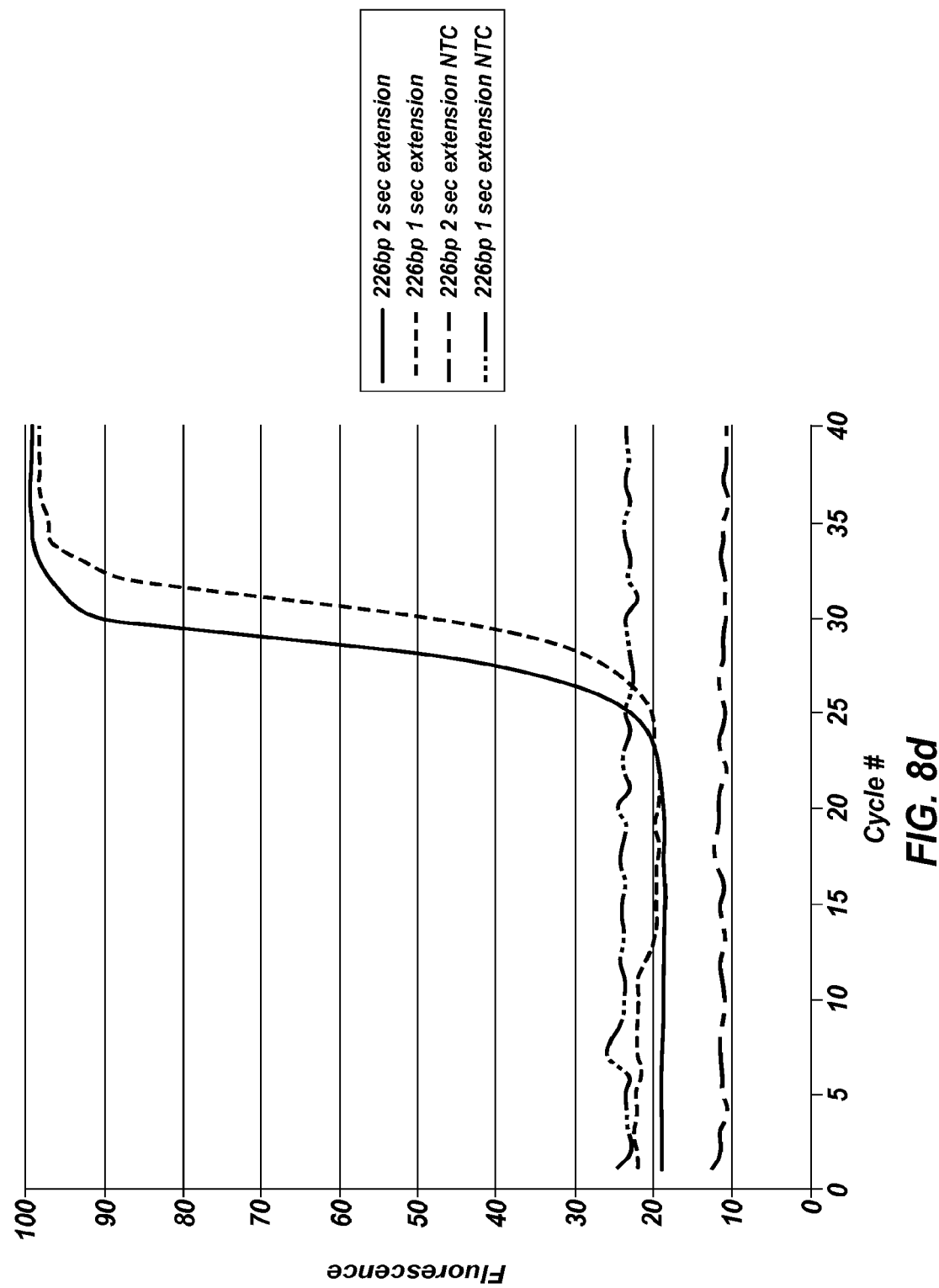
FIG. 8d shows the real time results obtained from FIG. 8b and a similar temperature trace using a 5 second annealing/extension step, including no template controls for each.

Extreme PCR was performed on 1,000 copies of the amplified templates in a total volume of 5 µl using the common primers ACACACACACACACACACACACACACACACAC ACAAAAA(SEQ ID NO:16) and GAGAGAGAGAGAGAGAGAGAGAGAGAGAGAG AGAGAGAGAGAGAAAAA (SEQ ID NO:17) each at 2 µM with 2 µM polymerase and 2% glycerol. The 135 bp BBS2 fragment resulted in a 226 bp product requiring extension of 176 or 185 bases (depending on the primer), while the 337 bp BBS2 fragment resulted in a 428 bp PCR product requiring extension of 378 or 387 bases. Specific amplification was verified on agarose gels and by melting analysis. The extreme PCR temperature profile used for the 226 bp product is shown in FIG. 8a, which included a 1 second combined annealing/extension at 75° C. and denaturation at 87° C. Also performed was a 2 second annealing/extension phase at the same temperature (trace not shown). Real time PCR results for these amplifications are shown in FIG. 8c, revealing about a 5 cycle shift to higher Cq with the 1 second extension as compared to the 2 second extension, presumably reflecting a decrease in efficiency as the extension time is decreased. The extreme PCR temperature profile used for the 428 bp product is shown in FIG. 8b, showing a 4 second combined annealing/extension at 75° C. and denaturation at 87° C. Also performed was a 5 second annealing/extension phase at the same temperature (trace not shown). Real time PCR results for these amplifications are shown in FIG. 8d, revealing about a 2 cycle shift to higher Cq with the 4 second extension as compared to the 5 second extension, presumably reflecting a decrease in efficiency as the extension time is decreased.

Example 7

Figure 9A:
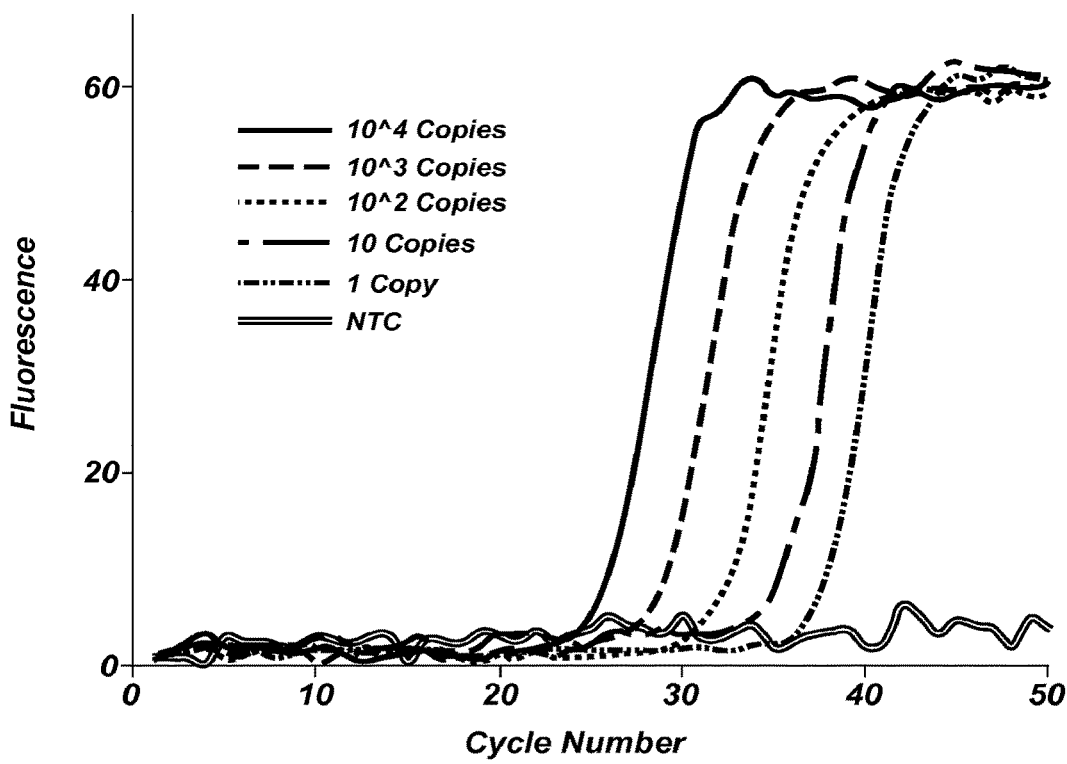
FIG. 9a shows amplification curves of a 45 bp fragment of KCNE1 at different starting concentrations.
Figure 9B:
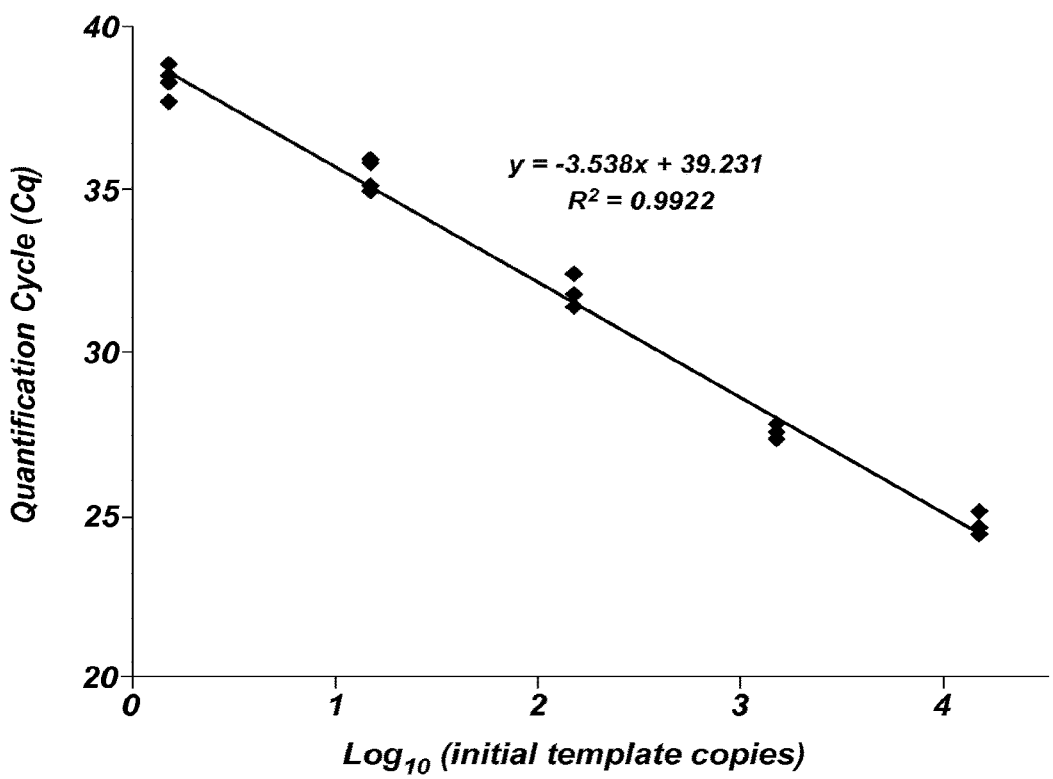
FIG. 9b is a plot of Cq versus $\log_{10}$ (initial template copies) of the data from FIG. 9a. Reactions were performed in quintuplicate.
Figure 9C:
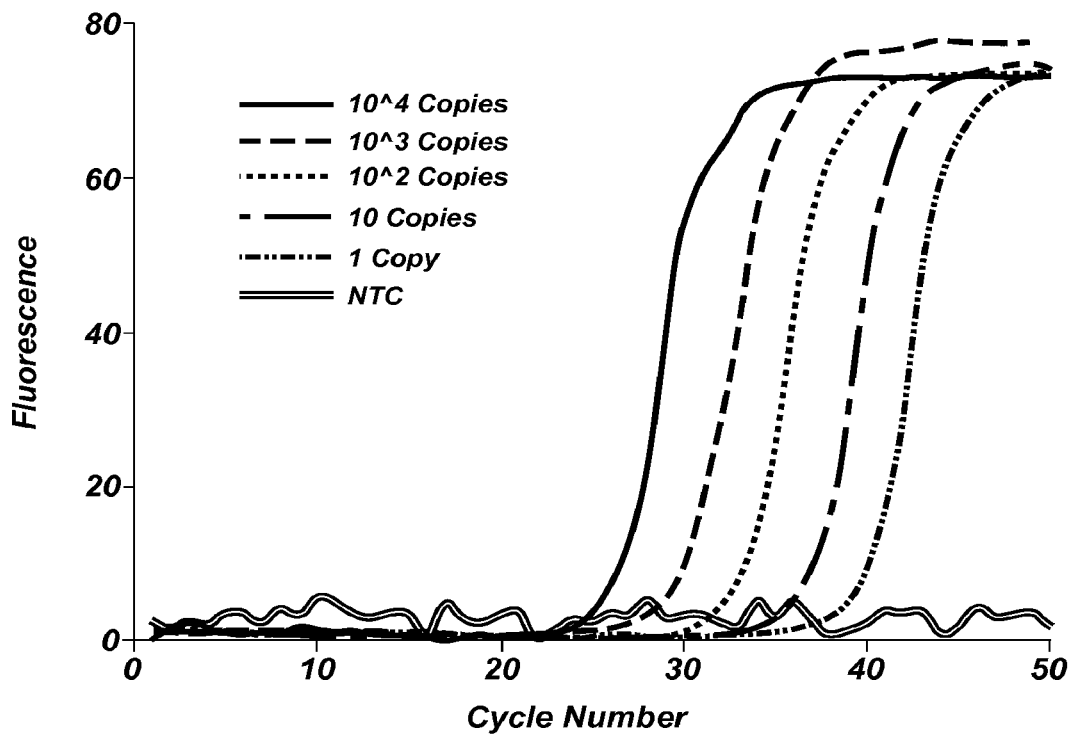
FIGS. 9c-9d are similar to FIGS. 9a-9b, except showing amplification of a 102 bp fragment of NQO1.
Figure 9D:
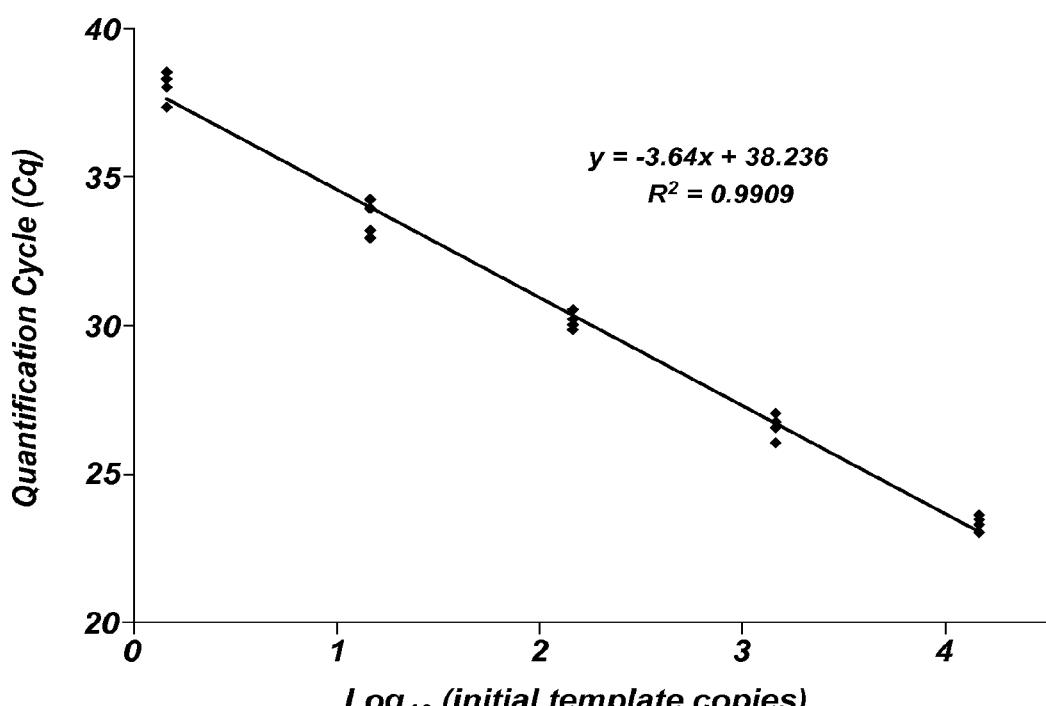

Quantitative performance of PCR was assessed using the real-time instrument of FIG. 1b for the 102 bp fragment of NQO1 of Example 5 and the 45 bp fragment of KCNE1 of Example 1 using a dilution series of human genomic DNA, using 2 µM KlenTaq and 8 µM each primer for NQO1 and 8 µM KlenTaq and 20 µM each primer for KNCE1. With a dynamic range of at least 4 decades, as seen in FIGS. 9a and 9b, the amplification efficiencies calculated from the standard curves were 95.8% for NQO1 and 91.7% for KCNE1. Control reactions without template did not amplify after 50 cycles and single copy replicates (mean copy number of 1.5 copies per reaction) were similar in amplification curve shape and intensity to higher concentrations (FIGS. 9A and 9C). At a mean copy number of 0.15 copies/reaction, 2 reactions were positive out of 17 (combining both NQO1 and KCNE1 trials), with a calculated expectation of 0.13 copies/reaction by binomial expansion.

Example 8

Figure 10A:
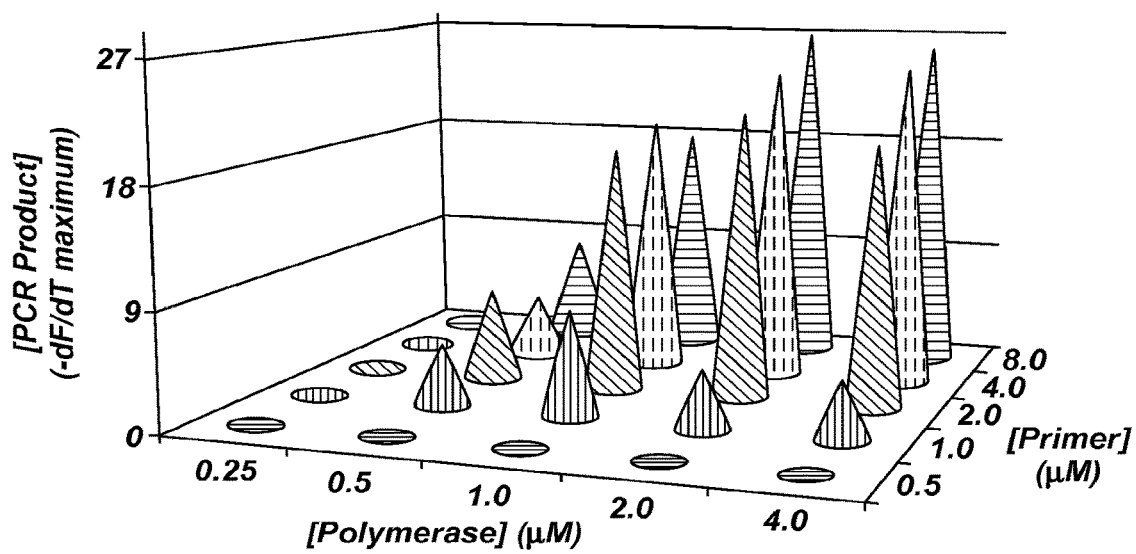
FIG. 10a is a three dimensional graph plotting polymerase concentration vs. primer concentration vs. concentration of PCR product, using extreme PCR for a 300 bp product (20 cycles, 4.9 seconds per cycle).
Figure 10B:
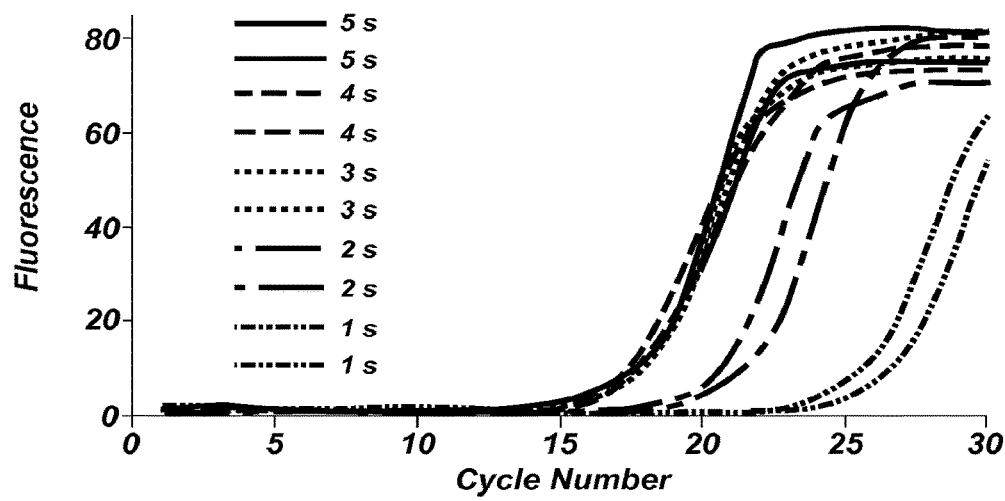
FIG. 10b shows fluorescence versus cycle number plots for PCR amplification of a 500 bp synthetic template using KAPA2G FAST polymerase and 1-5 second extension times.
Figure 10C:
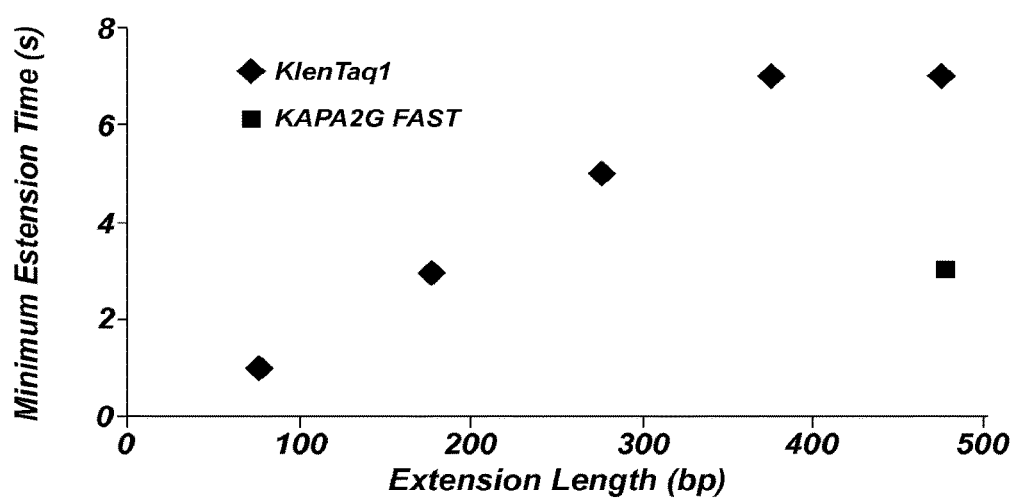
FIG. 10c is a plot of extension length vs. minimum extension time for several KlenTaq polymerase concentrations and KAPA2G FAST polymerase.
Figure 11A:
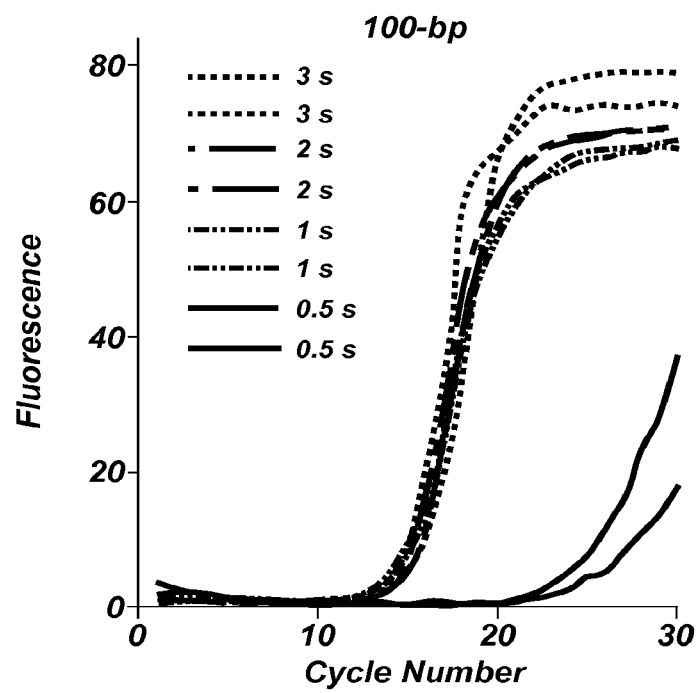
FIGS. 11a-11e show fluorescence versus cycle number plots for PCR amplification of products of size: 100 bp (FIG. 11a), 200 bp (FIG. 11b), 300 bp (FIG. 11c), 400 bp (FIGS. 11d), and 500 bp (FIG. 11e).
Figure 11B:
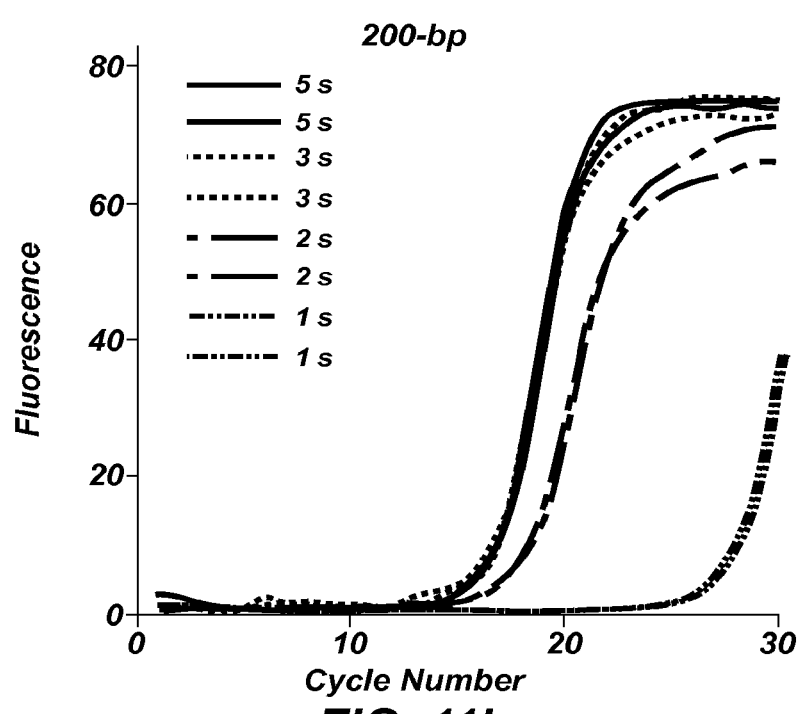
Figure 11C:
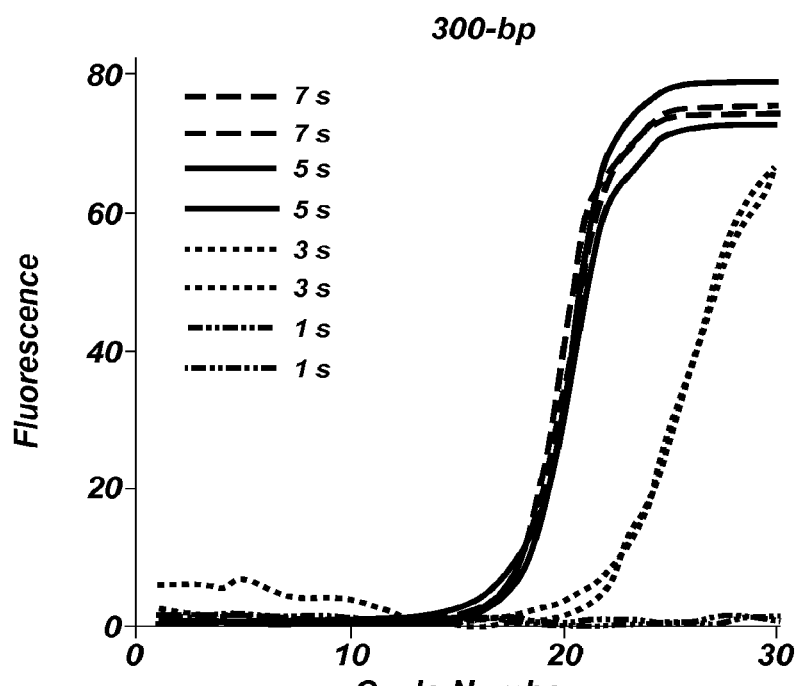
Figure 11D:
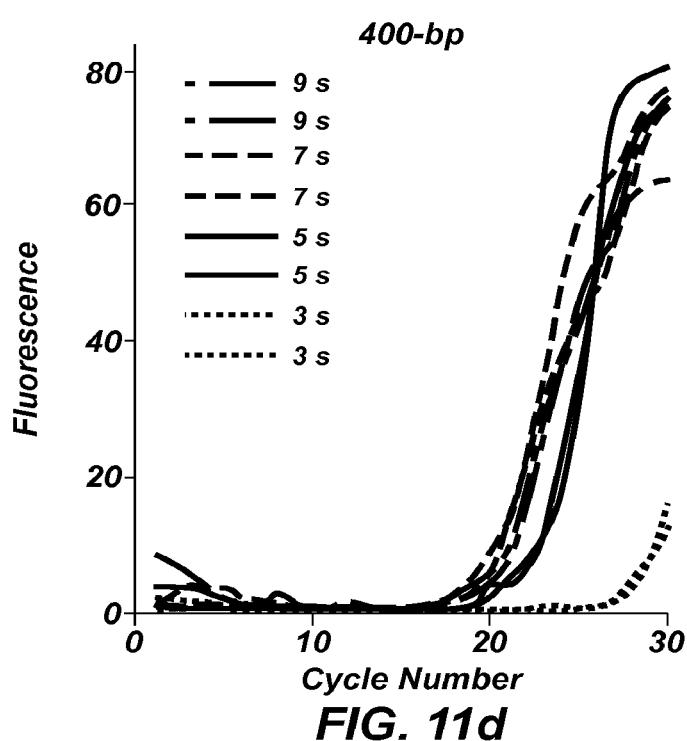
Figure 11E:
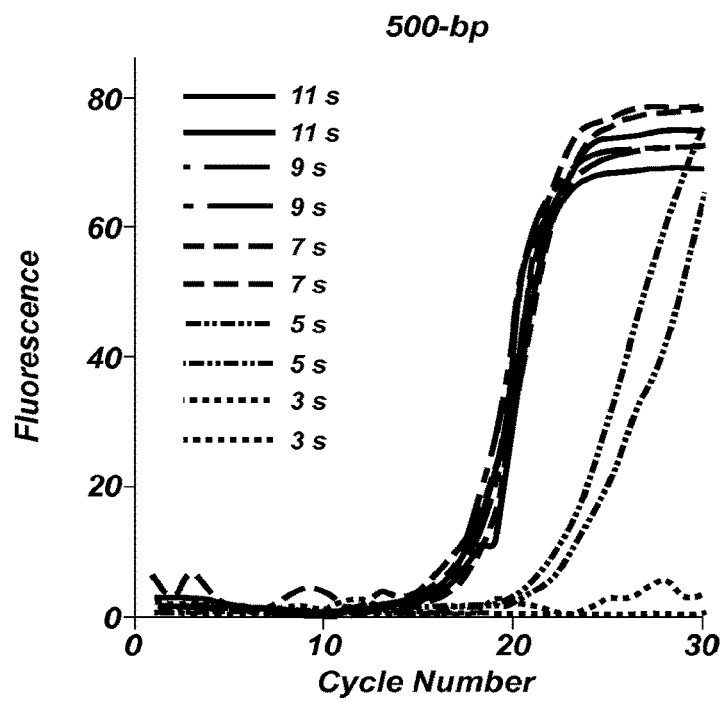

The extension time required for different product lengths using real-time PCR (FIG. 10a-c). To control for the possible confounding effects of different primers, synthetic templates of 100-500 bp using the following common high Tm (77° C.) primers:

```
                                        (SEQ ID NO: 18)
ACTCGCACGAACTCACCGCACTCC
and (SEQ ID NO: 19)
GCTCTCACTCGCACTCTCACGCACA.
```

The synthetic template sequences were:

```
100 bp Template:
                                        (SEQ ID NO: 20)
ACTCGCACGAACTCACCGCACTCCGGATGGATTGTGAAGAGGCCCAAGAT

ACTGGTCATATTATCCTTTGATCTAGCTCTCACTCGCACTCTCACGCAC

A.

200 bp Template:
                                        (SEQ ID NO: 21)
ACTCGCACGAACTCACCGCACTCCTCAATGCTGACAAATCGAAAGAATAG

GAATAGCGTAATTACTAGAGGACTCCAATATAGTATATTACCCTGGTGAC

CGCCTGTACTGTAGGAACACTACCGCGGTTATATTGACAGCTTAGCAATC

TACCCTGTTGGGATCTGTTTAAGTGGCTCTCACTCGCACTCTCACGCAC

A.

300 bp Template:
                                        (SEQ ID NO: 22)
ACTCGCACGAACTCACCGCACTCCCCTTCGAATATAAAGTACGACATTAC

TAGCAATGACAGTTCCAGGATTTAAGAAAGTAGTGTTCCACATCAATGCA

TATCCAGTGAAAGCATAACGTCAAAAAAAGCCTGGCACCGTTCGCGATCT

GGACTTACTTAGATTTGTTGTAGTCAAGCCGGCTATCAGCGATTTATCCC
```

```
GGAAACACATACTAGTGAGTTATTTGTATGTTACCTAGAATAGCTGTCAC

GAATCACTAATACATTCACCCACCAGCTCTCACTCGCACTCTCACGCAC

A.

400 bp Template:
                                        (SEQ ID NO: 23)
ACTCGCACGAACTCACCGCACTCCTGAATACAAGACGACAGTCCTGATTA

TATTTTCATTTAATTACGCCAATTTAATTATGATGAATATTAACGGAATT

AAATATGTATTGATAAGTACTAAGTAATGGTTTACCCACGGCGATCTATA

TGCAAGGGAAACATTAACAAATTTAAACATCTGATGTGGACAAAACTTGT

AATGTGGTATAGTTAAAAATATAGGTTTCAGGGACACGTAAGTATCTATC

TTGAATGTTTAAGTAGGTCCTGTCTACCATTCTGAAATTTAGAAAATCGC

GTTCATCGGGCTGTCGGCTACACCTCAGAAAACCATTTCGTGTTGCACAG

GAGGAACTTTCGAGGGTTCGTATGAGCTCTCACTCGCACTCTCACGCAC

A.

500 bp Template:
                                        (SEQ ID NO: 24)
ACTCGCACGAACTCACCGCACTCCACCGCTTGACGACGTAGGGTATTTGG

TATCTGAATCTACTCATTTACCTACATACTGAAGATTTTGCGATCGTCTA

ATATATTGGACTAATGCCCGATTTCTGATCAATTACTCTAGGCGATACTT

CATCGCTGGCCTTATTTGGATTTTGCTCAAGTGCTAAACTCTCTGCGCGT

CAATACTAGTCTGACATCAGTCAAGACCTGCTATCTGAAAACTACTAGAG

AGATATACCTAACAACTTTAGTGGATAAATCAGGTCTGGAGATTGTCATA

TAATGCCACTAGGGTCAGAAGGCTGTGTCAAAGTTAGTGGTTAGTAGGTC

TCCGCTCTGCGGTACTATTCTTATATTCTCTTACTATGCATCAAACAAAA

TAGAATGCATAGACAAACCGCCTGCCAAGTTTACAAGATAACTTGCGTAT

AGGTTTATAAGGGTTCTTCTGTATCGCTCTCACTCGCACTCTCACGCAC

A.
```

Optimal concentrations of primers and polymerase were first determined for the intermediate length 300-bp product using a 4 second combined annealing/extension segment with 4.9 seconds per cycles (FIG. 10a). Identical primer (4 µM) and polymerase (2 µM) concentrations were then used for all product lengths and minimum extension times were determined (FIG. 11 a-e). Depending on the product length, increased extension times resulted in decreased fractional quantification cycles (Cq) until no further change was observed, reflecting the minimum extension time required for efficient PCR. For example, amplification curves using the KAPA2G™ FAST polymerase (Kapa Biosystems) for the 500 bp product are shown in FIG. 10b. The minimum extension time using KAPA2G FAST polymerase was 3 s, compared to 7 s using KlenTaq1 (a deletion mutant of Taq polymerase, AB Peptides). When the identity of the polymerase is kept constant, longer products required longer extension times (FIG. 10c). For KlenTaq1 polymerase, about 1 second is required for each 60 bps, while for KAPA2G FAST, 1 second is required for each 158 bp. It is noted that these two polymerases were chosen because they are commercially available at sufficient concentrations, while most other polymerases are not commercially available at such high concentrations. It is understood that the required time for extension depends directly and linearly with the length to be extended, and inversely with the concentration of polymerase and the polymerase speed. A proportionality constant (k2) can be defined that relates these 3 parameters:

Required Extension Time=k2*(extension length)/ ([polymerase]*(polymerase speed))

Example 9

Extreme PCR times can also be reduced with high $Mg^{++}$ concentrations. A 60 bp fragment of AKAP10 was amplified with primers:

```
                                       (SEQ ID NO: 25)
GCTTGGAAGATTGCTAAAATGATAGTCAGTG
and (SEQ ID NO: 26)
TTGATCATACTGAGCCTGCTGCATAA, to generate the
amplicon (SEQ ID NO: 27)
GCTTGGAAGATTGCTAAAATGATAGTCAGTGAC(A/G)TTATGCAGCAGG
CTCAGTATGATCAA.
```

Figure 12A:
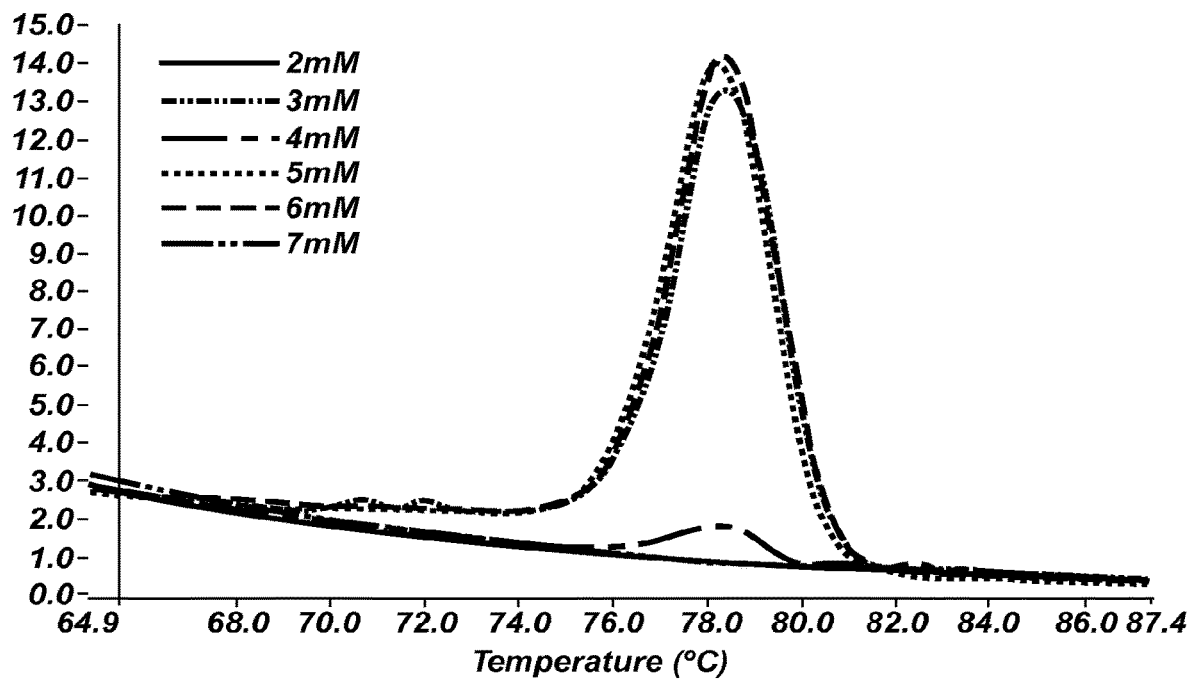
FIG. 12a shows negative derivative melting curves of a 60 bp fragment of AKAP10 after 35 cycles of extreme PCR, using varying magnesium concentrations.
Figure 12B:
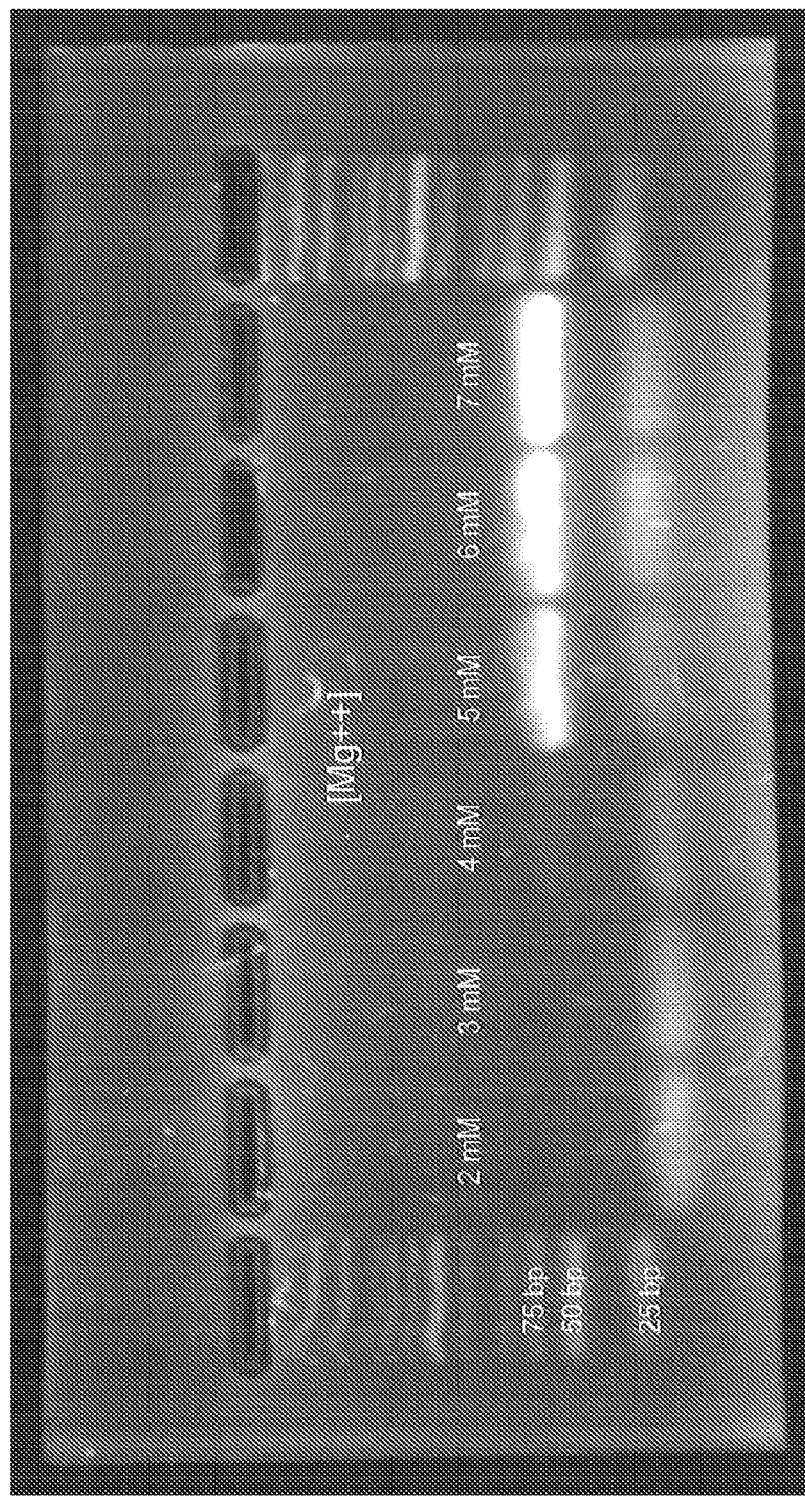
Figure 13A:
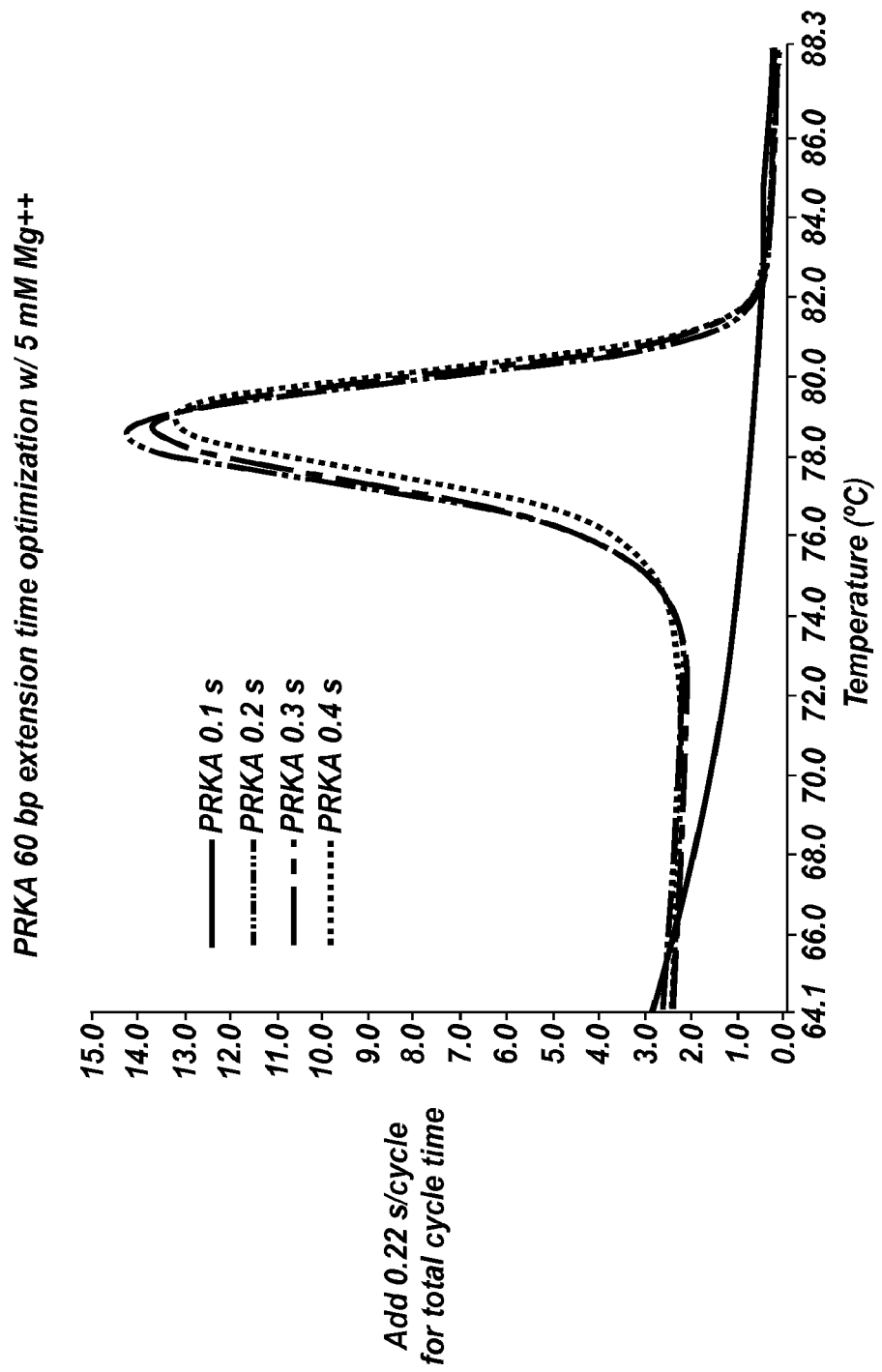
FIG. 13a shows negative derivative melting curves of a 60 bp fragment of AKAP10 after 35 cycles, using varying cycle times with 5 mM $Mg^{++}$. Cycle times were 0.32 seconds (———) 0.42 seconds (—··—), 0.52 seconds (—··—), and 0.62 seconds (-----). Cycle times included a 0.1 to 0.4 second hold in a 60° bath.
Figure 13B:
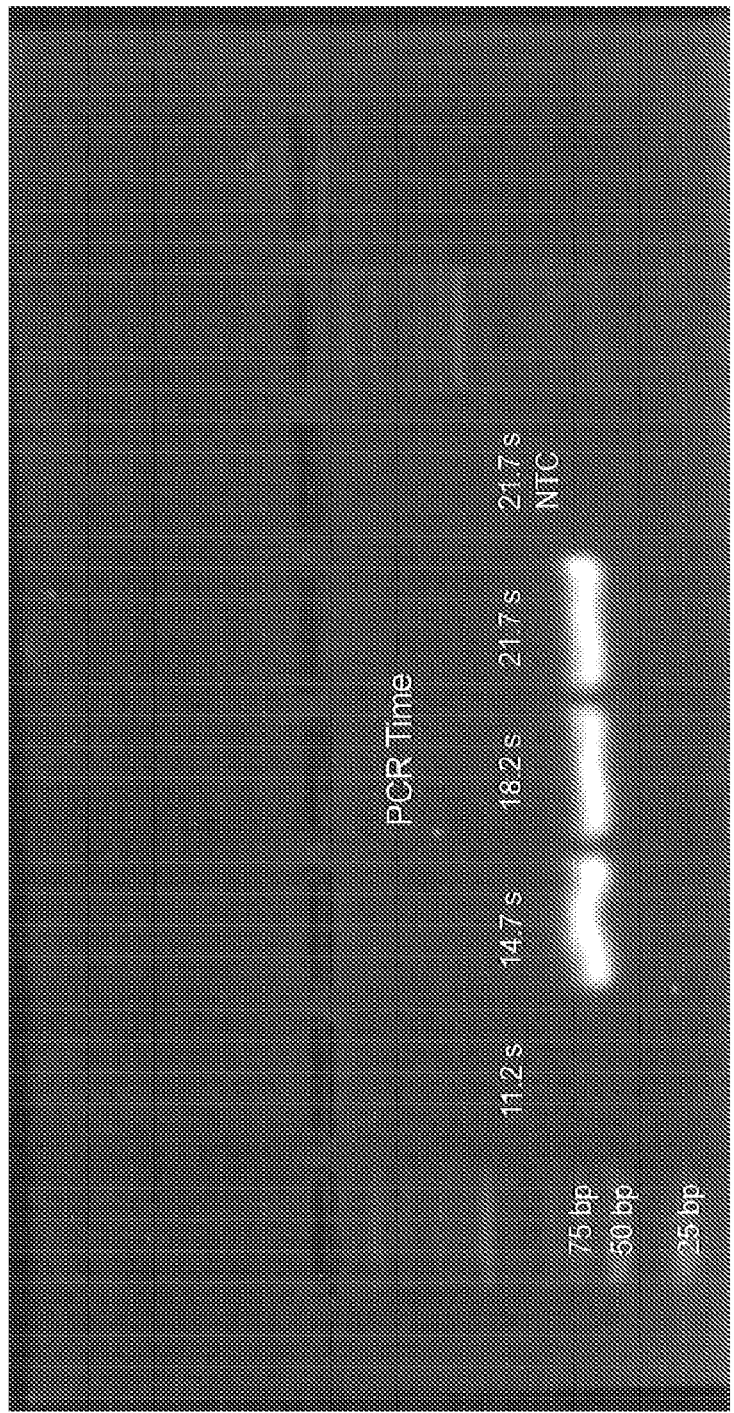

Each reaction was in a 1 µl volume with time based control (0.07 seconds in a 94° C. water bath, 0.1-0.4 seconds in a 60° C. water bath) for 35 cycles using 2-7 mM $MgCl_2$. The sample volume was 1 µl, with 5 ng human genomic DNA, 20 µM primers, and 8 µM polymerase. Using a 0.42 second per cycle protocol, when the $MgCl_2$ was 2-3 mM, no product was observed on melting curves (FIG. 12a) or gels (FIG. 12b). Minimal product was present at 4 mM, but a large amount of product was observed after amplification with 5-7 mM $MgCl_2$. At 5 mM $MgCl_2$, no products were observed on melting curves (FIG. 13a) or gels (FIG. 13b) with cycle times of 0.32 seconds, but large amounts of product were present at cycle times of 0.42 seconds, 0.52 seconds, and 0.62 seconds, demonstrating that specific, high yield 60 bp products can be obtained in PCR performed in under 15 seconds (35 cycles in 14.7 seconds). Thus, illustrative Mg++ concentrations are at least 4 mM, at least 5 mM, at least 6 mM, at least 7 mM, or more, and it is understood that these illustrative Mg++ concentrations may be used with any of the embodiments described herein.

Example 10

Figure 14A:
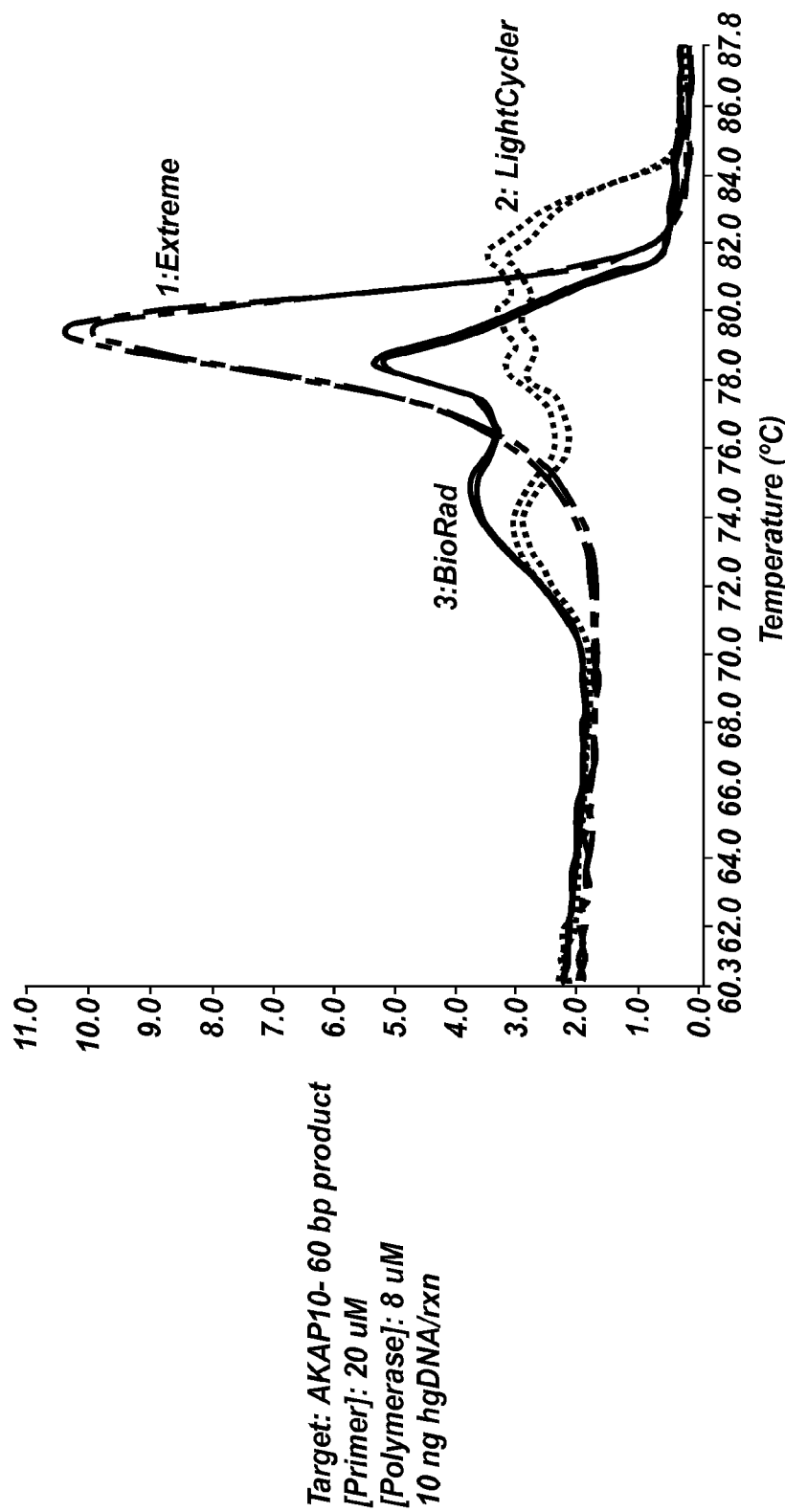
FIG. 14a shows negative derivative melting curves of a 60 bp fragment of AKAP10, as amplified on three different instruments: (1) extreme PCR, (2) LightCycler (Roche), and (3) CFX96 (BioRad).
Figure 14B:
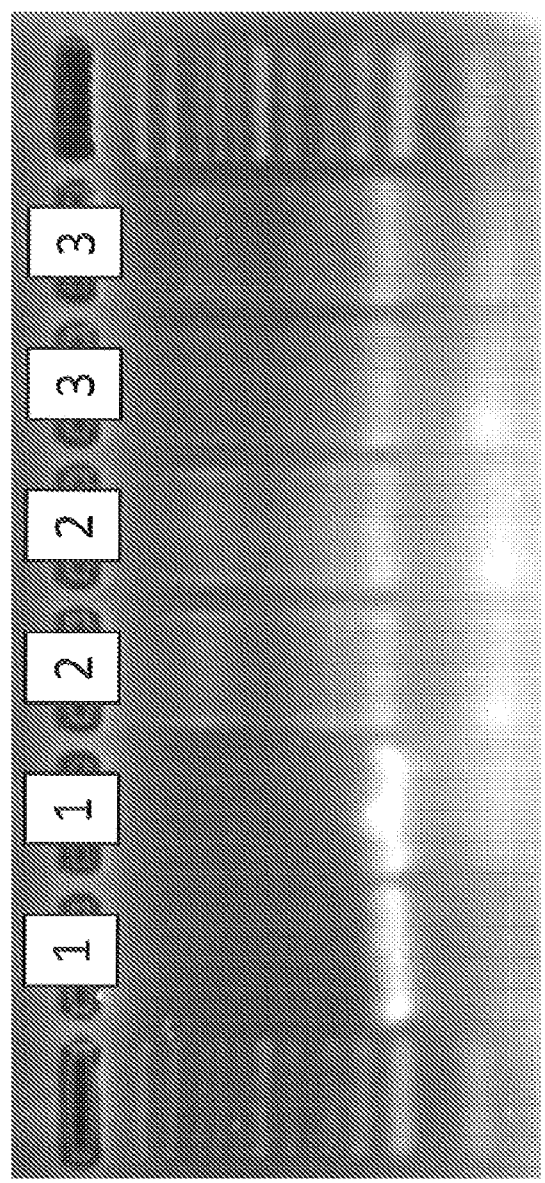

The high concentrations of primer and polymerase used in extreme PCR can have detrimental effects when used at slower cycling speeds. Non-specific products were obtained on rapid cycle or block based instruments that are 32- or 106-fold slower, respectively. FIG. 14a-b shows the results comparing amplification of the AKAP10 60 bp product used in Example 9, wherein amplification was performed using 20 µM of each primer, 8 µM KlenTaq and 10 ng human genomic DNA for 40 cycles using: (1) extreme PCR with set times of 0.5 s at 94° and 0.2 seconds at 60° giving a total time of approximately 17 seconds, (2) Rapid cycle PCR (Roche LightCycler) using set times of 10 s at 94° for an initial denaturation, followed by cycles of 85° for 0 seconds, and 60° for 0 seconds, giving a total time of approximately 9 minutes, and (3) Legacy (block) temperature cycling (BioRad CFX96) with a 10 s initial denaturation at 94°, following by temperature cycling for 0 s at 85° and 5 s at 60° with a total time of approximately 30 minutes. As can be seen, even the rapid cycling of the LightCycler resulted in quite a bit of non-specific amplification, while the extreme cycling conditions resulted in a single melting peak and minimal non-specific amplification on the gel.

It also noted that the yield is enhanced in extreme PCR, resulting from high primer and polymerase concentrations. Extreme PCR produced over 30-fold the amount of product compared to rapid cycle PCR, using quantitative PCR for comparison (data not shown).

Examples 1-10 were all performed using one or more of the devices described in FIGS. 1a-1d, or minor variations on those configurations. However, it is understood that the methods and reactions described herein may take place in a variety of instruments. The water baths and tubes used in these examples allow for sufficiently rapid temperature change to study the effects of elevated concentrations of primers and polymerase. However, other embodiments may be more suitable commercially. Microfluidics systems, with low volume and high surface area to volume ratios, may be well suited to extreme PCR. Such systems allow for rapid temperature changes required by the high concentrations of primers and polymerase that are used in extreme PCR. Microfluidics systems include micro-flow systems (35, 53) that incorporate miniaturized channels that repeatedly carry the samples through denaturation, annealing, and extension temperature zones. Some of these systems have already demonstrated effective PCR with cycle times as fast as 3 seconds for lower complexity targets. It is expected that more complex targets may be amplified in such systems if the polymerase is provided at a concentration of at least 0.5 µM and primers are each provided at a concentration of at least 2 µM. Stationary PCR chips and PCR droplet systems (54) may also benefit from increased primer and probe concentrations, as the volumes may be as small as 1 nl or smaller and may be low enough to permit very fast cycling. It is understood that the exact instrumentation is unimportant to the present invention, provided that the instrumentation temperature cycles fast enough to take advantage of increased primer and polymerase concentrations without suffering from the loss of specificity associated with higher primer concentrations at slower cycle speeds.

While the above examples all employ PCR, it is understood that PCR is illustrative only, and increased primer and enzyme concentrations combined with shorter amplification times are envisioned for nucleic acid amplification methods other than PCR. Illustrative enzymatic activities whose magnitude may be increased include polymerization (DNA polymerase, RNA polymerase or reverse transcriptase), ligation, helical unwinding (helicase), or exonuclease activity (5' to 3' or 3' to 5'), strand displacement and/or cleavage, endonuclease activity, and RNA digestion of a DNA/RNA hybrid (RNAse H). Amplification reactions include without limitation the polymerase chain reaction, the ligase chain reaction, transcription medicated amplification (including transcription-based amplification system, self-sustained sequence replication, and nucleic acid sequence-based amplification), strand displacement amplification, whole genome amplification, multiple displacement amplification, antisense RNA amplification, loop-mediated amplification, linear-linked amplification, rolling circle amplification, ramification amplification, isothermal oligonucleotide amplification, helicase chain reaction, and serial invasive signal amplification.

In general, as the enzyme activity is varied, the amplification time varies inversely by the same factor. For reactions that include primers, as the primer concentration is varied, the amplification time varies inversely by the same factor. When both primers and enzymes are required for amplification, both enzyme and primer concentrations should be varied in order to maximize the reaction speed. If primer annealing occurs in a unique segment of the amplification cycle (for example, a unique temperature during 3-temperature PCR), then the time required for satisfactory completion of primer annealing in that segment is expected to be inversely related to the primer concentration. Similarly, if the enzyme activity is required in a unique segment of the amplification cycle (for example, a unique temperature during 3-temperature PCR), then the time required for satisfactory completion of the enzymatic process in that segment is expected to be inversely related to the enzyme concentration within a certain range. Varying the primer or enzyme concentrations can be used to change the required times of their individual segments, or if both occur under the same conditions (such as in 2-temperature PCR or during an isothermal reaction process), it is expected that a change in both concentrations may be necessary to prevent one reaction from limiting the reaction speed. Increased Mg++ concentration can also be used in combination with increased enzyme and primer concentrations to further speed amplification processes. Higher Mg++ concentrations both increase the speed of primer annealing and reduce the time for many enzymatic reactions used in nucleic acid amplification.

Higher concentrations of Mg++, enzymes, and primers are particularly useful when they are accompanied by shorter amplification times or segments. When higher concentrations are used without shortening times, non-specific amplification products may occur in some cases, as the "stringency" of the reaction has been reduced. Reducing the amplification time or segment time(s) introduces a higher stringency that appears to counterbalance the loss of stringency from increased reactant concentrations. Conversely, reagent costs can be minimized by reducing the concentration of the reactants if these lower concentrations are counterbalanced by increased amplification times or segment times.

Increasing polymerase concentrations can reduce the time necessary for long-range PCR, illustratively where the target is 5-50 kb. Typically, 10 min to 30 min extension periods are used to amplify large targets because the target is so long that such times are needed: 1) for the polymerase to complete extension of a single target, and 2) for enzyme recycling to polymerize additional primed templates. This recycling of polymerase is not needed at the beginning of PCR, when the available enzyme outnumbers the primed template molecules. However, even before the exponential phase is finished, the number of polymerase molecules often becomes limiting and enzyme recycling is necessary. By increasing the concentration of the polymerase, the required extension period can be reduced to less than 5 minutes and possibly less than 2 minutes, while maintaining increased yield due to the high primer concentration. Although the actual enzyme speed is not increased, less recycling is necessary, affecting the minimum time required, approximately in a linear fashion with the enzyme concentration.

Cycle sequencing times can also be reduced by increasing primer and polymerase concentrations. Typically, in standard cycle sequencing primer concentrations are 0.16 µM and the combined annealing/extension period is 10 min at 50-60 degrees C. By increasing the primer and polymerase concentrations by 10-fold, the time required for annealing/extension can be reduced approximately 10-fold. In both long PCR and cycle sequencing, the expected time required is inversely proportional to the polymerase or primer concentration, whichever is limiting.

PCR of fragments with ligated linkers that are used as primers in preparation for massively parallel sequencing can be completed in much less time than currently performed by combining extreme temperature cycling with higher concentrations of primers, polymerase, and/or Mg++.

In all of the above applications, it is expected that the specificity of the reaction is maintained by shorter amplification times. Although high primer and polymerase concentrations are expected by those well versed in the art to cause difficulty from non-specific amplification, minimizing the overall cycle time and/or individual segment times results in high specificity and efficiency of the PCR.

TABLE 2

| Target | KCNE1 | KCNE1 | IRL10RB | IRL10RB | IRL10RB | NQO1 | AKAP10 |
| --- | --- | --- | --- | --- | --- | --- | --- |
| Amplicon Size (bp) | 45 | 45 | 49 | 49 | 58 | 102 | 60 |
| Polymerase | KlenTaq1 | KlenTaq1 | KlenTaq1 | KlenTaq1 | KlenTaq1 | KlenTaq1 | KlenTaq1 |
| [Polymerase] | 1 | 8 | 4 | 8 | 2 | 2 | 8 |
| [Primers] | 10 | 20 | 10 | 20 | 10 | 8 | 20 |
| # Cycles | 35 | RT | 35 | 35 | 39 | 30 | 35 |
| Cycle Time (s) | 0.8 | 0.91 | 0.73 | 0.45 | 0.97 | 1.93 | 0.42 |
| PCR Time (s) | 28 | RT | 26 | 16 | 38 | 58 | 14.7 |
| Hot Water Temp (° C.) | 95.5 | 95.5 | 95.5 | 95.5 | 95.5 | 95.5 | 95.5 |
| Cold Water Temp (° C.) | 20 | 58 | 30 | 30 | 30 | 72 | 59 |
| Hot Trigger Temp (° C.) | 90 | 85 | 90 | 90 | 90 | 90 | Time |
| Cold Trigger Temp (° C.) | 70 | 62 | 70 | 70 | 70 | Time | Time |
| Denaturation (° C.) | 90 | 85 | 90 | 90 | 90 | 90 | (82-85) w/TC |
| Ann/Ext (° C.) | 60 | 60 | 65 | 65 | 65 | 72 | 60 |
| Ann/Ext Time (s) | 0 | 0 | 0 | 0 | 0 | 1 | 0.1-0.4 |
| FIG. | 9a | 9a | 5a | 5a | 4c | 7a | 12a, |

TABLE 2-continued

| Tm | 81 | 81 | 80 | 80 | 83 | 85 | 79 |
|---|---|---|---|---|---|---|---|
| Mg++ | 3 | 3 | 3 | 3 | 3 | 3 | 2-7 |

| Target | Synthetic | Synthetic | Synthetic | Synthetic | Synthetic | Synthetic | Synthetic |
|---|---|---|---|---|---|---|---|
| Amplicon Size (bp) | 100 | 200 | 300 | 300 | 400 | 500 | 500 |
| Polymerase | KlenTaq1 | KlenTaq1 | KlenTaq1 | KlenTaq1 | KlenTaq1 | KlenTaq1 | KAPA2G FAST |
| [Polymerase] | 2 | 2 | 2 | 2 | 2 | 2 | 2 |
| [Primers] | 4 | 4 | 4 | 4 | 4 | 4 | 4 |
| # Cycles | RT | RT | 20 | RT | RT | RT | RT |
| Cycle Time (s) | 1.9 | 3.9 | 4.9 | 5.9 | 7.9 | 7.9 | 3.9 |
| PCR Time (s) | RT | RT | 98 | RT | RT | RT | RT |
| Hot Water Temp (° C.) | 95.5 | 95.5 | 95.5 | 95.5 | 95.5 | 95.5 | 95.5 |
| Cold Water Temp (° C.) | 76 | 76 | 76 | 76 | 76 | 76 | 76 |
| Hot Trigger Temp (° C.) | 92 | 92 | 92 | 92 | 92 | 92 | 92 |
| Cold Trigger Temp (° C.) | Time | Time | Time | Time | Time | Time | Time |
| Denaturation (° C.) | 92 | 92 | 92 | 92 | 92 | 92 | 92 |
| Ann/Ext (° C.) | 76 | 76 | 76 | 76 | 76 | 76 | 76 |
| Ann/Ext Time (s) | 0.5-3 | 1-5 | 4 | 1-7 | 3-9 | 3-11 | 1-5 |
| FIG. | 11a | 11b | 10a, 11c | 11c | 11d | 11e | 10b |
| Tm | 85 | 85 | 85 | 85 | 81/87 (2 domains) | 84 | 84 |
| Mg++ | 3 | 3 | 3 | 3 | 3 | 3 | 3 |

Time = time-based segment control does not have a temperature trigger
RT = real-time acquisition

TABLE 3

| | [Primer] (μM) | [Polymerase] (μM) | Polymerase Speed (nt/s) | Extension Length (bp) | Cycle Time (s) | Anneal/Extend Time (s) | [Mg++] |
|---|---|---|---|---|---|---|---|
| Standard | 0.05-0.5 | 0.0026-0.026 | 10-45 | 20-980 | 120-480 | 15-60 | 1.5 |
| Rapid Cycle | 0.2-1.0 | 0.063 | 55-90 | 20-480 | 20-60 | 1-10 | 3 |
| Extreme | 1-16 | 0.5-8 | 50-100 | 20-280 | 0.5-5 | <0.1-5 | 3-7 |
| Opt Extreme #1 | 10 | 2.50 | 60 | 29 | 0.73 | <0.1 | 3 |
| Opt Extreme #2 | 4 | 0.50 | 60 | 82 | 1.93 | 1 | 3 |
| Opt Extreme #3 | 4 | 0.75 | 60 | 280 | 4.9 | 4 | 3 |

If Required Annealing time = k1/[primer]

| | [Primer] (μM) | Anneal/Extend Time (s) | k1 (s * μM) |
|---|---|---|---|
| Min Standard | 0.05 | 15 | 0.75 |
| Max Standard | 0.5 | 60 | 30 |
| Min Rapid Cycle | 0.2 | 1 | 0.2 |
| Max Rapid Cycle | 1 | 10 | 10 |
| Opt Extreme #1 | 10 | 0.1 | 1 |
| Opt Extreme #2 | 4 | 1 | 4 |
| Opt Extreme #3 | 4 | 5 | 20 |

If required extension time = k2*product length/(polymerase speed*[polymerase])

| | k1 range (s*μM) |
|---|---|
| Standard | 0.75-30 |
| Rapid Cycle | 0.2-10 |
| Extreme | 1-20 |

| | [Polymerase] (μM) | Polymerase Speed (nt/s) | Extension Length (bp) | Anneal/Extend Time (s) | k2 (1/μM) |
|---|---|---|---|---|---|
| Opt Extreme #1 | 2.5 | 60 | 29 | 0.1 | 0.52 |
| Opt Extreme #2 | 0.5 | 60 | 82 | 1 | 0.37 |
| Opt Extreme #3 | 0.75 | 60 | 280 | 4 | 0.64 |

Specific conditions for extreme PCR are shown in Table 2. All data are presented except for the simultaneous optimization experiments for polymerase and primer concentrations for 3 of the targets. In Table 3, the quantitative relationships between variables are detailed. The inverse proportionality that relates the required annealing time to the primer concentration is approximately constant (k1) and defined by the equation (Required annealing time)=k1/[primer]. Using a range of typical values for these variables under conditions of legacy (standard) PCR, rapid cycle PCR, and extreme PCR produces ranges for the inverse proportionality constant that largely overlap (legacy 0.75-30, rapid cycle 0.2-10, and extreme 1-20). Because of this constant inverse proportionality, desired annealing times outside of those currently performed can be used to predict the required primer concentrations for the desired time. For example, using a constant of 5 (s*µM), for an annealing time of 0.01 s, a primer concentration of 500 µM can be calculated. Conversely, if a primer concentration of 0.01 µM were desired, the required annealing time would be 500 seconds. Although these conditions are outside the bounds of both legacy and extreme PCR, they predict a relationship between primer concentrations and annealing times that are useful for PCR success. Reasonable bounds for k1 across legacy, rapid cycle and extreme PCR are 0.5-20 (s×µM), more preferred 1-10 (s×µM) and most preferred 3-6 (s×µM).

Similar calculations can be performed to relate desired extension times to polymerase concentration, polymerase speed, and the length of the product to be amplified. However, because of many additional variables that affect PCR between legacy, rapid cycle and extreme PCR (polymerase, Mg++, buffers), performed in different laboratories over time, it may be best to look at the well-controlled conditions of extreme PCR presented here to establish an inverse proportionality between variables. This allows a quantitative expression between polymerase concentration, polymerase speed, product length, and the required extension time under extreme PCR conditions. The defining equation is (Required Extension Time)=k2(product length)/([polymerase]*(polymerase speed)). The experimentally determined k2 is defined as the proportionality constant in the above equation under conditions of constant temperature, $Mg^{++}$, type of polymerase, buffers, additives, and concentration of dsDNA dye. For the 3 extreme PCR targets with two dimensional optimization of [polymerase] and [primer], the [polymerase] at the edge of successful amplification can be discerned across primer concentrations and related to the other 3 variables. As shown in Table 3, the values of k2 for these 3 different targets vary by less than a factor of 2, from which it is inferred that k2 is a constant and can be used to predict one variable if the others are known. The required extension time is proportional to the extension length (product length minus the primer length) and inversely proportional to the polymerase speed and concentration of polymerase. k2 has units of (1/µM) and an optimal value for the extreme PCR conditions used here of 0.5 (1/µM) with a range of 0.3-0.7 (1/µM). Similar values for k2 could be derived for other reaction conditions that vary in polymerase type, Mg++ concentration or different buffer or dye conditions.

Extreme PCR can be performed in any kind of container, as long as the temperature of the sample can be changed quickly. In addition to standard tubes and capillaries, microdroplets of aqueous reactions suspended in an oil stream or thin 2-dimensional wafers provide good thermal contact. Continuous flow PCR of a sample stream (either dispersed as droplets, separated by bubbles, or other means to prevent mixing) past spatial segments at different temperatures is a good method for the temperature control needed for the speeds of extreme PCR.

REFERENCES

1. Wittwer C T, Reed G B, Ririe K M. Rapid cycle DNA amplification. In: Mullis I K, Ferre F, Gibbs R, eds. The polymerase chain reaction, Vol. Deerfield Beach, Fla.: 174-181, 1994.
2. Wittwer C T, Fillmore G C, Hillyard D R. Automated polymerase chain reaction in capillary tubes with hot air. Nucleic Acids Res 1989; 17:4353-7.
3. Wittwer C T, Fillmore G C, Garling D J Minimizing the time required for DNA amplification by efficient heat transfer to small samples. Anal Biochem 1990; 186:328-31.
4. Wittwer C T, Garling D J. Rapid cycle DNA amplification: time and temperature optimization. Biotechniques 1991; 10:76-83.
5. Wittwer C T, Marshall B C, Reed G H, Cherry J L. Rapid cycle allele-specific amplification: studies with the cystic fibrosis delta F508 locus. Clin Chem 1993; 39:804-9.
6. Schoder D, Schmalwieser A, Schauberger G, Hoorfar J, Kuhn M, Wagner M. Novel approach for assessing performance of PCR cyclers used for diagnostic testing. J Clin Microbiol 2005; 43:2724-8.
7. Herrmann M G, Durtschi J D, Wittwer C T, Voelkerding K V. Expanded instrument comparison of amplicon DNA melting analysis for mutation scanning and genotyping. Clin Chem 2007; 53:1544-8.
8. Hellmann M G, Durtschi J D, Bromley L K, Wittwer C T, Voelkerding K V.
Amplicon DNA melting analysis for mutation scanning and genotyping: cross-platform comparison of instruments and dyes. Clin Chem 2006; 52:494-503.
9. Raja S, El-Hefnawy T, Kelly L A, Chestney M L, Luketich J D, Godfrey T E.
Temperature-controlled primer limit for multiplexing of rapid, quantitative reverse transcription-PCR assays: application to intraoperative cancer diagnostics. Clin Chem 2002; 48:1329-37.
10. Wittwer C T, Ririe K M, Andrew R V, David D A, Gundry R A, Balis U J. The LightCycler: a microvolume multisample fluorimeter with rapid temperature control. Biotechniques 1997; 22:176-81.
11. Wittwer C T, Ririe K M, Rasmussen R P. Fluorescence monitoring of rapid cycle PCR for quantification. In: Ferre F, ed. Gene Quantification, New York: Birkhauser, 1998:129-44.
12. Elenitoba-Johnson O, David D, Crews N, Wittwer C T. Plastic vs glass capillaries for rapid-cycle PCR. Biotechniques 2008; 44:487-8,490,492.
13. Roper M G, Easley C J, Landers J P. Advances in polymerase chain reaction on microfluidic chips. Anal Chem 2005; 77:3887-93.
14. Zhang C, Xing D. Miniaturized PCR chips for nucleic acid amplification and analysis: latest advances and future trends. Nucleic Acids Res 2007; 35:4223-37.
15. Cheng J, Shoffner M A, Hvichia G E, Kricka L J, Wilding P Chip PCR. II. Investigation of different PCR amplification systems in microfabricated silicon-glass chips. Nucleic Acids Res 1996; 24:380-5.
16. Woolley A T, Hadley D, Landre P, deMello A J, Mathies R A, Northrup M A. Functional integration of PCR amplification and capillary electrophoresis in a microfabricated DNA analysis device. Anal Chem 1996; 68:4081-6.
17. Neuzil P, Zhang C, Pipper J, Oh S, Zhuo L. Ultra fast miniaturized real-time PCR: 40 cycles in less than six minutes. Nucleic Acids Res 2006; 34:e77.
18. Oda R P, Strausbauch M A, Huhmer A F, Borson N, Jurrens S R, Craighead J, et al. Infrared-mediated thermocycling for ultrafast polymerase chain reaction amplification of DNA. Anal Chem 1998; 70:4361-8.
19. Roper M G, Easley C J, Legendre L A, Humphrey J A, Landers J P. Infrared temperature control system for a 19. completely noncontact polymerase chain reaction in microfluidic chips. Anal Chem 2007; 79:1294-300.
20. Friedman N A, Meldrum D R. Capillary tube resistive thermal cycling. Anal Chem 1998; 70:2997-3002.
21. Heap D M, Herrmann M G, Wittwer C T. PCR amplification using electrolytic resistance for heating and temperature monitoring. Biotechniques 2000; 29:1006-12.
22. Kopp M U, Mello A J, Manz A. Chemical amplification: continuous-flow PCR on a chip. Science 1998; 280:1046-8.
23. Hashimoto M, Chen P C, Mitchell M W, Nikitopoulos D E, Soper. SA, Murphy M C. Rapid PCR in a continuous flow device. Lab Chip 2004; 4:638-45.
24. Crews N, Wittwer C, Gale B. Continuous-flow thermal gradient PCR. Biomed Microdevices 2008; 10; 187-95.
25. Chiou J T, Matsudaira P T, Ehrlich D J. Thirty-cycle temperature optimization of a closed-cycle capillary PCR machine. Biotechniques 2002; 33:557-8, 60, 62.
26. Frey O, Bonneick S, Hierlemann A, Lichtenberg J. Autonomous microfluidic multi-channel chip for real-time PCR with integrated liquid handling. Biomed Microdevices 2007; 9:711-8.
27. Chen J, Wabuyele M, Chen H, Patterson D, Hupert M, Shadpour H, et al. Electrokinetically synchronized polymerase chain reaction microchip fabricated in polycarbonate. Anal Chem 2005; 77:658-66.
28. Sun Y, Kwok Y C, Nguyen N T. A circular ferrofluid driven microchip for rapid polymerase chain reaction. Lab Chip 2007; 7:1012-7.
29. Agrawal N, Hassan Y A, Ugaz V M. A pocket-sized convective PCR thermocycler. Angew Chem Int Ed Engl 2007; 46:4316-9.
30. Zhang C, Xu J, Ma W, Zheng W. PCR microfluidic devices for DNA amplification. Biotechnol Adv 2006; 24:243-84.
31. Wheeler E K, Benett W, Stratton P, Richards J, Chen A, Christian A, et al. Convectively driven polymerase chain reaction thermal cycler. Anal Chem 2004; 76:4011-6.
32. Belgrader P, Benett W, Hadley D, Long G, Mariella R, Jr., Milanovich F, et al. Rapid pathogen detection using a microchip PCR array instrument. Clin Chem 1998; 44:2191-4.
33. Terazona H, Takei, H, Hattori A, Yasuda K. Development of a high-speed real-time polymerase chain reaction system using a circulating water-based rapid heat exchange. Jap J Appl Phys 2010; 49:06GM05.
34. Wheeler E K, Hara C A, Frank J, Deotte J, Hall S B, Benett W, Spadaccini C, Beer N R. Under-three minute PCR: Probing the limits of fast amplification. Analyst 2011.
35. Fuchiwaki Y, Nagai H, Saito M, Tamiya E. Ultra-rapid flow-through polymerase chain reaction microfluidics using vapor pressure. Biosens Bioelect 2011; 27:88-94.
36. Maltezos G, Johnston M, Taganov K, Srichantaratsamee C, Gorman J, Baltimore D, Chantratita W and Scherer A, Appl. Phys. Lett., 2010, 97, 264101.
37. Wilhelm J, Hahn M, Pingoud A. Influence of DNA target melting behavior on real-time PCR quantification. Clin Chem 2000; 46:1738-43.
38. Zuna J, Muzikova K, Madzo J, Krejci O, Trka J. Temperature non-homogeneity in rapid airflow-based cycler significantly affects real-time PCR. Biotechniques 2002; 33:508, 10, 12.
39. von Kanel T, Adolf F, Schneider M, Sanz J, Gallati S. Sample number and denaturation time are crucial for the accuracy of capillary-based LightCyclers. Clin Chem 2007; 53:1392-4.
40. Wittwer C T, Hellmann M G. Rapid thermal cycling and PCR kinetics. In: Innis M, Gelfand D, Sninsky J, eds. PCR Methods Manual, Vol. San Diego: Academic Press, 1999:211-29.
41. Wittwer C T, Reed G H, Gundry C N, Vandersteen J G, Pryor R J. High-resolution genotyping by amplicon melting analysis using LCGreen. Clin Chem 2003; 49:853-60.
42. von Ahsen N, Wittwer C T, Schutz E. Oligonucleotide melting temperatures under PCR conditions: nearest-neighbor corrections for Mg(2+), deoxynucleotide triphosphate, and dimethyl sulfoxide concentrations with comparison to alternative empirical formulas. Clin Chem 2001; 47:1956-61.
43. Ririe K M, Rasmussen R P, Wittwer C T. Product differentiation by analysis of DNA melting curves during the polymerase chain reaction. Anal Biochem 1997; 245:154-60.
44. Wittwer C T, Heirmann M G, Moss A A, Rasmussen R P. Continuous fluorescence monitoring of rapid cycle DNA amplification. Biotechniques 1997; 22:130-1, 4-8.
45. Weis J H, Tan S S, Martin B K, Wittwer C T. Detection of rare mRNAs via quantitative RT-PCR. Trends Genet 1992; 8:263-4.
46. Brown R A, Lay M J, Wittwer C T. Rapid cycle amplification for construction of competitive templates. In: Horton R M, Tait R C, eds. Genetic Engineering with PCR, Vol. Norfolk: Horizon Scientific Press, 1998:57-70.
47. Ausubel et al., Current Protocols in Molecular Biology, John Wiley & Sons, New York, N.Y., 1998
48. Whitney S E, "Analysis of rapid thermocycling for the polymerase chain reaction," Ph.D. thesis, University of Nebraska, 2004.
49. Lawyer F C, Stoffel S, Saiki R K, Chang S Y, Landre P A, Abramson R D, Gelfand D H. High-level expression, purification and enzymatic characterization of full-length *Thermus aquaticus* DNA polymerase and a truncated form deficient of 5' to 3' exonuclease activity. PCR Meth Appl. 1993; 2:275-287.
50. Innis M A, Myamo K B, Gelfand D H, Brow M A D. DNA sequencing with *Thermus aquaticus* DNA polymerase and direct sequencing of polymerase chain reaction-amplified DNA. Proc. Natl. ACad. Sci USA 1988; 85:9436-40.
51. Terazono H, Hattori A, Takei H, Takeda K, Yasuda K. Development of 1480 nm photothermal high-speed real-time polymerase chain reaction system for rapid nucleotide recognition. Jpn J Appl Phys. 2008; 47:5212-6.
52. Wittwer C T, Rasmussen R P, Ririe K M. Rapid PCR and melting curve analysis. In: The PCR Revolution: Basic Technologies and Applications, Bustin S A, ed. Cambridge Univ Press, New York, 48-69, 2010.
53. Fuchiwaki Y, Saito M, Wakida S, Tamiya E, Nagai H. A practical liquid plug flow-through polymerase chain-reaction system based on a heat-resistant resin chip. Anal Sci. 2011; 27:225-30.
54. Kim H, Dixit S, Green C J, Faris G W. Nanodroplet real-time PCR system with laser assisted heating. Optics Express 2009; 17:218-27.
55. Obeid P J, Christopoulos T K, Crabtree H J, Backhouse C J. Microfabricated device for DNA and RNA amplification by continuous-flow polymerase chain reaction and reverse transcription-polymerase chain reaction with cycle number selection. Anal Chem 2003; 75:288-95.
56. Giordano B C, Ferrance J, Swedberg S, Huhmer A F R, Landers J P. Polymerase chain reaction in polymeric microchips: DNA amplification in less than 240 seconds. Anal Biochem 2001; 291:124-132.

Although the invention has been described in detail with reference to preferred embodiments, variations and modifications exist within the scope and spirit of the invention as described and defined in the following claims.

The invention claimed is:

1. A reaction mixture for performing PCR on a target eukaryotic DNA, the reaction mixture comprising:
   dNTPs,
   a polymerase provided at a concentration of at least 0.5 μM,
   a pair of primers configured for amplifying the target eukaryotic DNA, wherein each primer of the pair of primers are provided at a concentration of at least 2 μM, and
   a sample of eukaryotic genomic DNA.

2. The reaction mixture of claim 1, wherein the concentration for each primer of the pair of primers is greater than 2.5 μM.

3. The reaction mixture of claim 1, further comprising a $Mg^{++}$ concentration of at least 4 mM.

4. The reaction mixture of claim 1, wherein the reaction mixture is provided together with instructions for using the reaction mixture and for performing PCR using a temperature cycling profile wherein each cycle is completed in a cycle time less than 20 seconds per cycle.

5. The reaction mixture of claim 4, wherein the cycle time is less than 10 seconds per cycle.

6. The reaction mixture of claim 1, wherein the polymerase is KlenTaq provided at the concentration of at least 1.0 μM.

* * * * *

UNITED STATES PATENT AND TRADEMARK OFFICE
CERTIFICATE OF CORRECTION

PATENT NO. : 11,021,744 B2
APPLICATION NO. : 16/179383
DATED : June 1, 2021
INVENTOR(S) : Wittwer et al.

Page 1 of 1

It is certified that error appears in the above-identified patent and that said Letters Patent is hereby corrected as shown below:

In the Specification

Column 7, Line 66: Please correct "at least 2 and" to read -- at least 2 µM and --

Column 8, Line 51: Please correct "0.5 and" to read -- 0.5 µM and --

Signed and Sealed this
Fifteenth Day of February, 2022

Drew Hirshfeld
*Performing the Functions and Duties of the*
*Under Secretary of Commerce for Intellectual Property and*
*Director of the United States Patent and Trademark Office*